(12) United States Patent
Klein et al.

(10) Patent No.: US 11,993,865 B2
(45) Date of Patent: *May 28, 2024

(54) SELECTION OF AFFINITY REAGENTS

(71) Applicant: Nautilus Subsidiary, Inc., Seattle, WA (US)

(72) Inventors: Joshua S. Klein, Pacifica, CA (US); Jarrett Egertson, Rancho Palos Verdes, CA (US); Tracy Chan, Daly City, CA (US); Sonal Tonapi, Sunnyvale, CA (US); Parag Mallick, San Mateo, CA (US); Minyong Chung, Menlo Park, CA (US); Abdullah Ozer, Ithaca, NY (US); Elliott Sorelle, Redwood City, CA (US); David Stern, Menlo Park, CA (US)

(73) Assignee: Nautilus Subsidiary, Inc., Seattle, WA (US)

( * ) Notice: Subject to any disclaimer, the term of this patent is extended or adjusted under 35 U.S.C. 154(b) by 244 days.

This patent is subject to a terminal disclaimer.

(21) Appl. No.: 17/424,435

(22) PCT Filed: Nov. 20, 2019

(86) PCT No.: PCT/US2019/062482
§ 371 (c)(1),
(2) Date: Jul. 20, 2021

(87) PCT Pub. No.: WO2020/106889
PCT Pub. Date: May 28, 2020

(65) Prior Publication Data
US 2023/0107579 A1   Apr. 6, 2023

Related U.S. Application Data

(60) Provisional application No. 62/770,136, filed on Nov. 20, 2018.

(51) Int. Cl.
*C40B 30/04* (2006.01)
*C12N 15/10* (2006.01)

(52) U.S. Cl.
CPC .......... *C40B 30/04* (2013.01); *C12N 15/1048* (2013.01); *C12N 15/1072* (2013.01)

(58) Field of Classification Search
None
See application file for complete search history.

(56) References Cited

U.S. PATENT DOCUMENTS

| 5,324,633 A | 6/1994 | Fodor et al. |
| 5,445,934 A | 8/1995 | Fodor et al. |

(Continued)

FOREIGN PATENT DOCUMENTS

| CN | 100500865 C | 6/2009 |
| EP | 1105529 B2 | 5/2013 |

(Continued)

OTHER PUBLICATIONS

Office Action in CN201980089624.6, mailed Jan. 8, 2024, 27 pages.

(Continued)

*Primary Examiner* — Christian C Boesen
(74) *Attorney, Agent, or Firm* — Orrick, Herrington & Sutcliffe, LLP

(57) ABSTRACT

Methods and systems are provided herein for selecting an affinity reagent which binds a desired peptide epitope in a plurality of sequence contexts. The method relies on obtaining a peptide library, each peptide having the sequence $\alpha X \beta$, wherein X is the desired peptide epitope, wherein each of $\alpha$ and $\beta$ comprise an amino acid, using the peptide library to select an affinity reagent.

26 Claims, 21 Drawing Sheets

Specification includes a Sequence Listing.

No binding for top hit to control peptides

(56) References Cited

U.S. PATENT DOCUMENTS

| | | |
|---|---|---|
| 5,695,934 A | 12/1997 | Brenner |
| 5,849,878 A | 12/1998 | Cantor et al. |
| 5,863,722 A | 1/1999 | Brenner |
| 5,888,737 A | 3/1999 | DuBridge et al. |
| 5,919,626 A | 7/1999 | Shi et al. |
| 6,140,489 A | 10/2000 | Brenner |
| 6,175,002 B1 | 1/2001 | DuBridge et al. |
| 6,391,625 B1 | 5/2002 | Park et al. |
| 6,589,726 B1 | 7/2003 | Butler et al. |
| 6,610,482 B1 | 8/2003 | Fodor et al. |
| 6,720,595 B2 | 4/2004 | Clevenger et al. |
| 6,806,361 B1 | 10/2004 | Kajisa et al. |
| 6,824,866 B1 | 11/2004 | Glazer et al. |
| 6,998,241 B2 | 2/2006 | Boga |
| 7,022,515 B2 | 4/2006 | Herron et al. |
| 7,148,058 B2 | 12/2006 | Charych et al. |
| 7,158,224 B2 | 1/2007 | Montagu |
| 7,239,860 B2 | 7/2007 | Stoks |
| 7,252,954 B2 | 8/2007 | Wang et al. |
| 7,545,496 B2 | 6/2009 | Prins et al. |
| 7,635,562 B2 | 12/2009 | Harris et al. |
| 7,794,799 B1 | 9/2010 | Kim et al. |
| 7,842,793 B2 | 11/2010 | Rothemund |
| 7,932,060 B2 | 4/2011 | Nadeau et al. |
| 8,133,719 B2 | 3/2012 | Drmanac et al. |
| 8,467,061 B2 | 6/2013 | McCaffrey et al. |
| 8,501,923 B2 | 8/2013 | Rothemund |
| 8,680,483 B2 | 3/2014 | Haga et al. |
| 8,865,077 B2 | 10/2014 | Chiou et al. |
| 8,951,781 B2 | 2/2015 | Reed et al. |
| 9,193,996 B2 | 11/2015 | Buermann et al. |
| 9,340,416 B2 | 5/2016 | Maune et al. |
| 9,528,984 B2 | 12/2016 | Mitra |
| 9,606,058 B2 | 3/2017 | Rothberg et al. |
| 9,678,012 B2 | 6/2017 | Rothberg et al. |
| 9,880,175 B2 | 1/2018 | Mitra |
| 9,921,157 B2 | 3/2018 | Rothberg et al. |
| 10,175,248 B2 | 1/2019 | Mitra |
| 10,330,598 B2 | 6/2019 | Schleipen et al. |
| 10,351,909 B2 | 7/2019 | Drmanac et al. |
| 10,473,654 B1 | 11/2019 | Mallick |
| 10,571,473 B2 | 2/2020 | Mitra |
| 10,605,730 B2 | 3/2020 | Rothberg et al. |
| 10,712,274 B2 | 7/2020 | Rothberg et al. |
| 10,741,382 B2 | 8/2020 | Sills et al. |
| 10,775,305 B2 | 9/2020 | Rothberg et al. |
| 10,829,816 B2 | 11/2020 | Staker et al. |
| 10,845,308 B2 | 11/2020 | Rothberg et al. |
| 10,895,534 B2 | 1/2021 | Finkelstein et al. |
| 10,921,317 B2 | 2/2021 | Mallick |
| 10,948,488 B2 | 3/2021 | Mallick |
| 11,203,612 B2 | 12/2021 | Gremyachinskiy et al. |
| 2003/0054408 A1 | 3/2003 | Ravi et al. |
| 2004/0023413 A1 | 2/2004 | Opalsky |
| 2004/0091931 A1 | 5/2004 | Gold |
| 2004/0209383 A1 | 10/2004 | Yin et al. |
| 2005/0054118 A1 | 3/2005 | Lebrun |
| 2005/0095577 A1 | 5/2005 | Yang et al. |
| 2005/0287523 A1 | 12/2005 | Letant et al. |
| 2006/0035220 A1 | 2/2006 | Tashiro et al. |
| 2006/0160234 A1 | 7/2006 | Lopez-Avila et al. |
| 2006/0263769 A1 | 11/2006 | Luo et al. |
| 2007/0188750 A1 | 8/2007 | Lundquist et al. |
| 2007/0218503 A1 | 9/2007 | Mitra |
| 2009/0161100 A1 | 6/2009 | Minot et al. |
| 2009/0214591 A1 | 8/2009 | Manucharyan et al. |
| 2009/0247414 A1 | 10/2009 | Obradovic et al. |
| 2009/0257952 A1 | 10/2009 | Cochran et al. |
| 2009/0311774 A1 | 12/2009 | Chiou et al. |
| 2010/0111768 A1 | 5/2010 | Banerjee et al. |
| 2011/0065807 A1 | 3/2011 | Radovic-Moreno et al. |
| 2011/0263688 A1 | 10/2011 | Barany et al. |
| 2012/0077688 A1 | 3/2012 | Bergo et al. |
| 2013/0310274 A1 | 11/2013 | Meng et al. |
| 2015/0160204 A1 | 6/2015 | Mitra |
| 2015/0185199 A1 | 7/2015 | Joo et al. |
| 2015/0330974 A1 | 11/2015 | Staker et al. |
| 2016/0060687 A1 | 3/2016 | Zhu et al. |
| 2016/0102344 A1 | 4/2016 | Niemeyer et al. |
| 2016/0167413 A1 | 6/2016 | Furuya |
| 2016/0310926 A1 | 10/2016 | Sun et al. |
| 2017/0044245 A1 | 2/2017 | Meng et al. |
| 2017/0191051 A1 | 7/2017 | Nikiforov |
| 2017/0283868 A1 | 10/2017 | Beechem et al. |
| 2019/0195869 A1 | 6/2019 | Fan et al. |
| 2020/0025752 A1 | 1/2020 | Gopinath et al. |
| 2020/0025757 A1 | 1/2020 | Gopinath et al. |
| 2020/0232994 A1 | 7/2020 | Mitra |
| 2020/0318101 A1 | 10/2020 | Mallick et al. |
| 2021/0278400 A1 | 1/2021 | Mallick |
| 2021/0101930 A1 | 4/2021 | Gremyachinskiy et al. |
| 2021/0223238 A1 | 7/2021 | Mallick |
| 2021/0239705 A1 | 8/2021 | Mallick |
| 2021/0355483 A1 | 11/2021 | Chee et al. |
| 2022/0017567 A1 | 1/2022 | Gremyachinskiy et al. |
| 2022/0050049 A1 | 2/2022 | Indermuhle et al. |
| 2022/0074931 A1 | 3/2022 | Mallick |

FOREIGN PATENT DOCUMENTS

| | | |
|---|---|---|
| EP | 2872898 B1 | 12/2016 |
| EP | 3498865 B1 | 10/2020 |
| JP | 2007-525143 A | 9/2007 |
| JP | 2017504795 A | 2/2017 |
| WO | WO-0146675 A2 | 6/2001 |
| WO | WO-02086081 A2 | 10/2002 |
| WO | 2004/046317 A2 | 6/2004 |
| WO | WO-2006135527 A2 | 12/2006 |
| WO | WO-2007117444 A2 | 10/2007 |
| WO | WO-2007120208 A3 | 8/2008 |
| WO | WO-2007123744 A3 | 11/2008 |
| WO | WO-2009012343 A2 | 1/2009 |
| WO | WO-2010065531 A1 | 6/2010 |
| WO | WO-2014078855 A1 | 5/2014 |
| WO | WO-2015097077 A2 | 7/2015 |
| WO | WO-2016174525 A1 | 11/2016 |
| WO | WO-2017127762 A1 | 7/2017 |
| WO | WO-2018102759 A1 | 6/2018 |
| WO | WO-2019036055 A2 | 2/2019 |
| WO | WO-2019195633 | 10/2019 |
| WO | WO-2019236749 A2 | 12/2019 |
| WO | WO-2020106889 A1 | 5/2020 |
| WO | WO-2020108588 A1 | 6/2020 |
| WO | WO-2020223368 A1 | 11/2020 |

OTHER PUBLICATIONS

EP3884048 European Search Report dated Jul. 15, 2022.
3-Aminopropyl)triethoxysilane. Wikipedia.org. Apr. 5, 2019 (Apr. 5, 2019), entire document esp p. 1 (https://en.wikipedia.org/w/index.php?title=(3-Aminopropyl)triethoxysilane&oldid=891131780).
Arnold et al. "The majority of immunogenic epitopes generate CD44-T cells that are dependent on MHC class II-bound peptide-flanking residues," J Immunol, Jul. 15, 2002 (Jul. 15, 2002), vol. 169, No. 2, pp. 739-749.
Ayoglu, et al., Autoantibody Profiling in Multiple Sclerosis Using Arrays of Human Protein Fragments, Molecular & Cellular Proteomics, (12)9 Sep. 1, 2013 (Sep. 1, 2013), pp. 2657-2672, XP055294116, US ,ISSN: 1535-9476, DOI: 10.1074/mcp.M112.026757.
Blatch, et al. The tetratricopeptide repeat: a structural motif mediating protein-protein interactions. Bioessays Nov. 1999;21(11):932-939.
Buenrostro, et al. Quantitative analysis of RNA-protein interactions on a massively parallel array for mapping biophysical and evolutionary landscapes. Nat Biotechnol. Jun. 2014; 32(6): 562-568.
Bunka et al. "Production and characterization of RNA aptamers specific for amyloid fibril epitopes," J Biol Chem, Sep. 18, 2007 (Sep. 18, 2007), vol. 282, No. 47, pp. 34500-34509.
Buus, et al. High-resolution mapping of linear antibody epitopes using ultrahigh-density peptide microarrays. Molecular & Cellular Proteomics 11.12 (2012): 1790-1800.

(56) References Cited

OTHER PUBLICATIONS

Choung, et al. Determination of B-Cell Epitopes in Patients with Celiac Disease: Peptide Microarrays. PloS one vol. 11(1) e0147777. Jan. 29, 2016, doi:10.1371/journal.pone.0147777.
Co-pending U.S. Appl. No. 17/390,666, inventor Mallick; Parag, filed Jul. 30, 2021.
Co-pending U.S. Appl. No. 17/496,742, inventors Gremyachinskiy; Dmitriy et al., filed Oct. 7, 2021.
Domenyuk, et al. Plasma Exosome Profiling of Cancer Patients by a Next Generation Systems Biology Approach. Sci Rep. 2017; 7: 42741.
EP17877076.4 The Extended European Search Report dated Aug. 11, 2020.
EP18846671.8 Extended European Search Report dated Apr. 23, 2021.
Fodor, et al. Light-Directed, Spatially Addressable Parallel Chemical Synthesis. Science, vol. 251, 767-773, 1991.
Ford et al. "Degenerate recognition of T cell epitopes: impact of T cell receptor reserve and stability of peptide:MHC complexes," Mol Immunol, Feb. 1, 2004 (Feb. 1, 2004), vol. 40, No. 14-15, pp. 1019-1025.
Hung, et al. Large-area spatially ordered arrays of gold nanoparticles directed by lithographically confined DNA origami. Nat Nanotechnol. Feb. 2010;5(2):121-6. doi: 10.1038/nnano.2009.450. Epub Dec. 20, 2009.
Hunniger, et al. Just in time-selection: A rapid semiautomated SELEX of DNA aptamers using magnetic separation and BEAMing. Anal Chem. Nov. 4, 2014;86(21):10940-7.
Kang, H. The prevention and handling of the missing data. Korean journal of anesthesiology vol. 64,5 (2013): 402-6. doi:10.4097/kjae.2013.64.5.402.
Laurenson, et al. Development of peptide aptamer microarrays for detection of HPV16oncoproteins in cell extracts, Analytical Biochemistry, Academic Press, Amsterdam,NL, vol. 410, No. 2, Oct. 30, 2010 (Oct. 30, 2010), pp. 161-170, XP028146256,ISSN: 0003-2697,DOI: 10.1016/J.AB.2010.10.038.
Lin et al. Development of a novel peptide microarray for large-scale epitope mapping of food allergens, Journal of Allergy and Clinical Immunology, Elsevier, Amsterdam, NL,vol. 124, No. 2, Aug. 1, 2009 (Aug. 1, 2009), pp. 315-322.e3, XP026390934, ISSN: 0091-6749,DOI: 10.1016/J.JACI.2009.05.024.
Lutz, et al. Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.
McKay, et al. Click Chemistry in Complex Mixtures: Bioorthogonal Bioconjugation. Chem Biol. Sep. 18, 2014; 21(9): 1075-1101.
Meldal, et al. Cu-catalyzed azide-alkyne cycloaddition. Chem Rev. Aug. 2008;108(8):2952-3015. doi: 10.1021/cr0783479.
Nonobe et al. A tabu search approach to the constraint satisfaction problem as a general problem solver. Eur. J. Oper. Res. 106 (1998): 599-623.
Patronov et al. "Peptide binding prediction for the human class II MHC allele HLA-DP2: a molecular docking approach," BMC Struct Biol, Jul. 14, 2011 (Jul. 14, 2011), vol. 11, No. 32, pp. 1-10.
PCT/US17/64322 International Search Report and Written Opinion dated Apr. 25, 2018.
PCT/US18/00364 International Search Report and Written Opinion dated Mar. 22, 2019.
PCT/US2019/025909 International Search Report and Written Opinion dated Jun. 14, 2019.
PCT/US2019/035654 International Search Report and Written Opinion dated Nov. 25, 2019.
PCT/US2019/062482 International Search Report and Written Opinion dated Mar. 3, 2020.
PCT/US2020/030501 International Search Report and Written Opinion dated Aug. 11, 2020.
Price, et al., On silica peptide microarrays for high-resolution mapping of antibody epitopes and diverse protein-protein interactions, Nature Medicine, vol. 18, No. 9, Aug. 19, 2012, pp. 1434-1440, XP055793803, New York ISSN: 1078-8956, DOI: 10.1038/nm.2913Retrieved from the Internet:URL:http://www.nature.com/articles/nm.2913.
Reineke, et al. Epitope mapping protocols. Preface. Methods in molecular biology (Clifton, N.J.) vol. 524 (2009): v-vi.
Reyes et al. "Critical role of HLA-DR11" binding peptides' peripheral flanking residues in fully-protective malaria vaccine development," Biochem Biophys Res Commun, May 23, 2017 (May 23, 2017), vol. 489, No. 3, pp. 339-345.
Riccelli, et al. Hybridization of single-stranded DNA targets to immobilized complementary DNA probes: comparison of hairpin versus linear capture probes. Nucleic acids research vol. 29,4 (2001): 996-1004. doi:10.1093/nar/29.4.996.
Richer, et al., Epitope identification from fixed-complexity randomsequence peptide microarrays, Molecular & cellular proteomics, vol. 14, No. 1, Nov. 3, 2014, pp. 136-147.
Rothemund, et al. Folding DNA to create nanoscale shapes and patterns. Nature. Mar. 16, 2006;440(7082):297-302.
Sant'Angelo et al. "Recognition of core and flanking amino acids of MHC class II-bound peptides by the T cell receptor," Eur J Immunol, Sep. 1, 2002 (Sep. 1, 2002), vol. 32, No. 9, pp. 2510-2520.
She, et al. Comprehensive and quantitative mapping of RNAprotein interactions across a transcribed eukaryotic genome. Proc Natl Acad Sci U S A. Apr. 4, 2017; 114(14): 3619-3624.
Sjoberg et al. Validation of affinity reagents using antigen microarrays, Newbiotechnology, vol. 29, No. 5, Jun. 1, 2012 pp. 555-563, XP055793929, NLISSN: 1871-6784, DOI: 10.1016/j.nbt.2011.11.009.
Speltz, et al. Design of Protein-Peptide Interaction Modules for Assembling Supramolecular Structures in Vivo and in Vitro. ACS Chem Biol. Sep. 18, 2015;10(9):2108-15. doi: 10.1021/acschembio.5b00415. Epub Jul. 17, 2015.
Stöhr, et al. A 31-residue peptide induces aggregation of tau's microtubule-binding region in cells. Nat Chem. Sep. 2017; 9(9): 874-881. Published online Apr. 3, 2017.doi: 10.1038/nchem.2754.
Tessler, L. Digital Protein Analysis: Technologies for Protein Diagnostics and Proteomics through Single-Molecule Detection (2011). All Theses and Dissertations (ETDs). 346 https://openscholarship.wustl.edu/etd/346.
U.S. Appl. No. 16/659,132 Notice of Allowance dated Jan. 14, 2021.
U.S. Appl. No. 16/659,132 Office Action dated Oct. 8, 2020.
U.S. Appl. No. 16/788,536 Notice of Allowance dated Dec. 9, 2020.
U.S. Appl. No. 16/788,536 Office Action dated Mar. 10, 2020.
U.S. Appl. No. 16/788,536 Office Action dated Sep. 24, 2020.
U.S. Appl. No. 16/791,456 Office Action dated Jul. 6, 2021.
U.S. Appl. No. 17/062,405 Final Office Action dated Aug. 24, 2021.
U.S. Appl. No. 17/062,405 Notice of Allowance dated Sep. 30, 2021.
U.S. Appl. No. 17/062,405 Office Action dated Apr. 14, 2021.
U.S. Appl. No. 17/191,632 Examiner's Interview Summary dated Nov. 9, 2021.
U.S. Appl. No. 17/191,632 Final Office Action dated Sep. 17, 2021.
U.S. Appl. No. 17/191,632 Office Action dated May 12, 2021.
U.S. Appl. No. 16/426,917 Notice of Allowance dated Oct. 1, 2019.
Wilson, et al. Single-Step Selection of Bivalent Aptamers Validated by Comparison with SELEX Using High-Throughput Sequencing. PLoS One. 2014; 9(6): e100572.
Zandian, Arash et al. Whole-Proteome Peptide Microarrays for Profiling Autoantibody Repertoires within Multiple Sclerosis and Narcolepsy. Journal of proteome research 16(3) 2017: 1300-1314. doi:10.1021/acs.jproteome.6b00916.
Office Action in JP2021527883, mailed Oct. 24, 2023, 4 pages.
Anonymous. List of protein hydrodynamic diameters. Dynamic Biosensors. May 17, 2017, XP055857934, Available at https://www.dynamic-biosensors.com/project/list-of-protein-hydrodynamic-diameters/. Retrieved on Nov. 4, 2021.
EP19781106.0 Extended European Search Report dated Nov. 19, 2021.
Hung, Albert M., et al. Large-area spatially ordered arrays of gold nanoparticles directed by lithographically confined DNA origami. Nature nanotechnology 5.2 (2010): 121-126.

(56) References Cited

OTHER PUBLICATIONS

Rusmini, Federica et al. Protein immobilization strategies for protein biochips. Biomacromolecules vol. 8,6 (2007): 1775-89. doi:10.1021/bm061197b.
U.S. Appl. No. 16/791,456 Final Office Action dated Jan. 21, 2022.
U.S. Appl. No. 17/390,666 Office Action dated Jan. 28, 2022.
U.S. Appl. No. 16/791,456 Office Action dated Jul. 20, 2022.

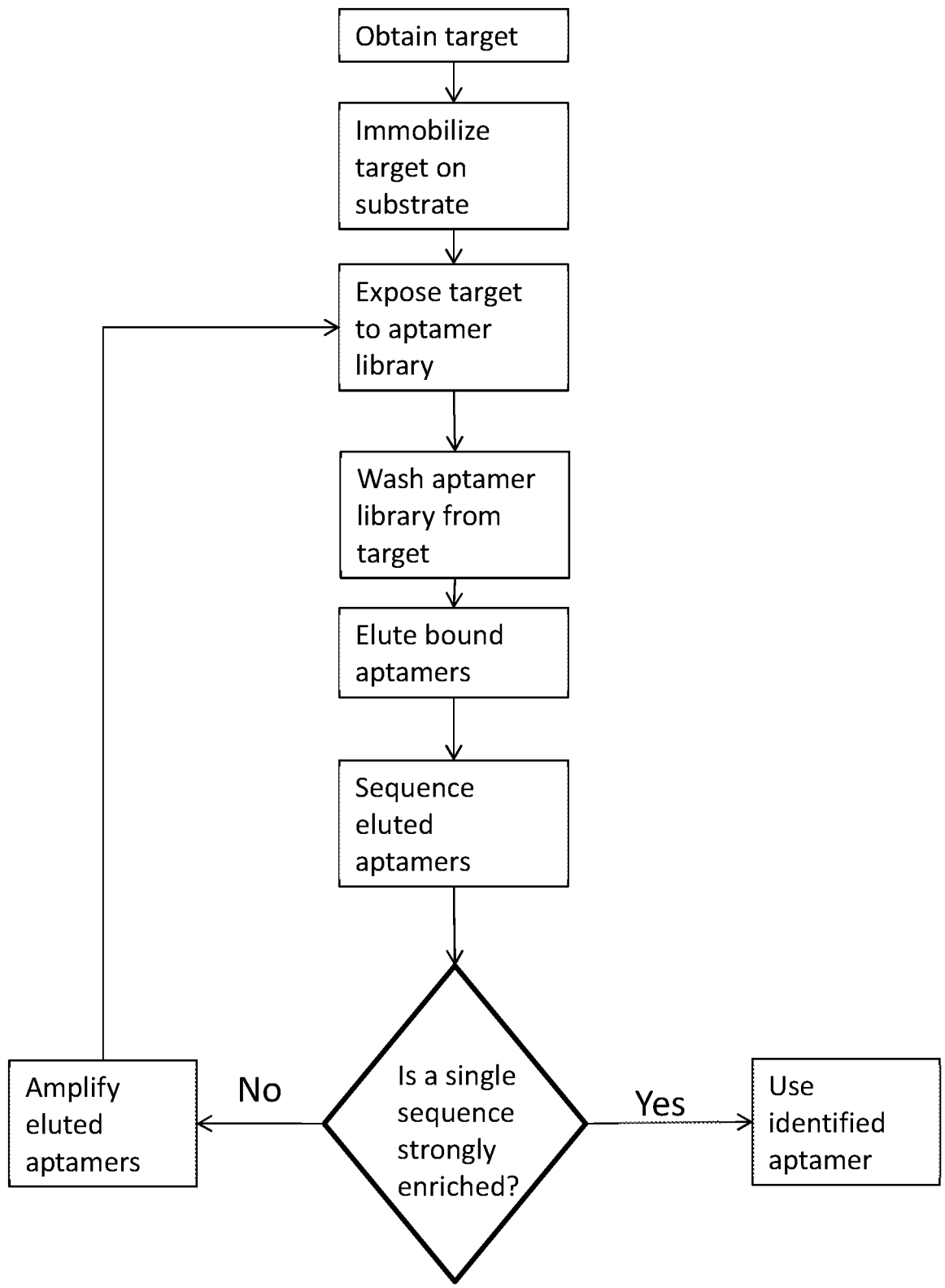

SELECTION OF AFFINITY REAGENTS

CROSS-REFERENCE

This application is a national stage entry of PCT/US2019/062482, filed Nov. 20, 2019, which claims the benefit of U.S. Provisional Application No. 62/770,136, filed Nov. 20, 2018, each of which application is incorporated herein by reference.

SEQUENCE LISTING

The instant application contains a Sequence Listing which has been submitted electronically in ASCII format and is hereby incorporated by reference in its entirety. Said ASCII copy, created on Dec. 21, 2022, is named 51612_707_831_SL.txt and is 5,532 bytes in size.

BACKGROUND OF THE INVENTION

Selection methods for the generation of binding reagents are typically designed to select for binding reagents with high affinity and specificity for a single epitope or protein. For some applications it may be useful to select binding reagents which bind multiple epitopes, or to characterize the binding patterns of binding reagents which are not specific for a single protein or epitope.

SUMMARY OF THE INVENTION

The present disclosure provides methods and systems for selecting and characterizing affinity reagents. In some embodiments, the present disclosure provides approaches in which an affinity reagent is selected to bind to an epitope in a variety of sequence contexts. Methods and systems described herein may also be used to characterize the binding pattern of an affinity reagent, and the effects of sequence context on the binding of the affinity reagent to an epitope. Additionally, methods and systems described herein may be used to characterize and select affinity reagents that bind across multiple epitopes, such as binding across multiple epitopes having a same length. By demonstrating promiscuity across multiple epitopes of a same length, a particular affinity reagent may be used in identifying sequences as containing at least one epitope of the multiple epitope to which the particular affinity reagent binds.

In an aspect, a method of identifying an affinity reagent for an epitope is provided, comprising obtaining a first peptide library comprising a first plurality of peptides, each peptide comprising a sequence of a formula $\alpha X \beta$, wherein X is the desired epitope, and wherein $\alpha$ and $\beta$ are flanking domains comprising known amino acid sequences, exposing the first peptide library to a plurality of affinity reagents, thereby binding at least one affinity reagent of the plurality of affinity reagents to the first peptide library, determining the sequence or sequences of the at least one affinity reagents bound to the first plurality of peptides, thereby forming a reduced affinity reagent pool, obtaining a second peptide library comprising a second plurality of peptides, each peptide comprising a sequence of a formula $\gamma X \delta$, wherein X is the desired epitope, and wherein $\gamma$ and $\delta$ are flanking domains comprising a known amino acid sequence, exposing the second peptide library to the reduced affinity reagent pool, thereby binding at least one affinity reagent of the reduced affinity reagent pool to the second peptide library and determining the sequence or sequences of at least one affinity reagent of the reduced affinity reagent pool bound to the second peptide library, thereby identifying an affinity reagent for the epitope X.

In some cases, $\alpha$ and $\beta$ comprise the same amino acid sequence. In some cases, $\alpha$ and $\beta$ comprise differing amino acid sequences. In some cases, $\alpha$ and $\beta$ comprise differing amino acid sequences from $\gamma$ and $\delta$. In some cases, $\alpha$ and $\beta$ comprise amino acid sequences with homogeneous chemical diversity. In some cases, the amino acid sequences with homogeneous chemical diversity comprise amino acid sequences comprising two or more amino acid side groups with equivalent electrical charge, hydrophobicity, hydrophilicity, steric size, polarity, molecular structure, or a combination thereof. In some cases, $\alpha$ and $\beta$ comprise amino acid sequences with heterogeneous chemical diversity. In some cases, the amino acid sequences with heterogeneous chemical diversity comprise amino acid sequences comprising two or more amino acid side groups with differing electrical charge, hydrophobicity, hydrophilicity, steric size, polarity, molecular structure, or a combination thereof.

In some cases, $\gamma$ and $\delta$ comprise amino acid sequences with homogeneous chemical diversity. In some cases, the amino acid sequences with homogeneous chemical diversity comprise amino acid sequences comprising two or more amino acid side groups with equivalent electrical charge, hydrophobicity, hydrophilicity, steric size, polarity, molecular structure, or a combination thereof. In some cases, $\gamma$ and $\delta$ comprise amino acid sequences with heterogeneous chemical diversity. In some cases, the amino acid sequences with heterogeneous chemical diversity comprise amino acid sequences comprising two or more amino acid side groups with differing electrical charge, hydrophobicity, hydrophilicity, steric size, polarity, molecular structure, or a combination thereof.

In some cases, the method further comprises washing the at least one affinity reagent of the plurality of affinity reagents bound to the first peptide library. In some cases, the method further comprises washing the at least one affinity reagent of the reduced affinity reagent pool bound to the second peptide library.

In some cases, the peptides within the first or second peptide library are in a native state. In some cases, the peptides within the peptide first or second library are in a non-native state. In some cases, the non-native state is a denatured state or a partially-folded state.

In some cases, the at least on affinity reagent binds with more than one epitope. In some cases, the more than one epitope comprise degenerate amino acid sequences. In some cases, the degenerate amino acid sequences differ by one amino acid. The method of claim 20, wherein the degenerate amino acid sequences differ by more than one amino acid. In some cases, the differing amino acids comprise similar chemical properties, wherein the chemical properties are selected from the group consisting of electrical charge, hydrophobicity, hydrophilicity, steric size, polarity, molecular structure, or a combination thereof. In some cases, the differing amino acids comprise dissimilar chemical properties, wherein the chemical properties are selected from the group consisting of electrical charge, hydrophobicity, hydrophilicity, steric size, polarity, molecular structure, or a combination thereof.

In some cases, the method comprises repeating one or more times the steps of exposing the first peptide library to the plurality of affinity reagents and determining the sequence or sequences of the at least one affinity reagents. In some cases, the method comprises repeating one or more times the steps of exposing the second peptide library to the reduced affinity reagent pool and determining the sequence or sequences of the at least one affinity reagents.

In some cases, an affinity reagent of the plurality of affinity reagents comprises an oligonucleotide, peptimer, mini protein binder, antibody, antibody fragment, or a combination thereof. In some cases, an affinity reagent of the plurality of affinity reagents comprises an oligonucleotide.

In another aspect, a method of identifying an affinity reagent for an epitope is provided, comprising contacting a plurality of peptides within a peptide library in a first medium with a plurality of affinity reagents within an affinity reagent pool in a second medium to form peptide-affinity reagent complexes, wherein each peptide-affinity reagent complex comprises a peptide and at least one bound affinity reagent, and wherein each peptide comprises an epitope X, collecting the peptide-affinity reagent complexes, separating unbound affinity reagents, and determining the sequence or sequences of the affinity reagents of the peptide-affinity reagent complexes, thereby identifying at least one affinity reagent for epitope X.

In some cases, the peptides within the peptide library are in a native state. In some cases, the peptides within the peptide library are in a non-native state. In some cases, the non-native state is a denatured state or a partially-folded state. In some cases, the method further comprises repeating all steps with the plurality of peptides in a native state. In some cases, the at least one affinity reagent for epitope X in the native state differs from the at least one affinity reagent for epitope X in the non-native state. In some cases, the at least one affinity reagent for epitope X in the native state is the same as the at least one affinity reagent for epitope X in the non-native state. In some cases, the epitope X binds with more than one affinity reagent.

In some cases, the at least one affinity reagent binds with more than one epitope. In some cases, the more than one epitope comprise degenerate amino acid sequences. In some cases, the degenerate amino acid sequences differ by one amino acid. In some cases, the degenerate amino acid sequences differ by more than one amino acid. In some cases, the differing amino acids comprise similar chemical properties, wherein the chemical properties are selected from the group consisting of electrical charge, hydrophobicity, hydrophilicity, steric size, polarity, molecular structure, or a combination thereof. In some cases, the differing amino acids comprise dissimilar chemical properties, wherein the chemical properties are selected from the group consisting of electrical charge, hydrophobicity, hydrophilicity, steric size, polarity, molecular structure, or a combination thereof.

In some cases, an affinity reagent of the plurality of affinity reagents comprise an oligonucleotide.

In some cases, the determining the sequence or sequences of the at least one affinity reagent bound to the plurality of peptides comprises separating the at least one affinity reagent from the plurality of peptides and sequencing the at least one affinity reagent, thereby determining the sequence or sequences of the at least one affinity reagent.

In another aspect, an affinity reagent comprising a structure of $S_1S_2S_3$ is provided, wherein $S_1$ and $S_3$ are adaptor domains capable of binding a complementary adaptor, and wherein $S_2$ is an epitope binding domain, wherein the epitope binding domain binds to the one or more peptide epitopes with a equilibrium binding constant $K_d$ of less than $10^{-6}$ M.

In some cases, the affinity reagent comprises an oligonucleotide. In some cases, the adaptor domains are next generation sequencing adaptors. In some cases, $S_1$ or $S_3$ comprises a barcode. In some cases, $S_2$ comprises no more than about 90 nucleotides. In some cases, $S_2$ comprises no more than about 60 nucleotides. In some cases, $S_2$ comprises no more than about 30 nucleotides.

In some cases, the affinity reagent binds to more than one epitope with a equilibrium binding constant $K_d$ of less than $10^{-6}$ M. In some cases, the affinity reagent binds to one or more epitopes with an equilibrium binding constant $K_d$ of less than $10^{-9}$ M. In some cases, the affinity reagent binds to one or more epitopes with an equilibrium binding constant $K_d$ of less than $10^{-12}$ M.

In some cases, the at least one affinity reagent binds with more than one epitope. In some cases, the more than one epitope comprise degenerate amino acid sequences. In some cases, the degenerate amino acid sequences differ by one amino acid. In some cases, the degenerate amino acid sequences differ by more than one amino acid. In some cases, the differing amino acids comprise similar chemical properties, wherein the chemical properties are selected from the group consisting of electrical charge, hydrophobicity, hydrophilicity, steric size, polarity, molecular structure, or a combination thereof. In some cases, the differing amino acids comprise dissimilar chemical properties, wherein the chemical properties are selected from the group consisting of electrical charge, hydrophobicity, hydrophilicity, steric size, polarity, molecular structure, or a combination thereof.

In some cases, the affinity reagent binds to one or more peptide epitopes when the peptide is in a native state. In some cases, the affinity reagent binds to one or more peptide epitopes when the peptide is in a non-native state. In some cases, the non-native state comprises a denatured state or a partially-folded state.

In another aspect, an affinity reagent pool is provided, comprising a plurality of affinity reagents, wherein two or more affinity reagents of the plurality of affinity comprise a structure $S_1S_2S_3$, wherein $S_1$ and $S_3$ comprise common adaptor domains and $S_2$ comprises an epitope binding domain, and wherein a first affinity reagent of the two or more affinity reagents comprises a first domain $S_2$ with a characterized specificity for peptide epitope $X_1$, and wherein a second affinity reagent of the two or more affinity reagents comprises a second domain $S_2$ with a characterized specificity for a peptide epitope $X_2$, wherein the first domain $S_2$ differs from the second domain $S_2$.

In another aspect, a method of identifying an affinity reagent for an epitope is provided, comprising obtaining a peptide library comprising a plurality of peptides, wherein a peptide of the plurality of peptides comprises more than one epitope X in its sequence, exposing the peptide library to an affinity reagent pool comprising a plurality of affinity reagents, thereby binding at least one affinity reagent to the peptide comprising more than one epitope X in its sequence, and determining the sequence or sequences of the at least one affinity reagent bound to the peptide comprising more than one epitope X in its sequence, thereby identifying an affinity reagent for epitope X.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 illustrates a flowchart of a process of affinity reagent selection, in accordance with some embodiments.

FIG. 5 illustrates examples of a target embedded in longer sequences with different secondary structures.

DETAILED DESCRIPTION OF THE INVENTION

Figure 1:
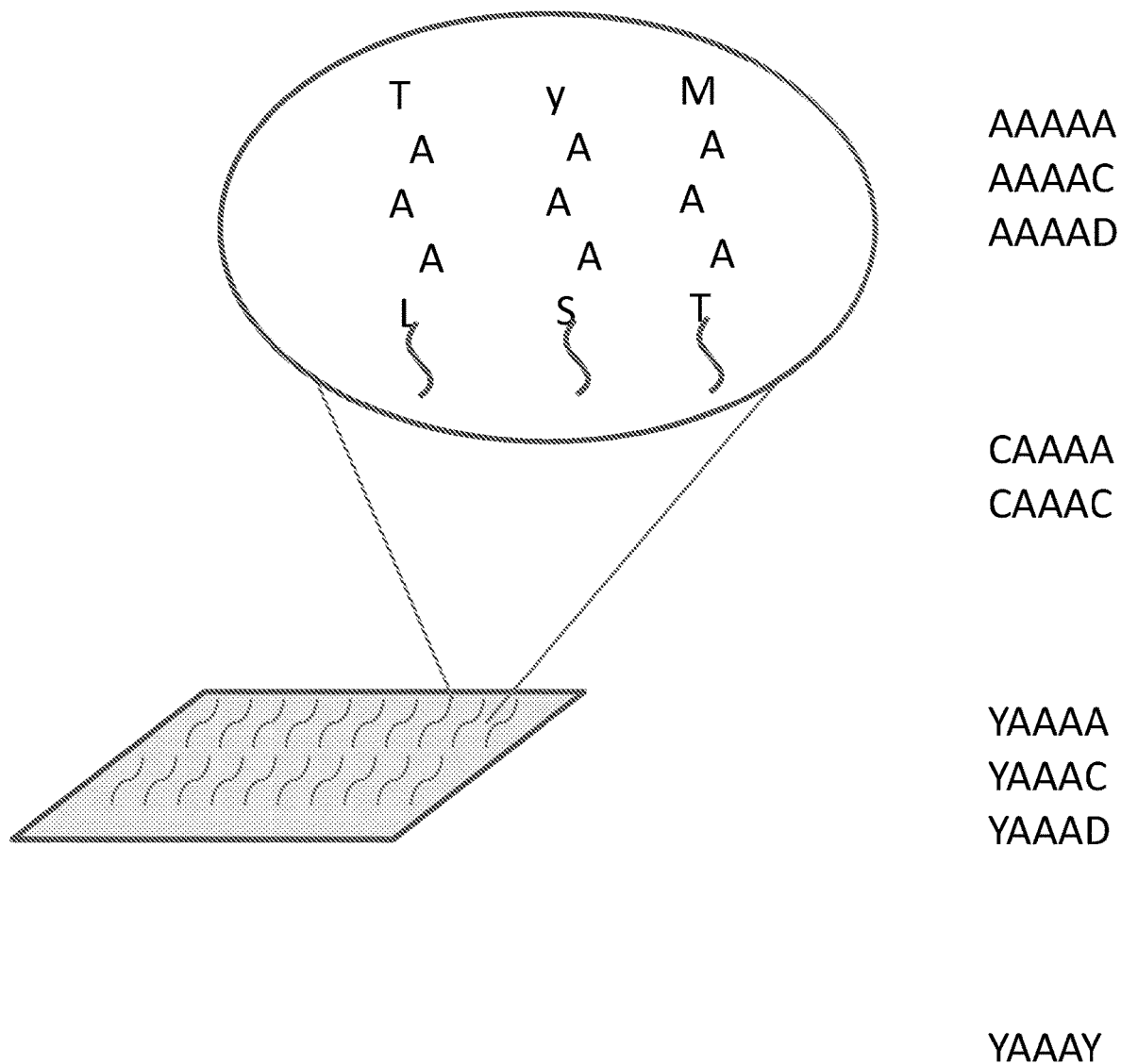
FIG. 1 illustrates an immobilized target for selection of affinity reagents, along with an exemplary list of peptides which comprise the target, in accordance with some embodiments. Figure discloses SEQ ID NOS 17-19, 2-3, 20, 4-5, and 21-24, respectively, in order of appearance.

Throughout the life sciences there has been substantial interest in the development of affinity reagents that are able to bind to specific proteins, metabolites, cells or cell interfaces. More recently, affinity reagent selection techniques have been extended to include non-natural nucleotides and amino acids. The objective of these approaches has been to develop reagents that bind exclusively to a given epitope.

Exclusivity of binding is considered to be a desirable trait in an affinity reagent. Substantial efforts are made to ensure that the affinity reagent binds to just one protein, with minimal binding to other proteins. Exceptions to this are antibodies raised against functionally important residues, such as phospho-tyrosines.

One particular challenge faced by affinity reagents may be context sensitivity. For example, affinity reagents may bind perfectly to a core epitope, but may be biased to binding well or not binding at all depending upon flanking residues. For example, when generating an affinity reagent against a peptide n-Glu-Gln-Lys-Leu-Ile-Ser-Glu-Glu-Asp-Leu (SEQ ID NO: 1), the reagent may bind better if the n-terminal residue is a Gly than if it is a Ser.

While generating affinity reagents that are not specific to any single protein may be generally undesirable, there are particular use cases in which it may be optimal to have affinity reagents that are specific to one or more peptides that may occur in many proteins.

The term 'epitope,' as used herein, may refer to a part of a macromolecule, such as a protein or peptide, which is recognized by an affinity reagent. In some cases, an epitope may be a part of a protein or peptide which is recognized by an antibody. In some cases, an epitope may be a part of a protein or peptide which is recognized by an antibody fragment. In some cases, an epitope may be a part of a protein or peptide which is recognized by an aptamer. In some cases, an epitope may be a part of a protein or peptide which is recognized by peptide.

The term 'antigenicity,' as used herein, may refer to capacity of a chemical structure (either an antigen, a hapten, an epitope or an amino acid sequence) to bind specifically with a group of certain products that have adaptive immunity, or to a class of affinity reagents. The term 'antigenicity' may be used interchangeably with the term 'aptagenicity'—the capacity of a chemical structure to be recognized by aptamers. The term 'antigenicity' may also be used interchangeably with the term 'affinity reagent-genicity' which refers to the capacity of a chemical structure to be recognized by affinity reagents generally.

The methods described herein may be used to generate affinity reagents with desired properties. For example, the methods described herein may be used to generate an aptamer, such that when the aptamer is immobilized on a particle, a peptide target remains bound to the aptamer, post-buffer wash, with a loss of less than 10% signal after approximately 15 minutes or greater. In another example, the methods described herein may be used to generate an aptamer, such that when the aptamer is immobilized on a particle, a binding signal from a bound peptide target post-buffer wash is reduced to undetectable levels in the presence of elution buffer after approximately 15 seconds or less. In another example, the methods described herein may be used to generate an aptamer, such that aptamer binding properties are preserved in the presence of a target peptide comprising a mixture of flanking amino acid residue identities. In some cases, an aptamer whose binding properties are preserved when immobilized may be desired.

Selection of Affinity Reagents

Novel affinity reagents may be generated by any method known in the art. Methods of developing affinity reagents include Systematic evolution of ligands by exponential enrichment (SELEX), phage display, yeast display, mammalian cell display, insect cell display, ribosome display, particle display, peptimer evolution, peptimer design, and inoculation. Exemplary affinity reagents may include oligomers, aptamers, peptimers, antibodies, antibody fragments, mini protein binders, synthetic molecules, and/or combinations thereof. In some examples, affinity reagents may be designed using structure-based drug design methods. Structure-based drug design (or direct drug design) utilizes knowledge of the three-dimensional structure of the epitope of interest and the binding site of the affinity reagent.

In some cases, affinity reagents of this disclosure may be chosen for an ability to bind a desired epitope regardless of the sequence context. In some embodiments, affinity reagents may be designed to bind a desired epitope when a protein is in a partially or fully denatured context. In some embodiments, the affinity reagents of this disclosure may be chosen for an ability to bind a desired epitope in a protein within a folded or unfolded context. In some embodiments, proteins that have been denatured may contain or generate microfolding within the proteins. In some embodiments, an affinity reagent chosen to recognize the desired epitope AAA may bind equally well, or nearly equally well, to all peptides containing the sequence AAA. In some cases, affinity reagents of this disclosure may be a desired epitope with different affinities according to the sequence or structural context of the epitope. In some cases, affinity reagents of this disclosure may bind several different epitopes regardless of sequence context. In some cases, affinity reagents of this disclosure may bind several different epitopes with different affinities depending on sequence context. In some cases, affinity reagents of the present disclosure may be designed to bind to a protein epitope based upon the chemical or physical properties of the epitope rather than the amino acid sequence of the epitope. For example, an affinity reagent may or may not bind to an epitope based upon localized electric charge, localized steric interactions, hydrophobicity, hydrophilicity, acidity, basicity, and any other chemical or physical properties.

The affinity reagents of the present disclosure (e.g., aptamers, peptimers, mini-protein binders, etc.) may be chosen for possessing a desired level of binding promiscuity. Binding promiscuity may refer to the ability of an affinity reagent to bind to more than one specific epitope. A non-promiscuous affinity reagent may be any affinity reagent that only has binding specificity for a single epitope. A promiscuous affinity reagent may be any affinity reagent that has binding specificity for more than one epitope. Affinity reagent promiscuity may refer to the ability of an epitope to bind to a family of epitopes. In some cases, a family of epitopes may be related by a common amino acid structure. For example, a family of epitopes may have a structure GλG, where λ may be any amino acid (e.g., GRG, GHG, GKG, GDG, etc.). In some cases, a family of epitopes may be related by a common chemical property. For example, a family of epitopes may comprise all 3 amino acid epitopes with hydrophobic side chains (e.g., AAV, AIM, WLV, etc.). In some cases, a promiscuous affinity reagent may bind to a random set of epitopes with no discernible sequence or structural motifs. In some cases, an uncharacterized promiscuous affinity reagent may bind to an unknown set of epitopes in a known or characterized set of peptides or proteins.

An affinity reagent may be promiscuous if it binds to about 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900, 1000, or more than 1000 epitopes. An affinity reagent may be promiscuous if it binds to at least about 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900, 1000, or more than 1000 epitopes. An affinity reagent may be promiscuous if it binds to no more than about 1000, 900, 800, 700, 600, 500, 450, 400, 350, 300, 250, 200, 150, 100, 90, 80, 70, 60, 50, 45, 40, 35, 30, 25, 20, 15, 10, 9, 8, 7, 6, 5, 4, 3, or less than 3 epitopes.

The binding promiscuity of an affinity reagent may be characterized in a binary or probabilistic fashion. A binary characterization of binding promiscuity may comprise assessing binding or not binding of an affinity reagent against all known epitopes (e.g., ARA—binds; AHA—binds; AKA—does not bind; ADA—binds, etc.). A probabilistic characterization of binding promiscuity may comprise assessing the likelihood of detecting affinity reagent binding to a known epitope under a particular binding condition or range of binding conditions (e.g., ARA—75% change of binding; AHA—81% chance of binding; AKA—0.05% chance of binding; ADA—61% chance of binding, etc.). An affinity reagent may be considered to bind an epitope if it is measured to have a threshold likelihood of binding the epitope. An affinity reagent may be considered to bind an epitope if it is measured to have about a 40%, 45%, 50%, 55%, 60%, 65%, 70%, 75%, 80%, 85%, 90%, 95%, 96%, 97%, 98%, 99%, 99.5%, 99.9% or higher than 99.9% chance of binding an epitope at a given condition. An affinity reagent may be considered to bind an epitope if it is measured to have at least about a 40%, 45%, 50%, 55%, 60%, 65%, 70%, 75%, 80%, 85%, 90%, 95%, 96%, 97%, 98%, 99%, 99.5%, 99.9% or higher than 99.9% chance of binding an epitope at a given condition. An affinity reagent may be considered to bind an epitope if it is measured to have no more than about a 99.9%, 99.5%, 99%, 98%, 97%, 96%, 95%, 90%, 85%, 80%, 75%, 70%, 65%, 60%, 55%, 50%, 45%, 40%, or lower than 40% chance of binding an epitope at a given condition.

In some cases, identification of such affinity reagents may be achieved through a three step screening process: 1) an initial screen for binding to a target which comprises the epitope, 2) peptide level qualification screening to characterize the binding of the affinity reagent to the epitope and/or variants of the epitope, and 3) protein level screening to confirm the binding characterization seen in step 2. In some cases, step 3 may be performed before, or partially before, step 2. In some cases, step 2 may be omitted and step 3 may be sufficient to characterize the binding of the affinity reagent. In some cases, step 3 may be omitted to determine an affinity reagent.

In some cases, the desired epitope may be a peptide. In some cases, several different epitopes may be desired, in this case an affinity reagent may be selected which binds the desired epitopes. In some cases, the desired or target epitope may comprise a family of epitopes. In some cases, the family of epitopes may comprise epitopes with degenerate sequences. For example, a family of epitopes may comprise epitopes with an amino acid sequence comprising EXE, where X is any amino acid. A family of epitopes comprising degenerate sequences may also be characterized based upon chemical properties. In some cases, a family of epitopes may comprise some or all epitopes with an overall non-neutral electrical charge (e.g., RRD, DGE), some sterically hindering amino acid side groups (e.g., WYA, FFL), polar side groups, hydrophobic side groups, hydrophilic side groups, etc. In some cases, a family of epitopes with degenerate sequences may comprise amino acid sequences with a specific ordering of chemical properties. For example, a family of epitopes may comprise any epitope comprising an amino acid sequence with, consecutively, polar side group amino acid/positively charged side group amino acid/nonpolar side group amino acid (e.g., TKG). In some cases, the desired or target epitope or family of epitopes may be referred to as X. In some cases, the epitope is a non-contiguous epitope. For example, an epitope may comprise a sequential or proximal amino acid sequence in the peptide or protein primary structure. In another example, an epitope may comprise every second amino acid residue. In another example, an epitope may comprise several amino acid residues that are located proximal to each other in a peptide or protein secondary, tertiary, or quaternary structure even though the residues are not proximal in the protein sequence or primary structure. In some cases, the epitope is a contiguous epitope. In some cases, the desired epitope, X, is a short amino acid sequence, of 2, 3, 4, 5, 6, 7, 8, 9, 10, 11, 12, 13, 14, 15, 16, 17, 18, 19, 20 or more than 20 amino acids. In some cases, the desired epitope, X, is a short amino acid sequence, of at least 2, 3, 4, 5, 6, 7, 8, 9, 10, 11, 12, 13, 14, 15, 16, 17, 18, 19, 20 or more than 20 amino acids. In some cases, the desired epitope, X, is a short amino acid sequence of no more than 20, 19, 18, 17, 16, 15, 14, 13, 12, 11, 10, 9, 8, 7, 6, 5, 4, 3, or less than 3 amino acids. In some cases, X comprises several different short amino acid sequences. In some cases, X comprises one or more non-contiguous short amino acid sequences. For example, X may comprise, for example, C—KYW, where the cysteine residue is proximal to either the lysine, tryptophan, or tyrosine in the secondary or tertiary structure of the peptide. In some embodiments, the desired epitope, X, is a three amino acid sequence, $X_1X_2X_3$. Affinity reagents which bind this desired epitope in a variety of sequence contexts may be identified by screening for affinity reagents which bind a target comprising the desired epitope.

The target may comprise peptides which include the desired sequence, X. In some cases, the target is a pool of peptides all of sequence X. In some embodiments the target may comprise a pool of peptides of sequence $\alpha X\beta$, wherein X is the desired epitope and flanking domains $\alpha$ and $\beta$ may be any sequence of zero, one, two, three, four, or more than four amino acids. For example, if the desired epitope, X, is AAA, then examples of the sequences which may be found in the target peptides may include: AAAAA (SEQ ID NO: 2), AAAAC (SEQ ID NO: 3), CAAAA (SEQ ID NO: 4), CAAAC (SEQ ID NO: 5), and CAAAD (SEQ ID NO: 6). In some cases, $\alpha$ and $\beta$ may each be any single amino acid. In some cases, at least one of flanking domains $\alpha$ and $\beta$ may be 2, 3, 4, 5, 6, 7, 8, 9, 10, or more than 10 amino acids. In some cases, at least one of $\alpha$ and $\beta$ may comprise a linker or spacer. The linkers or spacers may be any linkers or spacers known in the art. In some cases, the linker is an amino acid linker. In some cases, the linker is a polyethylene glycol (PEG) or a PEG polymer chain. The PEG chain may consist of 2, 3, 4, 5, 6, 7, 8, 9, 10, 12, 14, 16, 18, 20, 22, 24, 26, 28, 30, 34, 36, 38, 40, 42, 44, 46, 48, 50 or more than 50 PEG moieties. In some cases, the linker may be a carbon chain. In some cases, the linker or spacer may comprise a terminal tag such as a His-tag. The peptides may also comprise an N terminal or C terminal modification, for example capping. In some cases, the peptides may be modified to remove a charge, for example, terminal amidation (C-terminus) or acetylation (N-terminus). In some cases, the $\alpha X\beta$ peptide may contain nonnaturally occurring amino acids. In some cases, the $\alpha X\beta$ peptide may be modified with a linker and a functional group. For example, the molecule may be of the structure F-L-$\alpha X\beta$, where F is a functional group and L is a linker. In other cases, the molecule may be of the structure $\alpha X\beta$-L-F, where F is a functional group and L is a linker. In some cases, $\alpha$ and $\beta$ may each be the same amino acid, e.g., glycine, or may each be one or more of the same amino acids, e.g., multiple glycine residues. In some embodiments, residues may be modified to alter their aptagenicity. For example, residues may be altered by adding a positive charge; adding a negative charge; adding a hydrophobic group; modified so as to add a sugar; or other modifications so as to increase chemical diversity.

In some cases, the target may comprise peptides containing a repeating series of an epitope, e.g. XX, XXX, XXXX, etc., where X is an N-mer epitope (e.g., a 3-mer). For example, for X with a sequence KYW, a peptide may comprise a sequence of KYW, KYWKYW (SEQ ID NO: 7), KYWKYWKYW (SEQ ID NO: 8), etc. In some cases, the target may comprise a repeating series of an epitope X with flanking sequences $\alpha$ and $\beta$, e.g., $\alpha XX\beta$, $\alpha XXX\beta$, $\alpha XXXX\beta$, etc. In some cases, $\alpha$ and $\beta$ may be a single amino acid. In some cases, peptides comprising a repeating epitope X may be used as a target for initial enrichment of affinity reagents specific to epitope X from a pool of affinity reagents. After initial enrichment of affinity reagents specific to X, the remaining pool of affinity reagents may be tested a target that does not comprise a repeating sequence of epitope X. A peptide comprising a repeating sequence of a given N-mer may repeat the sequence about 2, 3, 4, 5, 6, 7, 8, 9, 10, 11, 12, 13, 14, 15, 16, 17, 18, 19, 20 or more than 20 times. A peptide comprising a repeating sequence of a given N-mer may repeat the sequence at least about 2, 3, 4, 5, 6, 7, 8, 9, 10, 11, 12, 13, 14, 15, 16, 17, 18, 19, 20 or more than 20 times. A peptide comprising a repeating sequence of a given N-mer may repeat the sequence no more than about 20, 19, 18, 17, 16, 15, 14, 13, 12, 11, 10, 9, 8, 7, 6, 5, 4, 3, or less than 3 times.

In some cases, the target may comprise a peptide containing an epitope X at several places within the peptide sequence. For example, a target may comprise a sequence $\alpha X\beta X\gamma X\delta$, where $\alpha$, $\beta$, $\gamma$ and $\delta$ are each independently spacers, spacing sequences, linkers, or linking sequences. Spacers, spacing sequences, linkers, and/or linking sequences may be different lengths. Spacing sequences or linking sequences may comprise one or more amino acid residues. Spacing sequences of linking sequences may be chosen to have little or no folding or microstructure, and/or little affinity for interacting with epitope X. Spacers or linker may comprise PEG chains or other functional groups. Spacers or linkers may be chosen to have little or no folding or microstructure, and/or little affinity for interacting with epitope X. A peptide containing an epitope X may contain epitope X in about 2, 3, 4, 5, 6, 7, 8, 9, 10, 11, 12, 13, 14, 15, 16, 17, 18, 19, 20 or more than 20 places in the peptide chain. A peptide containing an epitope X may contain epitope X in at least about 2, 3, 4, 5, 6, 7, 8, 9, 10, 11, 12, 13, 14, 15, 16, 17, 18, 19, 20 or more than 20 places in the peptide chain. A peptide containing an epitope X may contain epitope X in no more than about 20, 19, 18, 17, 16, 15, 14, 13, 12, 11, 10, 9, 8, 7, 6, 5, 4, 3, or less than 3 places in the peptide chain.

Peptides may be synthesized using any method known in the art. Several commercial platforms exist for peptide synthesis, such as the MultiPep RSi synthesizer (Intavis, Germany). Peptides may be synthesized using liquid phase or solid phase methods. Synthesized peptides may be verified using any known method for peptide analysis. For example, peptides may be verified using Mass spectrometry, Matrix Assisted Laser Desorption/Ionization Time of Flight Mass spectrometry (MALDI-TOF), Matrix Assisted Laser Desorption/Ionization, AMS (Accelerator Mass Spectrometry), Gas Chromatography-MS, Liquid Chromatography-MS, Inductively Coupled Plasma-Mass spectrometry (ICP-MS), Isotope Ratio Mass Spectrometry (IRMS), Ion Mobility Spectrometry-MS, Tandem MS, Thermal Ionization-Mass Spectrometry (TIMS), or Spark Source Mass Spectrometry (SSMS). Concentration of the synthesized peptides may also be assessed by spectroscopy. An example of a peptide synthesis reaction and verification is provided in Example 5.

FIG. 1 illustrates an immobilized target for selection of affinity reagents, along with an exemplary list of peptides which comprise the target, in accordance with some embodiments. In the example of FIG. 1 the desired epitope X has an amino acid sequence AAA, and the peptides of the target comprise sequences αAAAβ, wherein flanking domains α and β are each a single amino acid. In this example the target comprises 400 different peptides, representing each possible sequence of αAAAβ, wherein α and β are each a single amino acid. The example of FIG. 1 should not be seen as limiting possible embodiments. For example, the described target or targets could readily be configured with an epitope of more or less than three amino acids, e.g., αAAAAβ (SEQ ID NO: 9), or the target could comprise more than one amino acid, e.g., γαAAAAβδ (SEQ ID NO: 10), wherein α, β, γ and δ are each a single amino acid.

In this way, for any given N-mer epitope with flanking amino acid sequences α and β, the total number of target sequences comprising a pool may be calculated as $20^{(L_\alpha + L_\beta)}$, where $L_\alpha$ and $L_\beta$ are the integer lengths of the number of amino acids comprising α and β, respectively. For example, for a 3-mer epitope, a target comprising a pool of 5-mers may contain 400 different sequences (20 possibilities for α and 20 possibilities for β, where each of α and β are a single amino acid). In some cases, the target may comprise a pool of peptides longer than 5 amino acids in which each or both of α and β may comprise two or more amino acids. In some cases, one of α and β may comprise zero amino acids, and the other of α or β may comprise one or more amino acids. In some cases, the target may comprise a peptide of sequence X without additional amino acids. In some cases, more than 20 amino acid residues may be possible in α, X or β, e.g., non-natural or modified amino acids.

In some cases, multiple rounds of selection may be conducted with different targets selected from the pool of all sequences of the form αXβ, wherein α and β are each an amino acid sequence or a single amino acid, and X is a peptide epitope comprising an amino acid sequence comprising at least one amino acid. In some cases, αXβ may comprise a target epitope with a known degree of chemical complexity or chemical diversity. Chemical complexity or chemical diversity may include homogeneous or heterogeneous chemical complexity or chemical diversity. Chemical complexity or chemical diversity may be defined as possessing moieties, functional groups, side chains, side groups, interstitial groups, interstitial elements, or other chemical entities that produce a particular chemical property, such as electrical charge, steric size, hydrophobicity, hydrophilicity, nucleophilicity, electrophilicity, polarity, acidity, or basicity. Flanking domains α or β may comprise a homogeneous chemical complexity or chemical diversity if the amino acids sequences of α or β comprise amino acids with similar chemical properties. For example, amino acid sequences such as GAG or VIL may comprise a flanking domain sequence with homogeneous chemical complexity or chemical diversity due to the similar chemical properties of the amino acid side groups. Flanking domains α or β may comprise a heterogeneous chemical complexity or chemical diversity if the amino acids sequences of α or β comprise amino acids with dissimilar chemical properties. For example, amino acid sequences such as GEW or FRE may comprise a flanking domain sequence with heterogeneous chemical complexity or chemical diversity due to the dissimilar chemical properties of the amino acid side groups. In some cases, a target epitope αXβ may comprise a homogeneous chemical complexity or chemical diversity if the chemical complexity or chemical diversity of the flanking domains α or β are similar to the chemical complexity or chemical diversity of the amino acid sequence of X. In some cases, the chemical complexity or chemical diversity may alter the likelihood of affinity reagent binding.

In some cases, the target sequence X may be embedded in a longer sequence. For example, the target sequence X may be embedded in a 15-mer. The target sequence X may be embedded at any position within the 15-mer, for example in the case of a three amino acid target sequence X, the target sequence X may begin at position 1, 2, 3, 4, 5, 6, 7, 8, 9, 10, 11, 12, or 13 of the 15-mer. Peptides comprising embedded target sequences may be synthesized in solution, or may be synthesized on a chip, such as for example a PEPperPRINT chip or other peptide array. In some embodiments, peptides comprising embedded target sequences may be bound or synthesized onto a single molecule protein array. The longer sequence may be selected to form a secondary structure, or to lack secondary structure. Examples of such secondary structures include alpha helices, beta sheets, proline bends, turns, loops, and cysteine bridges. In some cases, the longer sequence may comprise non-naturally occurring amino acids or other groups.

In some cases, a desired or target epitope X may be decorated on a larger molecule or binding substrate such as a protein or peptide. For example, a desired or target epitope X may be attached to a larger molecule or binding substrate via a covalent or a non-covalent linker (e.g., an NHS-maleimide linker). An epitope X may be linked to a protein or peptide by binding of a linker to an amino acid side chain. An epitope X may be added to a protein or peptide by addition of the epitope to a terminal portion of the protein or peptide sequence. A protein or peptide may comprise a tail comprising multiple copies of epitope X. A larger molecule or binding substrate decorated with a desired or target epitope X may be affixed to a surface or substrate (e.g., magnetic beads, a flow cell, etc.) before or after being decorated with the epitope X.

An initial selection step may comprise screening a library of affinity reagents against a target which comprises a desired epitope. The affinity reagent library may comprise DNA, RNA, or peptide aptamers with random sequences, or with sequences similar to those of known protein binding aptamers. In some cases, the affinity reagent library will contain non-canonical or unnatural nucleotides (e.g., uracil, LNA, BNA, PNA). In some cases, an aptamer library may be a commercial library. In some cases, an aptamer library may be available from an institute, university, academic center, or research center. In some cases, a library may comprise a bead library. In some cases, an aptamer library may be generated from a library of known sequences, or from random sequences. In some cases, an aptamer library may be designed based upon results from a previous selection against a related or unrelated desired or target epitope or family of epitopes. In some cases, an aptamer library may comprise aptamers with particular structures, such as, for example, a stem loop library. In some cases, the aptamer library may comprise switchable aptamers—aptamers which can be switched between two conformations. For example, an aptamer may require a metal ion cofactor to form a first conformation, adding a chelating agent such as EDTA, or EGTA, sequesters the metal ions and causes the aptamer to adapt a different conformation. Other factors that may be used to induce aptamer switching include light, pH, temperature, solution ionic strength, magnetic fields, and electrical current.

In some cases, an aptamer may comprise an oligonucleotide. In some cases, an aptamer may comprise more than one oligonucleotide. An aptamer may comprise an oligonucleotide with a length of about 5, 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more than 100 nucleotides. An aptamer may comprise an oligonucleotide with a length of at least about 5, 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more than 100 nucleotides. An aptamer may comprise an oligonucleotide with a length of no more than about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 5 or less than 5 nucleotides.

An aptamer may comprise various regions, portions or components such as binding regions, non-binding regions, adaptors, barcodes, and labeled regions. An aptamer region, portion or component may comprise an oligonucleotide with a length of about 5, 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more than 100 nucleotides. An aptamer region, portion or component may comprise an oligonucleotide with a length of at least about 5, 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more than 100 nucleotides. An aptamer region, portion or component may comprise an oligonucleotide with a length of no more than about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 5 or less than 5 nucleotides.

In some cases, an aptamer library may comprise random sequences. In some cases, an aptamer library may comprise a rationally designed library. In some cases, an aptamer library may comprise random sequences, or rationally designed sequences, as well as constant regions which are present on all aptamers of the library. In some cases, an aptamer of the library may comprise a sequence $S_1S_2S_3$, wherein $S_1$ and $S_3$ comprise constant sequences common to all aptamers in the library, and $S_2$ is a variable sequence which may be unique to each aptamer. In some cases, an aptamer library may be designed such that all aptamers comprise the sequence $S_1S_2S_3$, wherein $S_1$ and $S_3$ comprise adapters suitable for a next generation sequencing reaction. For example, $S_1$ and $S_3$ may comprise Illumina adapters such that the aptamers of the library may be used directly in an Illumina sequencing reaction without further modification. For example, $S_1$ may contain the sequence 5'-CAAGCAGAAGACGGCATACGAGAT-3' (SEQ ID NO: 11) or $S_3$ may contain the sequence 5'-GTGTAGATCTCGGTGGTCGCCGTATCATT-3' (SEQ ID NO: 12). In some cases, $S_3$ may be at the 3' end of the aptamer, and $S_3$ may not comprise an adapter for sequencing. In such cases, $S_3$ may be of minimal length to allow an adapter to be added, but once the adapter is added the $S_3$-adapter sequence may comprise a restriction site such that the adapter can be removed leaving the $S_3$ sequence.

In some cases, at least one of $S_1$ and $S_3$ may also comprise a barcode. The barcode may be unique to a selection target, a selection condition, an experimental date, a library of origin, or a well of a multiwell plate. In some cases, a barcode may be unique to a well of a multiwell plate, such that multiple different selection experiments may be conducted in a multiwell plate, and cross well contamination may be assessed by sequencing the barcodes of aptamers in each well.

The screening of an aptamer library against the target may be performed by any method known in the art. In one aspect, the target may be immobilized on a solid support and the aptamers may be added under conditions that allow binding of aptamers with low specificity. Unbound aptamers may be washed from the target with a series of washes of increasing stringency. A screening method may comprise about 1, 2, 3, 4, 5, 6, 7, 8, 9, 10 or more than 10 wash steps per enrichment cycle. A screening method may comprise at least about 1, 2, 3, 4, 5, 6, 7, 8, 9, 10 or more than 10 wash steps per enrichment cycle. A screening method may comprise no more than about 10, 9, 8, 7, 6, 5, 4, 3, 2, or less than 2 washes per enrichment cycle. Aptamers that remain bound to the target through the wash steps may be sequenced and amplified for further rounds of selection, or used for the design of additional aptamers with high sequence similarity. Several rounds of target binding, washing, sequencing and amplification, or design of new aptamers, may be repeated until aptamers of desired specificity and binding affinity are generated. An aptamer library may also be screened using a bead-based approach utilizing beads which each comprise multiple copies of an aptamer. An aptamer library may also be screened using an array-based approach, for example by spotting multiple copies of each aptamer of the library onto an array and then assessing the spots to which the target binds. An aptamer library may also be screened using a particle display approach. In some embodiments, an aptamer library may be screened using a single molecule protein array.

Affinity reagents may be exposed to a target pool in any conceivable configuration. In a first case, a target pool may be immobilized to a substrate, wherein affinity reagents may be subsequently exposed to the target pool to measure binding. In a second case, an affinity reagent pool may be immobilized to a substrate, wherein protein targets may be subsequently exposed to the affinity reagent pool to measure binding. In a third case, targets and affinity reagents may be contacted while free in solution and then immobilized to a substrate to measure binding. In a first embodiment of the third case, affinity reagents and peptides may be contacted in solution for a period of time, then immobilized to a target such that the peptide is linked or bound to the substrate. After immobilization of the protein, affinity reagents may be unbound from the peptides by an elution step and subsequently captured for sequencing and/or amplification. In a second embodiment of the third case, affinity reagents and peptides may be contacted in solution for a period of time, then immobilized to a target such that the affinity reagent is linked or bound to the substrate. After immobilization of the affinity reagents, proteins may be unbound from the affinity reagents by an elution step. Immobilized affinity reagents may be subsequently released from the substrate for sequencing and/or amplification. Methods of contacting affinity reagents with targets pools may involve one or more rinse, wash, or separation steps to remove any unbound or weakly-bound affinity reagents or peptides before binding is measured. In some cases, peptides bound to a substrate may be released or eluted from the substrate prior to elution of the affinity reagent from the substrate.

In some cases, the percentage of the target pool to which an identified affinity reagent binds may be measured, for example by comparing the number of bound copies of the affinity reagent with the number of target peptides available for binding. In some embodiments, an affinity reagent may bind to about 0.00001%, 0.0001%, 0.001%, 0.01%, 0.1%, 1%, 10%, 20%, 30%, 40%, 50%, 60%, 70%, 80% or more than 80% of the peptides comprising the target. In some embodiments, an affinity reagent may bind to at least about 0.00001%, 0.0001%, 0.001%, 0.01%, 0.1%, 1%, 10%, 20%, 30%, 40%, 50%, 60%, 70%, 80% or more than 80% of the peptides comprising the target. In some embodiments, an affinity reagent may bind to no more than about 80%, 70%, 60%, 50%, 40%, 30%, 20%, 10%, 1%, 0.1%, 0.01%, 0.001%, 0.0001%, 0.00001%, 0.000001% or less than 0.000001% of the peptides comprising the target. Additionally, once a particular affinity reagent is identified and selected, the affinity reagent may be validated. In some embodiments, a selected affinity reagent may be validated against a plurality of sequences containing epitopes to which the affinity reagent is characterized as binding to. In some embodiments, a selected affinity reagent may be validated by assessing the selected affinity reagent against a plurality of peptide or protein sequences on a single molecule array.

In some cases, the percentage of an affinity reagent pool that binds to a desired or target epitope may be measured, for example by comparing the number of unique detected affinity reagent sequences against the known pool of sequences. In some embodiments, an epitope or family of epitopes may bind to about 0.000000001%, 0.00000001%, 0.0000001%, 0.000001%, 0.00001%, 0.0001%, 0.001%, 0.01%, 0.1%, 1%, 10%, 20%, 30%, 40%, 50%, 60%, 70%, 80% or more than 80% of an affinity reagent pool. In some embodiments, an epitope or family of epitopes may bind to at least about 0.000000001%, 0.00000001%, 0.0000001%, 0.000001%, 0.00001%, 0.0001%, 0.001%, 0.01%, 0.1%, 0.00001%, 0.0001%, 0.001%, 0.01%, 0.1%, 1%, 10%, 20%, 30%, 40%, 50%, 60%, 70%, 80% or more than 80% of an affinity reagent pool. In some embodiments, an epitope or family of epitopes may bind to no more than about 80%, 70%, 60%, 50%, 40%, 30%, 20%, 10%, 1%, 0.1%, 0.01%, 0.001%, 0.0001%, 0.00001%, 0.000001% or less than 0.000001% of an affinity reagent pool.

FIG. 2 illustrates a flowchart of a process of affinity reagent selection, in accordance with some embodiments. First, a target is obtained and immobilized on a solid support. The target is then exposed to a library of affinity reagents. In this example, the affinity reagents are aptamers. Unbound aptamers is washed from the target, and the remaining aptamers are eluted. In some cases, the eluted aptamers may be amplified using PCR, and then the antisense strands may be removed to regenerate ssDNA aptamers. In some cases, the eluted aptamers may be amplified using a biotin labeled reverse primer so that the antisense strands may be removed using streptavidin labeled beads. In some cases, the eluted aptamers may be amplified using a phosphorylated reverse primer so that the antisense strands may be removed using lambda exonuclease. In some cases, either an aliquot of the eluted aptamers, or an aliquot of the amplified and regenerated aptamers may be used in a pooled assay to determine total target binding. As rounds of selection progress towards an optimized pool, the target binding of the eluted aptamer pool, or the amplified and regenerated aptamer pool, should increase with initial rounds of selection. In some cases, excessive rounds of selection may result in decreased binding. Binding of the aptamers to the target may be measured using any method known in the art. For example, binding of the aptamers to the target may be measured by an ELISA assay, ELONA assay, dot blot assay, surface plasmon resonance, biolayer interferometry, or MicroScale Thermophoresis. In some cases, the eluted aptamers may be sequenced in a manner which preserves the aptamers, or an aliquot of the eluted aptamers may be sequenced. In some embodiments of the process, sequencing results may be used to predict whether a single aptamer, or small group of aptamers, is highly enriched, indicating strong binding, and should be selected for further screening, or whether many different aptamers show mild enrichment in which case the eluted aptamers may be amplified and reapplied to the target. These steps may be repeated until an aptamer with desired binding affinity is produced. The stringency of the wash step may be increased in subsequent wash steps. The length of the wash step may be selected to obtain affinity reagents with slow off-rates. The composition of the solution used in the elution step may be optimized to select for aptamers that rapidly unbind from the target, for example the solution used in the elution step may result in a change in pH or concentration of free ions.

The methods of the present disclosure may utilize one or more buffers, solutions or mixtures for characterizing the binding strength and/or binding specificity of an affinity reagent for a target. The buffers, solutions or mixtures may be utilized for storage, conditioning the peptide or protein targets (e.g., denaturing buffers), for washing unbound or weakly-bound affinity reagents, for binding the affinity reagent to the target, for eluting bound proteins from a substrate, or for eluting bound affinity reagents from a peptide. In some cases, buffers, solutions or mixtures may be aqueous or non-aqueous. A buffer, solution, or mixture may comprise common reagents such as Tris, phosphate buffer, or saline solution. Buffers or solutions may comprise other reagents such as salts (e.g., NaCl, KCl, $MgCl_2$), detergents, chaotropes, chelating agents or surfactants. Exemplary buffer additives may include Tween-20, Triton X-100, sodium dodecyl sulfate, acetonitrile, cholate, deoxycholate, digitonin, CHAPS, urea, guanidinium chloride, EDTA, and EGTA. A buffer or solution may be chosen to alter the physical or chemical properties of a target. For example, a buffer or solution may be chosen with sufficient acid or base strength so as to protonate and amino acid side chain amine group (e.g., histidine, arginine, lysine, serine, threonine, asparagine, glutamine, tryptophan) or deprotonate an amino acid side chain carboxylic acid group (e.g., aspartic acid, glutamic acid). A buffer or solution may alter the secondary or tertiary structure of a target without denaturing the protein. For example, a buffer or solution may cause a conformation change that exposes an epitope that was previously not exposed to the buffer or solution. A buffer or solution may oxidize or reduce portions of a protein (e.g., disulfide bridges).

In some cases, a buffer may be chosen as a selection agent for an affinity agent screening method. The properties of a buffer in an affinity reagent screening method may be chosen to increase or decrease the likelihood of affinity reagent binding. For example, buffers may be chosen with a particular ionic strength or the presence of a detergent or chaotrope. A buffer may be chosen as a selection agent due to its use in downstream assays that would utilize an affinity reagent. For example, a method of protein characterization or identification utilizing the affinity reagents of the present disclosure may require binding buffers, wash buffers or detection buffers. An affinity reagent may be selected by the methods described above and below due to having a threshold level of binding in the presence of buffers with similar or identical composition to those utilized in the protein characterization assay.

Buffers or solutions may be characterized by a particular ionic or salt strength. A buffer or solution may have an ionic or salt strength of at least about 10 µM, 50 µM, 100 µM, 250 µM, 500 µM, 750 µM, 1 mM, 5 mM, 10 mM, 25 mM, 50 mM, 100 mM, 250 mM, 500 mM, 1 M, 2 M, 5 M or more than 5 M. A buffer or solution may have an ionic or salt strength of no more than about 5 M, 2 M, 1 M, 500 mM, 200 mM, 100 mM, 50 mM, 25 mM, 10 mM, 5 mM, 1 mM, 750 µM, 500 µM, 250 µM, 100 µM, 50 µM, 10 µM, or less than 10 µM. A buffer or solution may be characterized with a particular pH. A buffer or solution may have a pH of about 1, 2, 3, 4, 5, 6, 7, 8, 9, 10, 11, 12, or 13. A buffer or solution may have a pH of at least about 1, 2, 3, 4, 5, 6, 7, 8, 9, 10, 11, 12, 13, or more than 13. A buffer or solution may have a pH of no more than about 13, 12, 11, 10, 9, 8, 7, 6, 5, 4, 3, 2, 1 or less than 1. A buffer may comprise a component such as a salt, detergent, chaotrope, or surfactant in an amount of at least about 0.01 wt %, 0.05 wt %, 0.1 wt %, 0.5 wt %, 1 wt %, 2 wt %, 5 wt %, 10 wt % or more than 10 wt %. A buffer may comprise a component such as a salt, detergent, chaotrope, or surfactant in an amount of no more than about 10 wt %, 5 wt %, 2 wt %, 1 wt %, 0.5 wt %, 0.1 wt %, 0.05 wt %, 0.01 wt % or less than 0.01 wt %.

Buffers, solutions or mixtures of the present disclosure may be provided at a particular temperature or heated and/or cooled to a particular temperature during an assay or process. The temperature of a buffer, solution or mixture may be changed to optimize a particular process, for example affinity reagent binding, washing, or affinity reagent elution. A buffer, solution or mixture may have a temperatures of about −80° C., −70° C., −60° C., −50° C., −40° C., −30° C., −20° C., −10° C., 0° C., 4° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., or more than 95° C. A buffer, solution or mixture may have a temperatures of at least about −80° C., −70° C., −60° C., −50° C., −40° C., −30° C., −20° C., −10° C., 0° C., 4° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., or more than 95° C. A buffer, solution or mixture may have a temperatures of no more than about 95° C., 90° C., 85° C., 80° C., 75° C., 70° C., 65° C., 60° C., 55° C., 50° C., 45° C., 40° C., 35° C., 30° C., 25° C., 20° C., 15° C., 10° C., 4° C., 0° C., −10° C., −20° C., −30° C., −40° C., −50° C., −60° C., −70° C., −80° C., or lower than −80° C.

A target may comprise a peptide, protein fragment of protein against which the binding of affinity reagents may be tested. Targets may be natural proteins or protein fragments. Targets may be synthesized peptides, proteins or protein fragments. Targets may be obtained, then bound or immobilized on a substrate. Targets may be synthesized directly on a substrate.

In some cases, a target may be immobilized on a bead. In some cases, a target may comprise a pool of different sequences, and may be immobilized onto beads such that each bead comprises two or more different sequences, or such that each bead comprises a single target sequence. In some cases, a target may be immobilized onto beads such that each bead comprises a target sequences from a distinct subset of all possible sequences. For example, a first bead may comprise targets of sequence G-X-G, where X is the final sequence which binding is desired against and G is glycine, and a second bead may comprise one or more targets selected from sequences comprising αXβ, wherein α and β are each a single amino acid and at least one of α and β is not glycine. In another example, a first bead may comprise targets of sequence G-X-G, where X is the final sequence which binding is desired against and G is glycine, and a second bead may comprise one or more targets selected from sequences comprising αXβ, wherein α and β are each any single amino acid. In some cases, said beads may be magnetic beads.

In some cases, a target may be immobilized to a solid support, such as a bead, using a linker. Examples of linkers include short amino acid sequences, such as GGG, AGA, or a short sequence of dextro-rotatory amino acids in contrast to levo-rotatory amino acids used for target sequence compositions. In some cases, a linker used may be a polyethylene glycol (PEG) linker. The structure of PEG is commonly expressed as H—(O—$CH_2$—$CH_2$)$_n$—OH. In some cases, a PEG linker may be selected such that the PEG linker is long enough for the immobilized target to be accessible to the affinity reagents to be screened, or selected. In some cases, a PEG linker may be selected such that the PEG linker is short enough to avoid the PEG linker folding on itself and reducing the accessibility of the target to the affinity reagents to be screened, or selected. In some cases, a PEG linker may comprise a polymer chain length of between 2 and 32, between 4 and 12, between 4 and 10, or between 4 and 8. In some cases, a PEG linker used may be PEG-2, PEG-3, PEG-4, PEG-5, PEG-6, PEG-7, PEG-8, PEG-9, PEG-10, PEG-11, PEG-12, PEG-13, PEG-14, PEG-15, PEG-16, PEG-17, or PEG-18. In some cases, a PEG linker may be PEG-4 or PEG-8.

In some cases, the density of the target on the solid support may influence the binding of the affinity reagents being selected. For example, high target density may result in cooperative binding. In some cases, the density of the target on the solid support, or the concentration of target on a support, may be optimized to promote selection of affinity reagents with desired properties. In some cases, the density of the target on the solid support, or the concentration of target on a support may be varied depending on a property of the target—for example the charge of the target. In some cases, positively charged targets may be applied to a solid support at a lower concentration than uncharged, or negatively charged targets. In some cases, positively charged targets may be applied to a solid support at a higher concentration than uncharged, or negatively charged targets.

In other aspects, the initial selection step may comprise immobilizing affinity reagents of the library onto a solid support and adding labeled targets. The solid support may be a slide, a bead, a magnetic bead, a surface within a flow cell. Affinity reagentss of the library may be immobilized as single copies, or may be immobilized in a pool. For example, multiple copies of a single affinity reagent may be immobilized on a region of a solid support, while multiple copies of other affinity reagents are immobilized on other regions of said solid support. In some cases, affinity reagents of a library may be modified with adapters and hybridized to an oligo coated solid support. For oligo-based affinity reagents, cluster amplification may then be used to locally amplify each aptamer on the solid support. In some cases, a solid support is a glass slide. In some cases, a solid support is a flow cell. In some cases, a solid support is a flow cell suitable for fluorescent imaging. In some cases, a solid support is a magnetic bead, or a plurality of magnetic beads. Each magnetic bead of a plurality of magnetic beads may be coated in multiple copies of a single, distinct, affinity reagent, such that each bead is coated with a different affinity reagent from each other bead.

In other aspects the initial selection step for an affinity reagent may comprise injecting a target into a host animal capable of producing antibodies against the target. The host animal may be any animal capable of producing antibodies, for example a rabbit, a goat, a mouse, a rat, a horse, a cow, a sheep, a camel or a donkey. Antibodies may be recovered from the serum of the host animal. Serum from the host animal may be used as is, or the antibodies may be purified from the serum. Methods of purifying antibodies include physicochemical fractionation, class-specific affinity or antigen-specific affinity. Class-specific affinity may involve binding of the antibodies to immobilized biological ligands with specific affinity to immunoglobins. Antigen-specific affinity may involve use of immobilized target to pull down antibodies which bind the target. The purified antibodies may be sequenced to identify the antibodies from the serum, identified antibodies may then be synthesized in vivo or in vitro.

In some cases, rather than extract antibodies from the serum of the immunized host animal the spleen may be extracted and spleen cells may be immortalized. One method to immortalize the spleen cells may be to fuse the cells with myeloma cells to form hybridomas. Individual clones may be isolated from the hybridoma, each of which will produce a single monoclonal antibody. The different monoclonal antibodies may be screened against the target using similar methods as above. Briefly, the target may be immobilized on a solid support and the antibodies may be added under increasingly stringent conditions to determine the antibodies which bind with desired affinity. The sequence of a selected monoclonal antibody may be derived by sequencing the protein, or by sequencing the coding sequence from the cell line which produced it.

In some cases, an antibody, fragment of an antibody, peptide, or another suitable protein scaffold with a variable region may be selected using phage display. A phage library may be obtained in which each phage expresses an antibody, fragment of an antibody, peptide, or another protein scaffold on its surface and encodes the sequence for generating that protein or peptide. The phage library may be applied to the peptide target and phages which express, and encode proteins or peptides that do not bind to the target may be washed away. Phages which express and encode proteins or peptides that bind the target may be eluted from the target. The eluted phages may be amplified by infecting cells with the phages, and the amplified phages may be used to repeat the selection step for a desired number of iterations. Succeeding iterations may utilize wash buffers with increasing stringency or increasing wash times. Once the desired number of iterations has been completed the selected phages may be analyzed, for example by lysing the phage to sequence the DNA encoding the expressed protein or peptide. This sequence may be used to construct a cell line which will express the selected protein or peptide.

In some cases, an antibody, or other affinity reagent, may be selected using bacterial, mammalian cell, insect cell or yeast display. These methods are similar to phage display described above, but a bacterial, mammalian cell, insect cell or yeast library is obtained in which each bacterium, mammalian cell, insect cell or yeast cell expresses a protein or peptide on its surface and encodes the sequence for generating that protein or peptide. The selection method is the same as that described for phage display.

The affinity reagent selection methods of the present disclosure may be utilized for any conceivable affinity reagent, including oligomers, peptimers, mini-protein binders, antibodies, antibody fragments, affinity reagents including synthetic or non-natural components (e.g., non-natural nucleotides or amino acids), and combinations thereof.

In some embodiments, affinity reagents may be selected against many different targets in parallel. For example, for aptamer affinity reagents, many different targets may be fixed to different locations on an array, and used with a SELEX selection method. In another example, many different targets may be attached to magnetic beads and used with a SELEX selection method. In some embodiments, affinity reagents may be selected against targets on a single molecule protein array.

In an embodiment, a next generation sequencing platform (e.g., Illumina, Nanopore) may be adapted for high throughput aptamer screening. In some cases, an Illumina style next generation sequencing platform may be adapted for high throughput DNA aptamer screening. In some cases, RNA-based aptamers may be screened and sequenced by reverse transcription methods. Peptide aptamers may be sequenced by any protein sequencing method. In some cases, an affinity reagent of the present disclosure may have a structure $S_1 S_2 S_3$, wherein $S_1$ and $S_3$ comprise adapters suitable for capture, detection, and/or identification of the affinity reagent. For example, a pool of aptamers eluted from a SELEX selection as described above, (wherein all aptamers in the pool comprise the sequence $S_1 S_2 S_3$, wherein $S_1$ and $S_3$ comprise adapters suitable for a next generation sequencing reaction), may be hybridized to an oligonucleotide in a flow cell. Solid state amplification may be used to create an aptamer cluster from each starting aptamer of the aptamer library. The antisense strands may be removed from the flowcell by a number of methods, for example by using an enzyme which specifically cleaves the antisense strands from the solid support. Using an aptamer library which incorporates the adapters during the SELEX stage prevents disruption of aptamer folding when the adapters are added, and ensures that the aptamers present in the flow cell are the same lengths and sequences as the output pool generated during SELEX. This maximizes the chances that the aptamers in the flowcell will fold in the same manner as they did in the SELEX stage, thus allowing comparison. In cases where the aptamers comprise an $S_3$ sequence which doesn't include the adapter sequence, but instead forms a restriction site when attached to an adapter, the amplified strands may be treated with a suitable restriction enzyme to regenerate the aptamer sequences used in the selection step. The surface of the flow cell may now be covered in a plurality of nucleic acid clusters, each one comprising many copies of a single aptamer from the aptamer library. A sequencing reaction may be run on the flow cell, using nucleic acid polymerases, primers and four different fluorescently labeled reversible terminators (A, T, C, and G). This can provide the sequence of the aptamer at each location in the flow cell. Once the identity of each aptamer cluster is known one or more detectably labeled peptide targets may be added to the flow cell and incubated with the aptamer clusters. After a period of incubation unbound targets are washed off and the flow cell is imaged to determine the locations where targets are bound. As multiple phases of incubation and wash steps are performed, $k_a$, $k_d$, and $K_D$ values may be generated. In particular, after an initial wash step to remove unbound targets, an initial image may be taken to identify which bound targets are still present. After the initial image is taken, a second wash step may be performed to remove targets that have become unbound during the elapsed time and a second image may then be taken. This process may be iterated over a plurality of stages so as to calculate binding properties across a number of targets based on the times at which they become unbound. In some instances, an initial wash step may be followed immediately by a second wash step. Determinations of binding properties may also be performed using techniques including, for example, surface plasmon resonance or biolayer interferometry (BLI) techniques.

In some cases, many different targets with different, resolvable, labels may be added to the flow cell to perform multiple parallel selections. An example of this method is provided in Example 4.

In some cases, high throughput aptamer screening using an Illumina style flow cell as described above may reduce the number of SELEX selection rounds required to identify an aptamer with desired binding properties. In some cases, an aptamer with desired binding properties may be identified after only 1, 2, 3, 4, 5, 6, or 7 rounds of SELEX selection. In some cases, no SELEX rounds will be required because a rationally designed library may be screened in its entirety using an Illumina style flow cell.

In some embodiments, the ease of affinity reagent selection may be affected by the sequence/structure of the epitope. Epitopes with high 'immunogenicity', 'antigenicity', 'aptamergenicity' or 'affinity reagent-genicity' may be easier to design affinity reagents against. For example, epitopes containing amino acid residues with very different chemical properties or a diversity of chemical properties (e.g., side group charge, side group steric size, side group hydrophobicity, side group pKa, side group polarity) may be easier to select affinity reagents for. Epitopes such as GGG or AAA may be harder to select affinity reagents against than epitopes such as KWK or DCY. In some embodiments, epitopes may be modified, such as using chemical bioconjugation, so as to identify affinity reagents to interact with the modified epitopes. Amino acids K, R, D, E, Y, W, and C, in particular, are readily modified. In some embodiments, when identifying an affinity reagent to bind to a desired epitope of, it may be beneficial to modify DYW with a chemical reaction that adds a component that is easier to identify using an affinity reagent. In particular, DYW may be modified to add a positive charge or nucleic acid which may then have an affinity reagent tailored to that component. In this way, the DYW epitope may be easier to stand out. Further, when running a platform to identify a desired epitope that has been modified, a protein sample (such as a blood sample) may be exposed to a chemical reaction that will modify a DYW epitope in an expected and particular way, which may then allow the protein to be assessed against a particular affinity reagent to determine whether the unmodified DYW epitope corresponding to the modified DYW epitope having a positive charge or nucleic acid component was present in the original protein sample. In some embodiments, the chemical reaction to the DYW epitope may be reversible. In some embodiments, the chemical reaction to the DYW epitope may be irreversible. In this way, tailored assays may be run to identify the modified DYW epitope.

In some cases, a collection of potential targets may be stratified into different groups based on the predicted 'antigenicity' or 'affinity reagent-genicity' of the target epitopes. For example, in some cases combining both high antigenicity targets and low antigenicity targets into a single parallel selection step may result in the affinity reagents against the high antigenicity targets swamping out signals from affinity reagents against the low antigenicity targets. Predicted antigenicity may be based on the chemical properties of the amino acid residues in the targets, with charged, and larger, amino acids being expected to have higher antigenicity. Targets which contain two or more same or chemically similar amino acid residues may have lower antigenicity than targets which contain amino acid residues with very different chemical properties. In some cases, the antigenicity of different targets may be determined experimentally, based on the results of initially affinity reagent selection screens.

In some cases, a library of affinity reagents or an affinity reagent may be placed through a negative selection screening method. The purpose of a negative selection screening method may be to identify affinity reagents that do not demonstrate a threshold degree of binding to undesired epitopes, surfaces, materials, or combinations thereof. In some cases, a negative selection screen may identify affinity reagents that do not bind to a substrate material (e.g., glass, polymer beads, fluidic tubing). In some cases, a negative selection screen may identify affinity reagents that do not bind non-specifically to peptides or proteins. For example, an affinity reagent may not be selected if it is found to bind to at least about 10%, 20%, 30%, 40%, 50%, 60%, 70%, 80%, 90% or more of all peptides or proteins in a random library (e.g., a library comprising native proteins from a biological sample). In some cases, an affinity reagent may be identified in a negative selection screen before its epitope specificity is characterized. In other cases, an affinity reagent may be characterized for its epitope specificity and then verified by a negative selection screen.

A negative selection screen may involve the steps of a) contacting an affinity reagent in a medium with one or more materials or substrates, b) collecting unbound affinity reagents from the medium after the contacting, c) sequencing the unbound affinity reagents, d) collecting bound affinity reagents from the one or more materials or substrates, e) sequencing the bound affinity reagents, and f) comparing the sequences of bound and unbound affinity reagents to determine which affinity reagents had no or minimal affinity for the tested materials or substrates. The collecting of bound affinity reagents from the materials or substrates may involve one or more eluting washes or rinses.

Characterization Screening of Affinity Reagents

A peptide characterization or qualification screen may be performed on any affinity reagent identified as binding the target. The affinity reagent may have been identified in a screen as described above, or may have been obtained through any method known in the art. In some embodiments, a secondary characterization screen may be used to determine the binding affinity or specificity of the affinity reagent to a desired epitope over other possible sequences. For the secondary screen, a library of possible N-mer sequences may be used to determine if the affinity reagent recognizes other sequences. In some cases, the library comprises at least 80%, 85%, 90%, 95%, 96%, 97%, 98%, 99%, 99.9%, or more than 99.9% of all possible N-mer sequences. In some cases, the library comprises all possible N-mer sequences. If the affinity reagent is believed to bind a 3-mer, then the other sequences may be selected to represent all possible 3-mers ($20^3$=8000). In some embodiments, the sequences that are selected to represent the possible epitopes of interest may be embedded within other sequences, such as flanking sequences. In some embodiments, the sequences that are selected to represent the desired epitopes may have a flanking sequence, or a chemical linker, added to the side of the desired epitope that attaches to a solid substrate so that the desired epitope is in a position far enough from the solid substrate so as to allow the affinity reagent to access the desired epitope. If the affinity reagent is believed to bind a 4-mer then the other sequences may be selected to represent all possible 4-mers ($20^4$=160,000). In one embodiment the pool of different N-mers may be immobilized in different wells of a multiwell plate, or on different regions of a solid support. The affinity reagent may then be incubated with the library and unbound affinity reagent is gently washed off. Regions where the affinity reagent has bound to the library may be detected by any method suitable for visualizing the affinity reagent. In some examples, the affinity reagent may be visualized by a dye or reagent which binds to proteins and/or nucleic acids, or the affinity reagents may be labeled with a detectable moiety prior to addition to the library. In some cases, binding of the affinity reagent to the target may be detected by Fluorescence Resonance Energy Transfer (FRET) Microscopy, Surface Plasmon Resonance (SPR), Bioluminescence Resonance Energy Transfer (BRET), NanoBRET, or Bio-layer Interferometry (BLI).

In some cases, presence or absence of the affinity reagent may be determined under several different conditions—for example different stringencies of washing, which may be achieved, for example, by using different washing buffers, different times of washing, different washing temperatures, or different levels of agitation. In some cases, the binding of the affinity reagent may be measured repeatedly over time to generate a time course of binding. In some cases, determining the binding of the affinity reagent under different conditions and/or at different times may enable estimation of the $K_D$, $k_a$ or $k_d$ of the affinity reagent for the target. The binding of an affinity reagent or a pool of affinity reagents may be measured for a time period of about 1 second (s), 30 s, 1 minute (min), 2 mins, 3 mins, 5 mins, 10 mins, 15 mins, 20 mins, 30 mins, 45 mins, 1 hour (hr), 2 hrs, 3 hrs, 6 hrs, 12 hrs, or more than 12 hrs. The binding of an affinity reagent or a pool of affinity reagents may be measured for a time period of at least about 1 s, 30 s, 1 min, 2 mins, 3 mins, 5 mins, 10 mins, 15 mins, 20 mins, 30 mins, 45 mins, 1 hour (hr), 2 hrs, 3 hrs, 6 hrs, 12 hrs, or more than 12 hrs. The binding of an affinity reagent or a pool of affinity reagents may be measured for a time period of no more than about 12 hrs, 6 hrs, 3 hrs, 2 hrs, 1 hr, 45 mins, 30 mins, 20 mins, 15 mins, 10 mins, 5 mins, 3 mins, 2 mins, 1 min, 30 s, 1 s, or less than 1 s. The binding of an affinity reagent or a pool of affinity reagents may be measured at intervals over a time period. The time intervals may be regular, patterned, or random. Binding of an affinity reagent or pool of affinity reagents may be measured on an interval of about 1 s, 5 s, 10 s, 15 s, 30 s, 1 min, 5 mins, 10 mins, 15 mins, 30 mins, 1 hr, 2 hrs, 3 hrs, 6 hrs, or more than 6 hrs. Binding of an affinity reagent or pool of affinity reagents may be measured on an interval of at least about 1 s, 5 s, 10 s, 15 s, 30 s, 1 min, 5 mins, 10 mins, 15 mins, 30 mins, 1 hr, 2 hrs, 3 hrs, 6 hrs, or more than 6 hrs. Binding of an affinity reagent or pool of affinity reagents may be measured on an interval of no more than about 6 hrs, 3 hrs, 2 hrs, 1 hr, 30 ins, 15 mins, 10 mins, 5 mins, 1 min, 30 s, 15 s, 10 s, 5 s, 1 s, or less than 1 s.

In some embodiments, different washing and detecting conditions may be used to identify affinity reagents with desired properties, such as, for example desired on rates and off rates, or equilibrium association constants ($k_a$) and disassociation constants ($k_d$). In some cases, desired affinity reagents may have slow off rates. Equilibrium of an affinity reagent epitope binding reaction is reached when:

$$[\text{affinity reagent}] \cdot [\text{epitope}] \cdot k_a = [\text{affinity reagent-epitope}] \cdot k_d.$$

In some cases, preferred affinity reagents may have a $k_d$ value that is less than about 1 $s^{-1}$, $10^{-1}$ $s^{-1}$, $10^{-2}$ $s^{-1}$, $10^{-3}$ $s^{-1}$, $10^{-4}$ $s^{-1}$, $10^{-5}$ $s^{-1}$, $10^{-6}$ $s^{-1}$, $10^{-7}$ $s^{-1}$, $10^{-8}$ $s^{-1}$, $10^{-9}$ $s^{-1}$, or $10^{-10}$ $s^{-1}$. In some cases, the off rate may be more critical than the on rate as a poor on rate may be compensated for by increasing the amount of affinity reagent added to a reaction, or by increasing the incubation time before washing. In some cases, the affinity reagents are selected such that the off rate is sufficient to enable the affinity reagent to remain bound through one or more washing steps, and until after an imaging step has been completed. In some cases, an affinity reagent may remain bound to an epitope for at least about 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 25 min, 30 min, 35 min, 40 min, 45 min, 50 min, 55 min, 60 min, or more than about 60 min.

In some cases, a preferred affinity reagent only binds to one of the N-mers (e.g., 3-mers) in the library. In other cases, a preferred affinity reagent may bind to 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100 or more than 100 different N-mers. In some embodiments, the step of washing off the affinity reagents may be repeated with increasing stringencies and the affinity reagents which remain bound may be detected after each washing step. In some cases, the preferred affinity reagent binds to an N-mer flanked by any amino acid residues. In some cases, the preferred affinity reagent binds to an N-mer (e.g., a 3-mer) flanked by a subset of all possible amino acid residues. In some cases, an affinity agent selected against a particular target epitope or family of epitopes may be characterized to also bind against epitopes that differ from the target epitope or family of epitopes. For example, an affinity reagent may be identified for a target epitope with a sequence AXA where X may comprise any amino acid. Subsequent characterization of the affinity reagent against AXA may also identify binding to epitopes RSR, FFW, and YIC. In some cases, a promiscuous affinity reagent with binding to epitopes outside its target epitope family may still be a valuable affinity reagent for identifying peptide epitopes provided the specific promiscuous epitopes are known.

In another method, an identified affinity reagent against a desired or target epitope or family of epitopes may be modified or matured to generate a new target library. In some cases, modification or maturing of the affinity reagent may comprise creating libraries of single- or multiple-nucleotide substitutions in the binding region sequence of the identified affinity reagent. In other cases, modification or maturing of the affinity reagent may comprise substituting one or more non-natural nucleotides or other chemical modifications to create a library of modified affinity reagents against the same epitope. Modified or matured affinity reagent libraries may be tested against the desired or target epitope or family of epitopes to identify affinity reagents with differing binding affinities, for example stronger binding or differing promiscuity for epitopes outside the target family of epitopes.

In another method, the affinity reagents may be immobilized on a solid support and the pool of all possible N-mers may be added to the affinity reagents, unbound N-mers may be removed by washing and the remaining N-mers may be analyzed to find the sequences bound by the affinity reagents. Repeated screening steps may be performed with washing steps of differing stringency. The bound N-mers may be identified using any suitable method, for example mass spectrometry or high performance liquid chromatography mass spectrometry. In some cases, a pool of random N-mers may be used rather than the pool of all possible N-mers. In cases where a pool of random N-mers was used for the characterization screen, both the bound and unbound N-mers may be identified. Sequences which were not represented in either the bound or unbound N-mer pools may be noted for follow up in subsequent characterization screens. In some cases, the pool of random N-mers may be characterized before applying to the affinity reagent to ensure that the pool includes at least 70%, 75%, 80%, 85%, 90%, 95%, 96%, 97%, 98%, 99% or more than 99% of possible N-mer sequences. In some cases, a preliminary characterization screen may be performed with random N-mers and affinity reagents which bind less than about 30, 25, 20, 15, 10 or 5 N-mers may be selected for further characterization using a pool of all possible N-mers.

A further peptide qualification screen may be performed to determine whether the affinity reagent binds specifically to the desired epitope or whether the affinity reagent is binding to a subpart of the epitope. For example, an affinity reagent believed to be specific for the 3-mer sequence AKD may actually be specific for the dimer sequence AK. Thus for each N-mer affinity reagent a screening step may be performed against the set of all (N−1)-mers. In some cases, where a characterization screen has been performed and the set of all N-mers bound by the affinity reagent is known, the screen may be limited to merely the (N−1)-mers which are contained within the N-mers which are bound by the affinity reagent. For example, if the only 4-mer bound by the affinity reagent is AAKD (SEQ ID NO: 13) then a screen may be performed against AAK and AKD, rather than all possible 3-mers. If an affinity reagent does bind to a (N−1)-mer then an additional screen against (N−2)-mers may be performed to further define the specificity of the affinity reagent. In some cases, affinity reagents which bind to (N−1)-mers may not be selected for further screening. In other cases an affinity reagent which binds to no more than one of the (N−1)-mers may be selected. In other cases, affinity reagents which bind to more than one (N−1)-mers may be retained for further screening.

An additional peptide qualification screen may be performed to determine the effect of flanking sequences on the affinity reagent's affinity for its epitope or epitopes. For this step a library of peptides of the sequence $\alpha X \beta$, (wherein X is the affinity reagents epitope, or epitopes, and $\alpha$ and $\beta$ may be any one or more amino acids), may be created. In the example of an affinity reagent which binds to a single epitope, and given a case wherein $\alpha$ and $\beta$ are each a single amino acid, given that the sequence of the bound epitope is set, there are 400 possible $\alpha X \beta$ sequences regardless of the length of the desired epitope. For cases where the affinity reagent binds two or more different epitopes, or where $\alpha$ and $\beta$ may each be none, one, or more than one amino acids, there may be many possible sequences of $\alpha X \beta$. In some cases, the set of $\alpha X \beta$ peptides used in this screening step may be the same set of $\alpha X \beta$ peptides which comprised the target used for the selection of the affinity reagent. The affinity reagent may be screened against the set of $\alpha X \beta$ sequences using standard screening methods. Reviewing the list of $\alpha X \beta$ sequences to which the affinity reagent binds, as well as the relative binding affinities, may allow a determination of the effects of the flanking sequence on the binding affinity of the affinity reagent. If strong effects are seen then a further screen may be performed with longer flanking sequences, for example if a first library of sequences consisted of peptides $\alpha X \beta$ wherein $\alpha$ and $\beta$ where each a single amino acid then a subsequent screen may be performed with a library of peptides consisting of $\gamma X \delta$, wherein $\gamma$ and $\delta$ each comprise two amino acids.

Figure 3A:
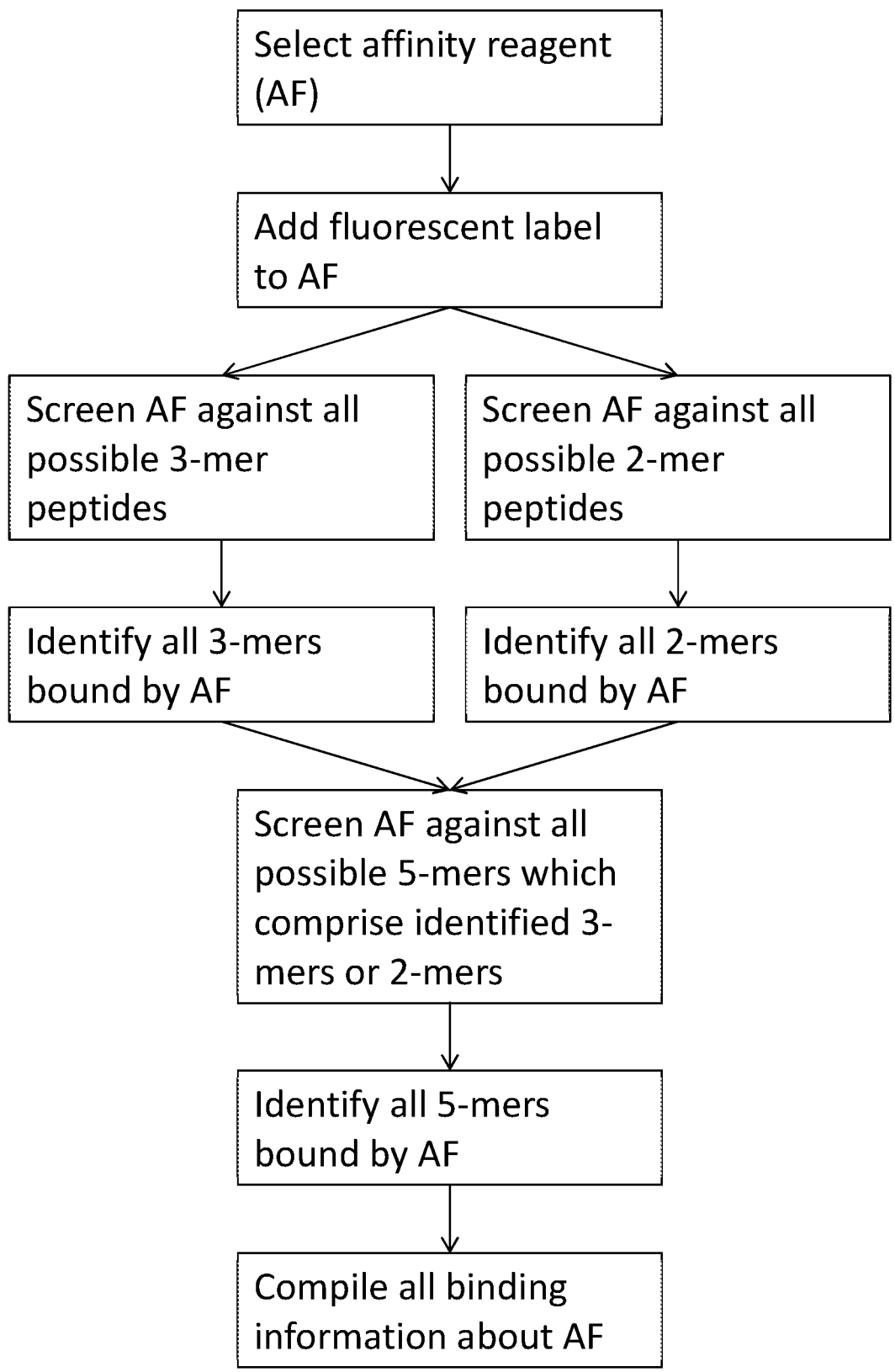
FIG. 3A illustrates an exemplary flowchart of screening steps in the process of affinity reagent characterization, in accordance with some embodiments.
Figure 3B:
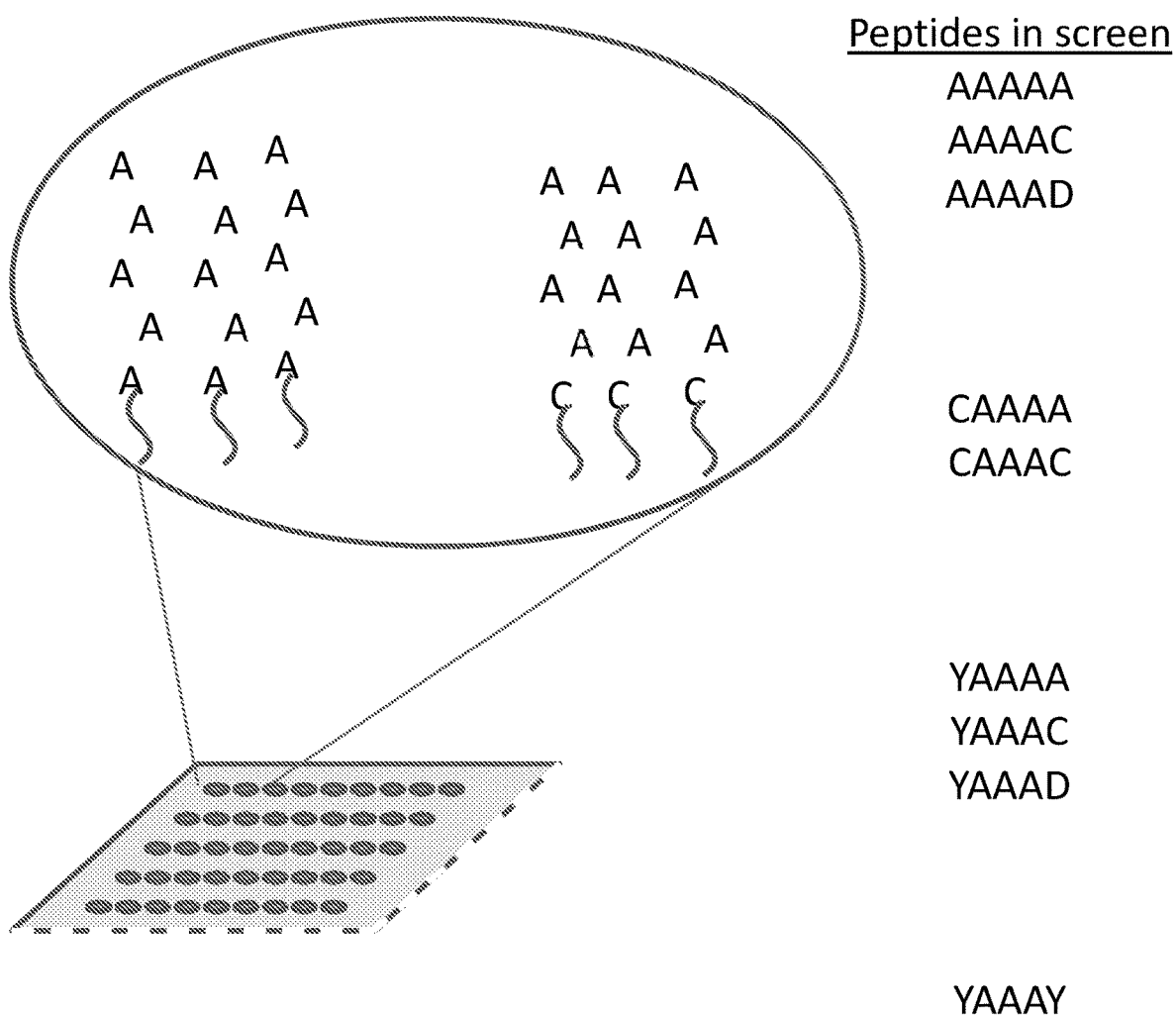
FIG. 3B illustrates an array of 5-mer α Xβ peptides for undertaking a screening step to determine the effect of flanking sequences on the binding of an affinity reagent to the epitope AAA, in accordance with some embodiments. Figure discloses SEQ ID NOS 2, 2, 2-3, 3, 3, 2-3, 20, 4-5, and 21-24, respectively, in order of appearance.
Figure 4:
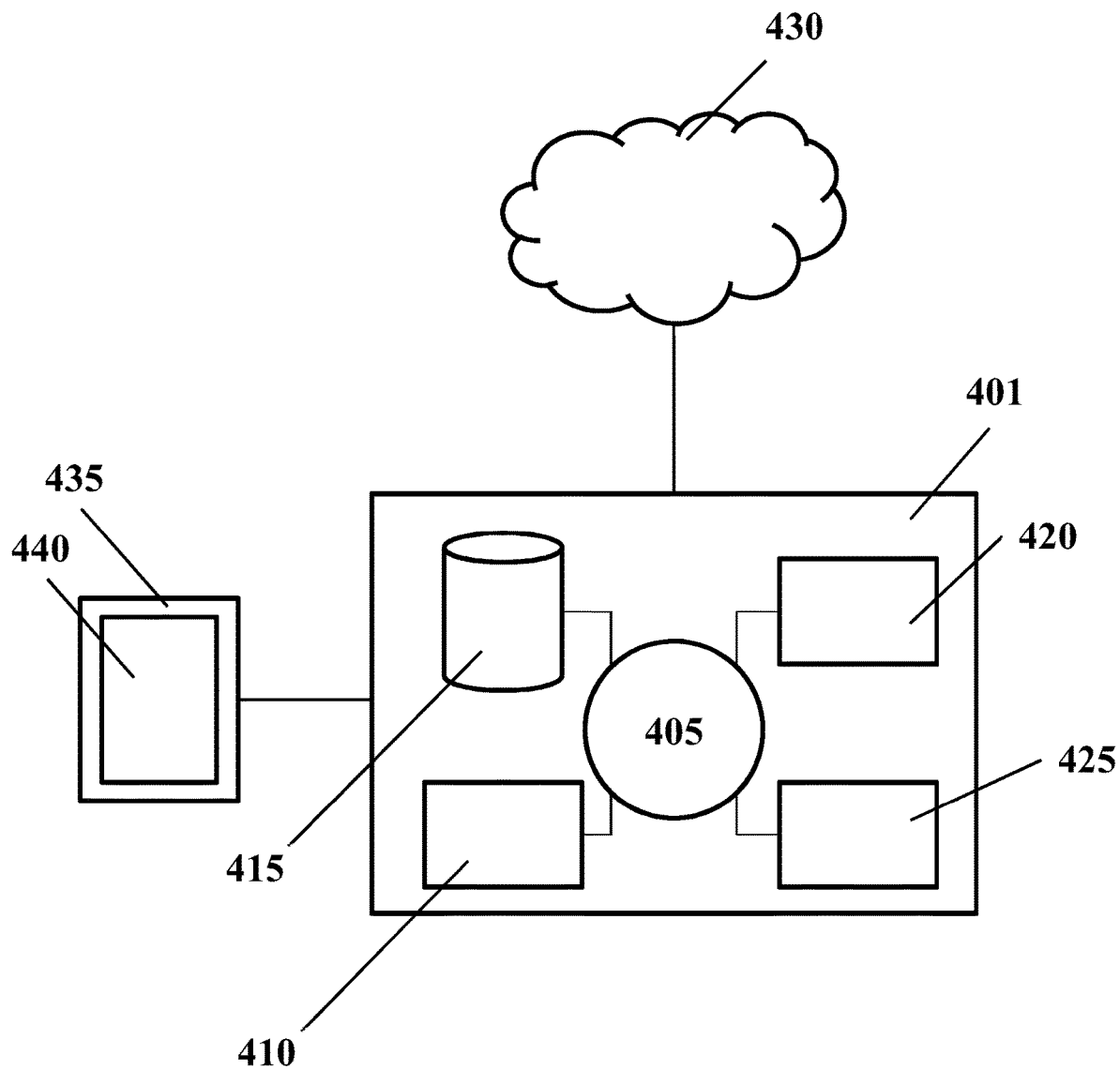
FIG. 4 illustrates a computer control system that is programmed or otherwise configured to implement methods provided herein.
Figure 5A:
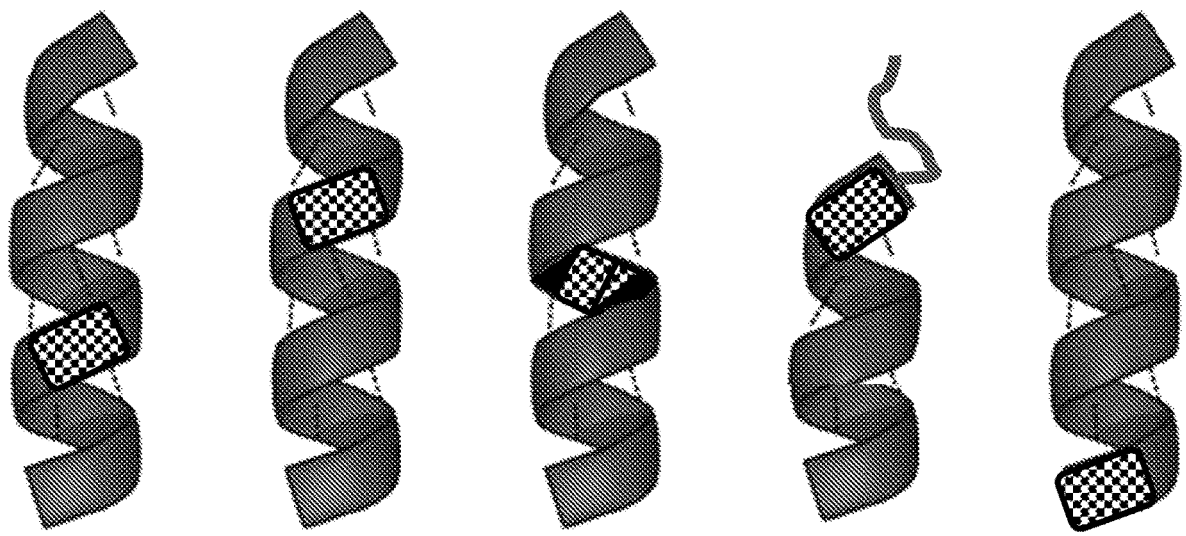
FIG. 5A illustrates examples of peptides forming alpha helices with embedded targets (shown as checked boxes) in different regions of the alpha helical peptide, in accordance with some embodiments.
Figure 5B:
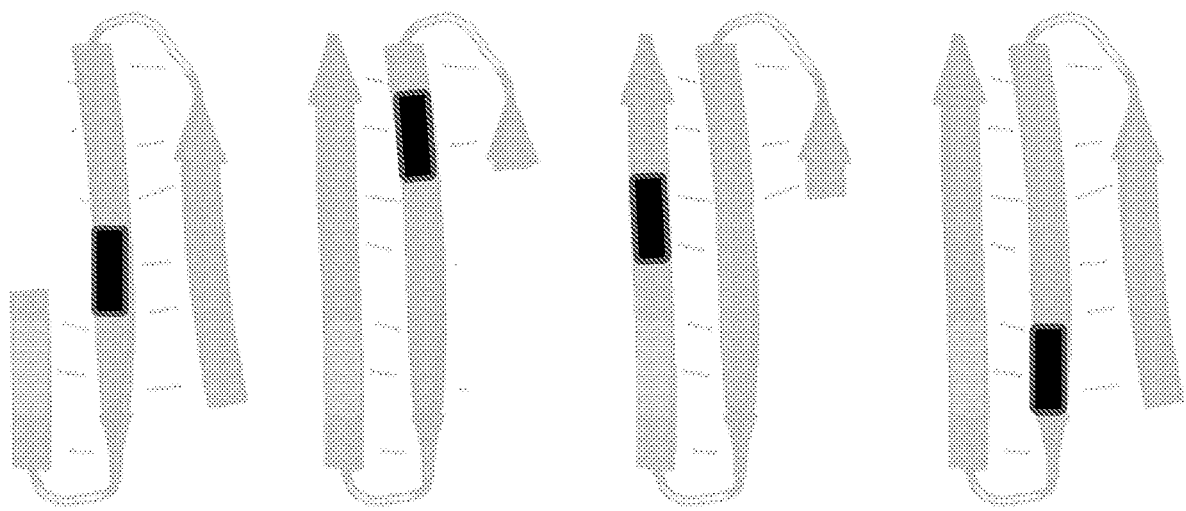
FIG. 5B illustrates examples of peptides forming beta sheets with embedded targets (shown as solid black boxes) in different regions of the beta sheet forming peptide, in accordance with some embodiments.

FIG. 3A illustrates an exemplary flowchart of screening steps in the process of affinity reagent characterization, in accordance with some embodiments. An affinity reagent is labeled with a fluorescent label to facilitate detection of the affinity reagent. The affinity reagent is then applied to a pool of peptides comprising all possible N-mer (e.g., 3-mer) sequences. The pool of peptides comprising all possible N-mer sequences may be immobilized as an array on a solid support. In some embodiments, the pool of peptides comprising all possible N-mer sequences may be immobilized on one or more single molecule protein arrays. In some embodiments, a plurality of N-mer sequences may be immobilized on a solid substrate. In some embodiments, a plurality of N-mer sequences may be immobilized on a single molecule protein array. In another step, which may be performed in parallel, the affinity reagent is then applied to a pool of peptides comprising all possible (N−1)-mer sequences. All N-mer and (N−1)-mer peptides bound by the affinity reagent are identified. A pool of (N+2)-mer peptides is obtained which contains all possible (N+2)-mer peptides which contain the sequences of the identified bound N-mers and (N−1)-mers. As an example, if the affinity reagent is known to bind only the epitope AAA, then the pool of all possible (N+2)-mer peptides consist of the peptides $\alpha AAA \beta$, as illustrated in FIG. 3B. The affinity reagent is then applied to the pool of (N+2)-mer peptides, and data from all three screening steps is compiled to provide a binding characterization of the affinity reagent. In other examples steps may be omitted or performed in a different order. A protein qualification screen may be performed to confirm that the affinity reagent binds to the desired epitope, or epitopes, in the context of a protein rather than a peptide. Proteins of known identity and sequence may be immobilized on a solid support and exposed to the affinity reagent.

The proteins may be applied to the solid support from purified protein stocks, or may be synthesized on the solid support through a process such as Nucleic Acid-Programmable Protein Array (NAPPA). In some cases, the proteins used for this screen may consist of proteins which include the predicted or known epitope or epitopes of the affinity reagent. In some cases, the proteins used for this screen may consist of proteins which do not include the predicted or known epitope or epitopes of the affinity reagent. In some cases, the proteins used for this screen may consist of both proteins which include the predicted or known epitope or epitopes of the affinity reagent, and proteins which do not include these epitopes. Binding of the affinity reagent to different proteins may be assessed by any method known in the art. For example, bound affinity reagents may be identified by affinity reagent specific antibodies, by dyes which bind to protein or nucleic acid, or by labeling the affinity reagents with a detectable moiety prior to screening. Once the bound and unbound proteins have been determined the sequences may be compared to determine how often the affinity reagent binds to its epitope, or epitopes, and whether the binding is affected by the surrounding protein sequence. The binding results and protein sequences may also be fed into a machine learning algorithm to verify the most likely binding sites. Off-target affects may also be determined by this method. In some cases, an affinity reagent against an epitope may be selected if it binds to at least about 1%, 2%, 3%, 5%, 7%, 10%, 15%, 20%, 30%, 40%, 50%, 60%, 70%, 80%, 90%, 95%, or more than 95% of the proteins which contain the epitope. In some cases, an affinity reagent against an epitope may be selected if it binds to less than about 50%, 40%, 30%, 20%, 10%, 5%, or less than 5% of the proteins which do not contain the epitope. In some cases, multiple affinity reagents may be selected against the same epitope. Said multiple affinity reagents may be pooled together and used as a pooled affinity reagent.

An affinity reagent may be characterized in an absolute or probabilistic fashion. An absolute characterization may comprise constructing a set of known epitopes, families of epitopes, protein properties, or other characterization parameters to which an affinity reagent has an affinity. A probabilistic characterization of an affinity reagent may comprise a context-dependent or context-independent measurement of the likelihood of binding to an epitope or family of epitopes. A context-dependent affinity agent characterization might be, for example, an affinity reagent has a 25% likelihood of binding epitope X when a peptide or protein is in its native state, and a 75% likelihood of binding epitope X when a peptide or protein is denatured. A context-independent characterization may be, for example, an affinity reagent has a 35% likelihood of binding epitope X. Affinity reagent characterization may occur under many binding conditions such as temperature ranges, buffering conditions (e.g., pH, molarity), presence of binding competitors, peptide or protein folding state (e.g., native, non-native), and any other condition that may affect affinity reagent binding.

Characterization of Affinity Reagents Using Binding Data from Interactions with Known Proteins It is useful to find ways of characterizing binding affinities of particular affinity reagents across the proteins comprising a proteome (e.g. human proteome, yeast proteome, *E. coli* proteome). Even when looking at the ~70,000 canonical protein sequences defined within the reference proteome database on Uniprot (https://www.uniprot.org/proteomes/UP000005640), it would take a great amount of effort to characterize the binding affinity of a set of particular affinity reagents across the entire set of proteins in the human proteome. Further, when proteoforms are considered, the number of distinct proteoforms within the human proteome that may be identified may number in the hundreds of thousands or millions. As such, it is beneficial to efficiently characterize binding affinities of affinity reagents in a way that is able to be applied across a number of unknown proteins. In some embodiments, binding affinities of affinity reagents are generated by assessing interactions of affinity reagents with known proteins. In some embodiments, binding affinities of affinity reagents are generated by assessing interaction of affinity reagents with proteins with sequences derived from sequence databases such as reference proteomes from NCBI or Uniprot. In some embodiments, protein sequences used in methods provided herein may have no known natural origin, such as proteins having random sequences. In some embodiments, synthesizing proteins having non-natural sequences may be useful in providing additional input into models such as those discussed herein. In some embodiments, binding affinities of affinity reagents to particular targets within known proteins may be assessed based on the presence of that target within the known protein and based on the number of copies of the target within the known protein.

Accordingly, in some cases, affinity reagents, such as affinity reagents disclosed herein, may be characterized by screening the affinity reagents against an array of known proteins. Binding data that is generated from the screening of the affinity reagents against the known proteins may be used to generate binding affinity information that may be used to assess whether an epitope, or multiple epitopes, that the affinity reagent binds is present within an unknown protein. In particular, each affinity reagent may bind to one or more epitopes. Further, each protein may contain multiple epitopes that may each bind to a particular affinity reagent. For proteins that contain multiple epitopes that bind to a particular affinity reagent, the protein may have multiple copies of a particular epitope and/or may have multiple copies of distinct epitopes. As such, in some cases a particular protein may bind to multiple affinity reagent molecules, with each of the multiple affinity reagent molecules potentially attaching to one of a plurality of epitopes present within a protein. Accordingly, information that helps to characterize affinity reagents and predict binding to proteins may be applicable to methods of identifying unknown proteins. In some embodiments, the binding data that is generated may be used to identify unknown proteins for which a sequence is represented within a protein database. In some embodiments, the binding data may be used to generate a particular profile that may be used to characterize an unknown protein until a sequence that is associated with the unknown protein is identified. In particular, binding data generated from interactions of affinity reagents with proteins in the array of known proteins may be used to determine the binding affinity of an affinity reagent for one or more epitopes within the known proteins. This, in turn, may be used in assessing binding affinity for the screened affinity reagents against proteins having one or more copies of those one or more epitopes. Additionally or alternatively, the binding affinity of an affinity reagent for one or more epitopes may be used in assessing binding affinity for the screened affinity reagents against proteins having other epitopes that are similar to, or the same as, the characterized one or more epitopes. In some embodiments, binding data from interactions of affinity reagents screened against proteins in the array of known proteins may be used to determine affinity characteristics of particular types of epitopes, such as each possible epitope of a particular length, epitopes within a particular subset of the complete protein sequence, epitopes in a particular location of the folded protein structure, each epitope predicted or observed to be highly accessible in the folded protein structure, or each epitope identified from an empirical or in silico binding screen, within one or more proteins within the array of known proteins. In some embodiments, the binding data from interactions of affinity reagents screened against proteins in the array of known proteins may be used to determine binding affinities of affinity reagents with multiple epitopes within one or more proteins within the array of known proteins. In some embodiments, the binding data from interactions of affinity reagents screened against proteins in the array of known proteins may be used to determine a binding affinity of an affinity reagent with a protein that has multiple copies of a particular epitope.

A method for conducting a screen of affinity reagents against an array of known proteins is described below. As described below, the method may provide that tested affinity reagents bind at least one N amino acid epitope (e.g., a trimer) or a combination of N-mers. Embodiments of the method may include one or more epitopes of different lengths other than trimers, such as dimers 4-mers, 5-mers, 6-mers, 7-mers, longer epitopes and non-contiguous epitopes. In some embodiments, methods may provide that tested affinity reagents bind at least one dimer or a combination of dimers. In some embodiments, methods may provide that tested affinity reagents bind at least one dimer or trimer or combination of dimers or trimers. In some embodiments, methods may provide that tested affinity reagents bind two or more N-mers selected from the group consisting of dimers, trimers, 4-mers, 5-mers, 6-mers, 7-mers, N-mers longer than 7-mers, and non-contiguous epitopes. In some embodiments, methods may provide that tested affinity reagents bind three or more N-mers selected from the group consisting of dimers, trimers, 4-mers, 5-mers, 6-mers, 7-mers, N-mers longer than 7-mers, and non-contiguous epitopes. In some embodiments, methods may provide that tested affinity reagents bind more than three N-mers selected from the group consisting of dimers, trimers, 4-mers, 5-mers, 6-mers, 7-mers, N-mers longer than 7-mers, and non-contiguous epitopes.

Using methods provided herein, protein inferences may be calculated. In some embodiments, protein inferences may be calculated based on one or more considerations, such as binding measurements of particular affinity reagents to a protein; information related to protein sequences of possible candidate proteins of the protein; and information, such as binding affinity information, from which a prediction having a particular degree of confidence of the expected degree of binding for each affinity reagent to each candidate protein may be derived. Some methods as described herein are provided for generating a statistical model of an affinity reagent from which the probability of the affinity reagent binding to a protein may be computed provided a primary sequence of that protein.

In some embodiments, a statistical model may be trained using a series of binding measurements of a plurality of particular affinity reagent to each of a plurality of known proteins. This approach may be used to predict affinity reagent—protein binding when direct empirical measurements are not available. In the context of applying methods to proteins within a human proteome, a minimal list of candidate human proteins may contain approximately 20,000 proteins. Further, allowing for splicing variants, polymorphisms, partial degradation, and additional non-human genomes may rapidly expand candidate proteins to number in the hundreds of thousands or millions.

In some cases, the present disclosure may comprise a method of characterizing a selected affinity reagent by screening the selected affinity reagent against a panel of peptides with random sequence or a panel of peptides of which only a subset contain the targeted epitope. In some cases, binding of the selected affinity reagent to an epitope not present in the set of peptides or proteins screened (e.g., an epitope comprising a non-natural amino acid) may be imputed using an imputation model. In some cases, an imputation model may be trained from binding measurements of the selected affinity reagent against a plurality of peptides or proteins. In some cases, an imputation model may be trained from binding measurements of other affinity reagents against a plurality of proteins or peptides. In some cases, an imputation model may be supplemented by epitope similarity metrics calculated from e.g. amino acid substitution matrices (e.g. PAM, BLOSUM), amino acid properties (e.g. charge, hydrophobicity, polar surface area), physiochemical based amino acid distances (such as Grantham's distance) or a combination thereof.

Method

In some embodiments, an array of known proteins sequences is obtained. In some embodiments, this array of known proteins may be generated by spotting pure protein samples onto a chip. In some embodiments, this array of known proteins may be generating by translating proteins directly onto a chip, for example by using a nucleic acid programmable protein array (NAPPA). The number of known proteins which may be analyzed, across one or more particular arrays, may contain less than 50 different protein sequences, may contain 50 different protein sequences, may contain more than 50 protein sequences, may contain approximately 100, 150, 200, 250, 300, 350, 400, 500, 600, 700, 800, 900, 1,000, 2,000, 3,000, 5,000, 10,000, 15,000, 20,000, or more than 20,000 protein sequences. As a generalized concept, as more proteins are analyzed, the accuracy of a model being developed may be increased. In some embodiments, the number of known protein which may be analyzed may be between about 300 and about 3000 different protein sequences; between about 500 and about 2000 different protein sequences; between about 600 and about 1500 different protein sequences; between about 600 and about 1000 different protein sequences; or between about 1000 and 3000 different protein sequences, among other examples. In some embodiments, each known protein may be present in multiple copies at a single location on the array. In some embodiments, each protein may present, in multiple copies, in numerous locations across the array. In some embodiments, each protein may be present in two locations, three locations, four locations, five locations, six locations, seven locations, eight locations, more than eight locations, or a combination of different numbers of locations, across the array. In some embodiments, each protein may be present in greater than about 1000 copies, 2000 copies, 3000 copies, 5000 copies, 10,000 copies, 20,000 copies, 50,000 copies, 100,000 copies, 500,000 copies, 1,000,000 copies, 2,000,000 copies, 5,000,000 copies, 10,000,000 copies, 100,000,000 copies, 1 billion copies, 10 billion copies, 100 billion copies, or more than 100 billion copies at each of one, two, three, four, five, six, seven, eight, or more than eight locations, across the array. Further, in some embodiments, affinity reagents may also be characterized by assessing small numbers of proteins at particular locations, such as 1 copy per location, 2 copies per location, 3 copies per location, 4 copies per location 5 copies per location, 10 copies per location, or more than 10 copies per location. In some embodiments, locations may be distinguished from one another when each particular location is resolvably distinct from another location based on optical detection or other detection sensors.

In some embodiments, binding of one or more affinity reagents to known proteins within the array may be assessed by hybridizing a fluorescently-labelled affinity reagent to the array and measuring observed fluorescence at each spot on the array. In some embodiments, the identity of each protein at each spot may be known so that fluorescence (as a proxy for binding) may be mapped to protein identities.

In some embodiments, N-mer (e.g., trimer) epitopes may be used in assessing binding of affinity reagents to particular epitopes within any peptide longer than the desired or target epitope (e.g., proteins, protein fragments, peptides, partially-degraded proteins). In some embodiments, methods discussed herein may be applied using trimer epitopes. In some embodiments, protein-level fluorescence measurements may be used to derive a fractional contribution to the fluorescence measurement from individual epitopes, such as from each individual epitope. In some embodiments, protein binding may be modeled as a linear combination of a count of each of the possible N-mers in the protein sequence, e.g., 8000 possible trimers in the protein sequence, and the fractional fluorescence from those N-mers. For a trimer, this may be expressed as:

$$F_{pr} = \sum_{t=1}^{t=8000} c_{t,pr} \beta_t$$

Where:

In some embodiments, measurements for an affinity reagent to trimer epitopes against multiple proteins may form a linear system of equations:

$$\vec{F} = C\vec{\beta} + \in$$

Where:

$\vec{F}$ is a length N column vector containing the observed measurement (e.g. fluorescence) for each protein C is an N×8000 matrix of trimer counts with each column being counts for a particular trimer in each measured protein $\vec{\beta}$ is a length 8000 column vector of fractional fluorescence from binding of the reagent to each possible trimer $\in$ is a scalar constant to correct for background binding or a noise floor In some embodiments, methods provided herein may include non-standard amino acids and/or model N-mers of different length. In the case of known NAPPA or similar binding measurements, $\vec{F}$ and C are known variables, and values for $\vec{\beta}$ and $\in$ may be derived by linear regression or related approaches. In particular, non-negative least squares and non-negative least absolute shrinkage and selection operator (LASSO) regression may be well-suited for considerations of methods described herein. Non-negative least squares bounds the solution $\vec{\beta}$ to be non-negative, and non-negative LASSO regression further imposes a sparsity constraint. LASSO regression is particularly effective when the system is underdetermined, that is, when the number of unique proteins measured is less than the number of unique trimers (8,000 in this example). In some embodiments, the fractional fluorescence derived from each epitope may be used to estimate binding characteristics, such as binding kinetics, of particular affinity reagents to individual epitopes. In some embodiments, the relative fractional fluorescence may be considered proportional to relative binding affinity of the affinity reagent to each of the epitopes. In some embodiments, fractional fluorescence may be converted to a calculation of the fraction of sites bound by dividing by the number of fluorescent counts per fluorophore and then dividing by the expected number of protein molecules per spot on the array. A simulation of this method is provided in Example 2 where a set of binding affinities of a theoretical affinity reagent are used to predict binding of the affinity reagent to 720 human proteins, and the predicted binding data is then solved to determine the affinities of the affinity reagent to each possible trimer epitope.

Data that is gathered from embodiments of modeling protein to affinity reagent binding may be used to help train other models that predict protein binding affinity from the primary sequence of a protein. In some embodiments, data that is gathered from embodiments of modeling protein to affinity reagent binding may be used to help train other models that predict protein binding affinity from a derivative of the primary sequence (e.g. amino acid composition, trimer count, predicted three-dimensional structure). In some embodiments, models may include similar parameters to those discussed with epitopes having different lengths (e.g. 1 mers, 2 mers, 4 mers, etc.) or a mixture of epitopes having different lengths. In some embodiments, models may use a non-linear model, for example with an exponential function relating trimer affinity to observed fluorescence or a multiplicative model where trimer-level affinities are multiplied to generate a protein level affinity. In some embodiments, a neural network may be used to predict protein binding affinity from protein sequence or trimer composition. Additionally, a support vector regression model may be used to predict protein binding affinity from protein sequence or trimer composition.

A further method may allow the identification of N-mers driving protein-level binding, when only protein-level binding measurements are available. This method may work in any context where the bound molecule (e.g., a peptide) has a sequence longer than the epitope, up to and including proteins (e.g, learning trimer epitopes from a PEPperPrint chip with 15-mers conjugated to it). In some cases, an affinity reagent is shown to have affinity to a single protein. Without follow-up experiments, it may be computationally intractable to determine what subsequences of the protein are driving the affinity of the affinity reagent to the protein. However, if binding measurements are acquired for that affinity reagent against hundreds of proteins, and the affinity reagent bound to many of them, patterns might begin to emerge. In some cases, the affinity reagent may favor proteins that have a particular N-mer (e.g., a trimer) in them, for example. The algorithm described herein is an approach to determining the trimer binding probabilities (the probability of the affinity reagent binding each of the 8000 possible trimers if seen on the protein) of an affinity reagent from a collection of protein binding measurements. More specifically, the protein binding measurements are the fractional binding of the probe to the protein. For example, if 1,000 copies of a single protein were deposited on an array, and after hybridization, the affinity reagent bound to 250 of the proteins, the fractional binding would be 0.25. The described method may be extended to epitopes comprising other characteristics or sequence lengths.

The approach may use a probabilistic model for affinity reagent protein binding built on trimer binding probabilities. With this model, the probability of a single molecule of the affinity reagent binding to a single copy of any protein can be estimated, given the primary sequence of the protein.

The binding probability p of an affinity reagent to a protein is modeled as:

$$p = 1 - \prod_{j=1}^{8000} \theta_j^{x_j}$$

with:
X: the count of each trimer j in the protein substrate
X={$x_1$, $x_2$, $x_3$ ... $x_{8000}$} with $x_j \in \mathbb{Z}$*
θ: the binding model parameters. A vector of probabilities of the probe not binding each trimer
θ={$\theta_1$, $\theta_2$, $\theta_3$, ... $\theta_{8000}$} with $0 \leq \theta_j \leq 1$
The probability of an affinity reagent not binding to a protein is equal to 1−p.
The probability of an affinity reagent binding to any particular trimer j is equal to $1-\theta_j$.
The likelihood of a particular affinity reagent binding model given an observed binding outcome to a single protein substrate is:

$$L(\theta \mid y, X) = \left(\prod_{j=1}^{8000} \theta_j^{x_j}\right)^{1-y} \left(1 - \prod_{j=1}^{8000} \theta_j^{x_j}\right)^{y}$$

with:
y: the binding outcome $$y = \begin{cases} 1 & \text{if binding} \\ 0 & \text{if no binding} \end{cases}$$

The log-likelihood is:

$$\log(L(\theta \mid y, X)) = (1-y)\sum_{j=1}^{8000} x_j \log\theta_j + y\log\left(1 - \prod_{j=1}^{8000} \theta_j^{x_j}\right)$$

The log likelihood of multiple binding outcomes may also be calculated.
If N binding outcomes are observed for N single-copy protein substrates:
Y is a vector of N binding outcomes
X is an N×8000 matrix of trimer counts for each of the N substrates where any row $X_i$ is the counts for each of 8000 trimers for the i th substrate.
The log likelihood of a binding model θ given this set of observations is:

$$\log(L(\theta \mid Y, X)) = \sum_{i=1}^{N}\left((1-y_i)\sum_{j=1}^{8000} x_{ij}\log\theta_j + y_i\log\left(1 - \prod_{j=1}^{8000}\theta_j^{x_{ij}}\right)\right)$$

Maximization of the above likelihood function may be used to make an estimate $\hat{\theta}$ of the parameters θ of the affinity reagent binding model. With the current formulation, multiple binding outcomes to copies of the same protein would be represented as individual entries in the vector Y, and rows in the matrix X which may lead to a large memory footprint when using software to compute the log likelihood. To reduce the computational resources required, the same calculation may be performed using a more compact representation of the binding data where binding outcomes are collapsed into the number of binding and non-binding events for each unique protein substrate in the collection of outcomes. With this reformulation, the dimensions of the matrices and vectors used for computation scales with the number of unique proteins in the data set rather than the number of binding outcomes observed.

In the alternative formulation:

$$\log(L(\theta \mid U, B, T)) = \sum_{i=1}^{M}\left(u_i \sum_{j=1}^{8000} t_{ij}\log\theta_j + b_i\log\left(1 - \prod_{j=1}^{8000}\theta_j^{t_{ij}}\right)\right)$$

with:
binding observations consisting of M unique proteins
B is a vector of binding counts and U is a vector of non-bind counts to each unique protein. Both of length M
T is the matrix of trimer counts for each unique protein with M rows and 8000 columns.

This approach estimates the binding model B by minimizing the function $f(\hat{\theta}) = -\log(L(\hat{\theta} \mid U, B, T))$ using the L-BFGS-B algorithm with each parameter of $\hat{\theta}$ constrained to be greater than zero and less than one.

The speed of maximum likelihood estimation is improved by providing a function $J = j(\hat{\theta})$ to directly compute the analytical gradient vector J of $f$ given a parameter estimate $\hat{\theta}$. The analytical gradient is:

$$J = j(\hat{\theta}) = \begin{bmatrix} \frac{\partial f}{\partial \hat{\theta}_1} & \frac{\partial f}{\partial \hat{\theta}_2} & \cdots & \frac{\partial f}{\partial \hat{\theta}_{8000}} \end{bmatrix}$$

$$\frac{\partial f}{\partial \hat{\theta}_q} = -\sum_{i=1}^{M}\left(\frac{u_i t_{iq}}{\hat{\theta}_q} - \frac{b_i t_{iq}\prod_{j=1}^{8000}\hat{\theta}_j^{t_{ij}}}{\hat{\theta}_q\left(1 - \prod_{j=1}^{8000}\hat{\theta}_j^{t_{ij}}\right)}\right)$$

As demonstrated, the approach may work with individual counts of binding and non-binding events for each unique protein in the set of experimental observations. However, in cases where only fractional binding can be determined or estimated, the vector B can be replaced with a vector F of length M containing the fractional binding to each of the M unique proteins in the data set and the vector U replaced with the vector D=1−F. For example, in the case of hybridization of a fluorescent-labeled affinity reagent candidate to a nucleic acid programmable protein array (NAPPA) followed by imaging to measure fluorescence intensity, values for F may be estimated as the fluorescence intensity for a given protein divided by an estimate of the fluorescence intensity that would be observed at a fractional binding of 1 (all protein bound).

In cases where a particular trimer is not observed at all in the binding data set, only observed in a single unique protein sequence, or is always observed with another specific trimer in each of its protein sequence contexts, the binding probability of the trimer may be difficult to learn. For such trimers, the binding probability may be imputed, for example by setting the probability of the trimer to be equivalent to that of another trimer that is similar based on sequence or biochemical characteristics. In some cases, imputation may be performed by setting the probability of the trimer to the average binding probability of all other trimers that were not imputed.

The above approach may be applied to learn binding models built from dimers, trimers, 4-mers, 5-mers, etc. Furthermore, it may also be applied to models comprising subsets or mixtures of the aforementioned N-mers. To do so, the columns representing the counts in each protein for each trimer (1-8000), may be replaced with columns representing the counts of each N-mers in each protein in the matrix M. Further, the parameter vector θ would be the binding probability to each of the N-mers used in the model.

Improvements to the Characterization of Affinity Reagents

The above-described computer-implemented algorithms may improve the characterization of affinity reagent binding specificity and permits a rapid screening method for predicting the binding affinity for an uncharacterized affinity reagent. For example, binding could be measured against a protein pool or peptide library comprising millions of peptides or proteins using a known pool of characterized affinity reagents. A subsequent, uncharacterized affinity reagent could then have its binding measured against the same protein pool or library. The above-described algorithms may enable a rapid characterization of the binding affinity for the uncharacterized affinity reagent. Utilization of the above-described method may improve the screening and characterization of affinity agents of unknown binding affinity, thereby resulting in one or more affinity reagents being added to an affinity reagent pool for use in protein characterization or identification methods.

The above-described, computer-implemented algorithms may operate using single-molecule measurement data. The above-described, computer-implemented algorithms may be able to work with full protein sequences. The above-described, computer-implemented algorithms may be able to work with hundreds of millions or billions of datapoints when characterizing affinity reagents.

The above-described, computer implemented algorithms may be able to pull reliable N-mer-level binding measurements from longer sequences, thereby permitting numerous new potential affinity reagent characterization methods that may not be feasible without such an approach. The above-described algorithms may be able to assess binding affinity based upon diverse sources of peptide or epitope binding data, such as: peptide pull-down with mass spectrometry, spotted peptide array, spotted protein array, phage display, NAPPA, and a printed peptide array (such as PEPperPrint). The above-described, computer-implemented may permit a previously uncharacterized affinity reagent to be used for protein identification without a rigorous or absolute measurement of its binding affinity.

Assessing the Influence of Secondary Structure on Affinity Reagent Protein Binding Binding of affinity reagents to proteins may be influenced by the presence of secondary structural elements, such as helices, turns, loops, and sheets. In some embodiments, an approach leveraging peptide arrays and protein structure databases may be used to assess how binding of an affinity reagent to an epitope is altered by the presence of secondary structure. In some embodiments, information related to known protein structures may be used to identify regions of proteins which form different secondary structures, such as alpha helices and beta sheets, and which also contain epitopes of interest. In some embodiments, the epitopes of interest may be within the identified secondary structures. In some embodiments, the epitopes of interest may be nearby the identified secondary structures. In some embodiments, protein regions having known secondary structures may be synthesized and used to assess the binding of the affinity reagents compared to different protein regions which have not been observed to have secondary structure. In some embodiments, protein regions having known secondary structures may be synthesized and used to assess the binding of the affinity reagents as compared to scrambled sequences which contain the epitopes of interest and the same amino acid composition as the structured region but a different amino acid sequence.

In some embodiments, methods for measuring binding affinities of an affinity reagent to different secondary structures may involve using hundreds or thousands of peptides on printed peptide arrays such as those available from PEPperPRINT. For example, an array containing 11,000 peptides, each peptide having a length of 10-30 residues, may be printed and then hybridized with a fluorescently labeled affinity reagent. The amount of fluorescence measured at each spot on the array may be considered to be proportional to a binding affinity of an affinity reagent to a corresponding peptide localized at the spot. In some embodiments, methods may be provided to test for structural influence. For example, an array may be printed containing "structural" peptides—e.g. peptides such as 15-mers that may be expected to have a particular secondary structure that also contain the epitope of interest. Additionally, an array may alternatively or additionally be printed to include "unstructured" peptides that have not been observed to have secondary structure and that also include a same epitope of interest. "Unstructured" peptides may be constructed by modifying portions of a particular sequence so as to modify one or more sequences portions that are associated with secondary structures, thereby producing a modified sequence that is either observed to have less secondary structures than an original peptide or is observed as not having any secondary structures. By measuring the different indicators of binding affinity (e.g., an amount of fluorescence, or another indicator of attachment between the affinity reagents and the peptides), a determination may be made as to how the presence of secondary structural components may influence the particular binding affinities of particular affinity reagents with respect to one or more epitopes of interest.

Finding Structured Peptides

In some embodiments, sequences for structured peptides may be derived from regions of endogenous proteins that are known to be structured. In some embodiments, these peptides may be found by initially searching a reference proteome (e.g. Uniprot human reference proteome) to find all occurrences of the epitope in annotated protein sequences for the species of interest. Once the occurrences of the epitope in annotated protein sequences for the species of interest are identified, sequence locations containing epitopes may be cross-referenced with structural data from a protein database, such as Protein Data Bank (PDB). Additionally or alternatively, software that predicts secondary structures may be used to determine whether sequence locations containing epitopes are associated with a structural motif (e.g. a secondary structure) of interest. Software programs that may be used to predict secondary structure include, but are not limited to, Rosetta (https://www.rosettacommons.org/software), I-TASSER (https://zhanglab.ccmb.med.umich.edu/I-TASSER/), and PEP-FOLD (http://bioserv.rpbs.univ-paris-diderot.fr/services/PEP-FOLD/), among other examples.

Once sequence locations/sequence portions that are associated with structural data are identified, epitopes that are within sequence portions associated with a structural motif of interest (e.g. beta sheet, alpha helix, turn) may be removed. Further, for each instance of the epitope that is within a structural element, the epitope and structured flanking sequence may be extracted from either side of the epitope. Several different extractions may be performed for each epitope, for example one where the epitope is at the beginning of the peptide, one where the epitope is near the middle of the peptide, and one with the epitope at the end of the peptide. In some cases, a peptide length may be selected, for example a peptide length may be less than 10, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more than 40 residues. In some embodiments, possible fragments of an epitope and flanking sequences may be selected. For example, in a case with an epitope length of 3 and a peptide length of 15, there are 13 different sequences which may be selected depending on whether the epitope starts at the $1^{st}$-$13^{th}$ positions of the peptide. In some cases, multiple peptide lengths may be selected. Further, for each extracted peptide sequence (epitope+structured flanking sequence), "unstructured" peptides, where sequence portions associated with secondary structures are modified to alter or remove secondary structural characteristics. In some embodiments, "unstructured" peptides may be generated by shuffling one or more flanking sequences, but leaving the epitope in the same position. Shuffling a sequence may comprise changing the order of residues in the sequence while maintaining composition. Additionally, a composition may be regarded as a count of each residue in a sequence. In some embodiments, shuffling a sequence may comprise randomly altering the order of residues in the sequence while maintaining composition. In some embodiments, "unstructured" peptides may be generated by non-randomly altering the order of residues within a sequence while maintaining sequence composition. In some embodiments, "unstructured" peptides may be generated by incorporating non-natural or modified amino acid residues into a sequence. In some embodiments, "unstructured" peptides may be generated applying one or more of these methods in combination, in sequence, or to a subset of one or more flanking sequences associated with an epitope. In some embodiments, the secondary structures of the "unstructured" peptides may be assessed by synthesizing the peptides and using a method such as circular dichroism spectroscopy.

Assessing the Structured Peptides

Once structured and unstructured epitope containing peptides have been identified as above an array may be printed with many replicates of each of the structured and unstructured peptides. The array may then be hybridized with a fluorescently labeled affinity reagent. The amount of fluorescence measured at each spot on the array may be measured and a paired t-test comparing fluorescence measurements between the structured and unstructured peptides may be performed to determine if there is a significant increase or decrease in binding, e.g. due to secondary structure. If the fluorescence of the structured peptides is decreased relative to the unstructured peptides, this may indicate some degree of disruption of affinity reagent binding due to secondary structural elements. Due to challenges of protein folding, it is possible that not all of the "structured" peptides will fold into the predicted 'native' conformations when printed on an array. Use of multiple different structured peptide sequences and redundant fragments for each epitope may help to address this challenge. Any peptide which shows a significant change in binding affinity compared to other peptides with the same epitope may be selected for further study. For example, the peptide may be assessed by circular dichroism spectroscopy (CD spectroscopy) to determine whether it has adopted the expected secondary structure. In some cases, all peptides may be assessed by CD spectroscopy to determine the secondary structures prior to hybridization with the affinity reagents.

An alternative method for assessing the effect of secondary structure on affinity reagent binding may be to use full length proteins, either from cell free expression or from cell lysates. In some cases, highly structured proteins may be isolated from tissue samples, for example prion proteins, amyloid plaques, or tau fibrils. For example, samples of different recombinant proteins with known secondary structures may be obtained and used to assess the binding of the affinity reagents to the structured proteins compared to unstructured proteins, scrambled proteins, or denatured proteins. The method as described above may be used for any epitopes which are located within structured regions of the selected structured proteins. The proteins may be bound to a solid support to facilitate the assessment of binding, or may be maintained in solution and methods such as affinity pull down may be used to assess binding.

In some cases, the peptide qualification screen and protein qualification screen may be performed to select affinity reagents with desired properties. In other cases, the affinity reagents may be selected before performing either of the screens, and the screens may be performed to collect binding data about the affinity reagents.

Screening and selection steps may be performed for all possible epitopes of a given N-mer, for example for all 8000 possible 3-mers. In some cases, screening steps may only be performed for a subset of the possible N-mers. For example, rather than screening for affinity reagents for all 8000 3-mers, 800 3-mers may be selected as desired epitopes and the other 7200 3-mers may not be screened against.

In some cases, an affinity reagent selected using the methods described herein may bind to about 0.1%, 0.5%, 1%, 5%, 10%, 15%, 20%, 25%, 30%, 35%, 40%, 45% or 50% of all possible proteins in a proteome. In some cases, an affinity reagent selected using the methods described herein may bind to at least about 0.1%, 0.5%, 1%, 5%, 10%, 15%, 20%, 25%, 30%, 35%, 40%, 45% 50%, or more than 50% of all possible proteins in a proteome. In some cases, an affinity reagent selected using the methods described herein may bind to nor more than about 50%, 45%, 40%, 35%, 30%, 25%, 20%, 15%, 10%, 5%, 1%, 0.5%, 0.1% or no more than 0.1% of all possible proteins in a proteome. In some cases, a plurality of affinity reagents with different binding properties may be selected and pooled together such that the affinity reagent pool binds to about half of all proteins in a proteome. In some cases, an affinity reagent pool may be used in place of a single affinity reagent.

Affinity reagents may be any reagents which bind proteins or peptides with reproducible specificity. For example, the affinity reagents may be antibodies, antibody fragments, aptamers, or peptides. In some examples, monoclonal antibodies may be preferred. In some examples, antibody fragments such as Fab fragments may be preferred. In some examples, aptamers may be preferred. In some cases, the affinity reagents may be commercially available affinity reagents, such as commercially available antibodies. In some cases, the desired affinity reagents may be selected by screening commercially available affinity reagents to identify those with useful characteristics. In some cases, affinity reagents may be screened for their ability to bind a single protein. In some cases, affinity reagents may be screened for their ability to bind an epitope or amino-acid sequence. In some cases, groups of affinity reagents may be screened for their ability to collectively resolve similar proteins (e.g., those with highly similar sequence) through differential binding. In some cases, affinity reagents may be screened for overlapping binding characteristics to increase binding specificity for a particular protein. Screening of affinity reagents may be performed in a variety of different ways. One example would be to screen affinity reagents against a NAPPA or an epitope tiling array. In some cases, protein-specific affinity reagents designed to bind to a protein target may be used (e.g. commercially available antibodies or aptamers). In some cases, multiple protein-specific, or epitope specific, affinity reagents may be mixed prior to performing a binding measurement. For example, for each binding measurement pass, a new mixture of protein specific affinity reagents may be selected comprising a subset of the available affinity reagents selected at random from the complete set. For example, each subsequent mixture may be generated in the same random manner, with the expectation that many of the affinity reagents will be present in more than one of the mixtures. In some cases, protein identifications may be generated more rapidly using mixtures of protein-specific affinity reagents. In some cases, such mixtures of protein-specific affinity reagents may increase the percentage of unknown proteins for which an affinity reagent binds in any individual pass. Mixtures of affinity reagents may consist of 1%, 5%, 10%, 20%, 30%, 40%, 50%, 60%, 70%, 80%, 90% or more than 90% of all available affinity reagents. Mixtures of affinity reagents may consist of at least 1%, 5%, 10%, 20%, 30%, 40%, 50%, 60%, 70%, 80%, 90% or more than 90% of all available affinity reagents. Mixtures of affinity reagents may consist of no more than 90%, 80%, 70%, 60%, 50%, 40%, 30%, 20%, 10%, 5%, 1% or less than 1% of all available affinity reagents. Mixtures of affinity reagents may consist of 2, 3, 5, 10, 20, 30, 50, 100, 150, 200, 250, 300, 400, 500, 600, 700, 800, 900, 1000, 1200, 1500, 2000, 3000, 4000, 5000, 7000, 8000, 10000 or more than 10000 affinity reagents. Mixtures of affinity reagents may consist of at least 2, 3, 5, 10, 20, 30, 50, 100, 150, 200, 250, 300, 400, 500, 600, 700, 800, 900, 1000, 1200, 1500, 2000, 3000, 4000, 5000, 7000, 8000, 10000 or more than 10000 affinity reagents. Mixtures of affinity reagents may consist of no more than 10000, 8000, 7000, 5000, 4000, 3000, 2000, 1500, 1200, 1000, 900, 800, 700, 600, 500, 400, 300, 250, 200, 150, 100, 50, 30, 20, 10, 5, 3 or less than 3 affinity reagents.

The affinity reagents may have high, moderate or low specificity. In some examples the affinity reagents may recognize several different epitopes. In some examples the affinity reagents may recognize epitopes present in two or more different proteins. In some examples the affinity reagents may recognize epitopes present in many different proteins. In some cases, an affinity reagent used in the methods of this disclosure may be highly specific for a single epitope. In some cases, an affinity reagent used in the methods of this disclosure may be highly specific for a single epitope containing a posttranslational modification.

In some embodiments, an affinity reagent that is directed towards identifying a target amino acid sequence may actually comprise a group of different components which are not differentiated or distinguishable from each other as used in methods described herein. In particular, the different components that may be used to identify the same target amino acid sequence may use the same detection moiety to identify the same target amino acid sequence. For example, an affinity reagent which binds a trimer amino acid sequence (AAA) regardless of flanking sequences may comprise either a single probe which binds the trimer AAA sequence without any effect from flanking sequences, or a group of 400 probes, each of which binds to a different 5 amino acid epitope of the form $\alpha AAA\beta$, where $\alpha$ and $\beta$ may be any amino acid. In some cases of the second case, the 400 probes may be combined such that there is an equal amount of each one. In some cases of the second case, the 400 probes may be combined such that the amounts of each probe may be weighted by the characteristic binding affinities of each probe such that there is an equal probability of any given 5 amino acid epitope being bound.

Novel affinity reagents may be generated by any method known in the art. Methods of developing affinity reagents include SELEX, phage display, and inoculation. In some examples, affinity reagents may be designed using structure based drug design methods. Structure-based drug design (or direct drug design) utilizes knowledge of the three-dimensional structure of the epitope of interest and the binding site of the affinity reagent.

In some cases, the affinity reagents may be labeled with nucleic acid barcodes. In some examples, nucleic acid barcodes may be used to purify affinity reagents after use. In some examples, nucleic acid barcodes may be used to sort the affinity reagents for repeated uses. In some cases, the affinity reagents may be labeled with fluorophores which may be used to sort the affinity reagents after use.

In some cases, multiple affinity reagents that are labeled with nucleic acid barcodes may be multiplexed and then detected using complementary nucleic acid probes. A multiplexed group of affinity reagents may be detected in a single cycle using multiple complementary nucleic acids with distinct detection moieties. In some cases, a multiplexed group of affinity reagents may be detected in multiple cycles using a single complementary nucleic acid conjugated to a detection moiety. In some cases, a multiplexed group of affinity reagents may be detected in multiple cycles using multiple complementary nucleic acids each conjugated to a distinct detection moiety. In some cases, a multiplexed group of affinity reagents may be detected in multiple cycles using multiple complementary nucleic acids each conjugated to a distinct group detection moieties.

In some cases, one or more affinity reagents, that are labeled with nucleic acid barcodes, may be cross-linked to a bound protein. Once the one or more affinity reagents are cross-linked to the protein, the barcodes may be sequenced to determine the identity of the cross-linked affinity reagent. In some cases, multiple bound proteins may be exposed to the one or more affinity reagents. In some cases, when multiple bound proteins are cross-linked with one or more affinity reagents, the barcodes associated with the bound affinity reagents may be sequenced to determine the identity of the cross-linked affinity reagents associated with each of the multiple bound proteins.

The family of affinity reagents may comprise one or more types of affinity reagents. For example, the methods of the present disclosure may use a family of affinity reagents comprising one or more of antibodies, antibody fragments, Fab fragments, aptamers, peptides, and proteins.

The affinity reagents may be modified. Modifications include, but are not limited to, attachment of a detection moiety. Detection moieties may be directly or indirectly attached. For example, the detection moiety may be directly covalently attached to the affinity reagent, or may be attached through a linker, or may be attached through an affinity reaction such as complementary nucleic acid tags or a biotin streptavidin pair. Attachment methods that are able to withstand gentle washing and elution of the affinity reagent may be preferred. More than one detection moiety may be attached to each affinity reagent. Detection moieties may be attached to any position of the affinity reagent, including at terminal ends. The detection moiety may be attached in a location that does not alter the confirmation of the affinity reagent or the epitope-binding region of the epitope.

Detection moieties include, but are not limited to, fluorophores, bioluminescent proteins (GFP), enzymatic proteins (e.g., HRP), nanoparticles (e.g., quantum dots), nucleic acid segments including a constant region and barcode region, or chemical tethers for linking to a nanoparticle such as a magnetic particle. Detection moieties may include several different fluorophores with different patterns of excitation or emission.

The detection moiety may be cleavable from the affinity reagent. This can allow for a step in which the detection moieties are removed from affinity reagents that are no longer of interest to reduce signal contamination.

In some cases, the affinity reagents are unmodified. For example, if the affinity reagent is an antibody then the presence of the antibody may be detected by atomic force microscopy. The affinity reagents may be unmodified and may be detected, for example, by having antibodies specific to one or more of the affinity reagents. For example, if the affinity reagent is a mouse antibody then the mouse antibody may be detected by using an anti-mouse secondary antibody. Alternately the affinity reagent may be an aptamer which is detected by an antibody specific for the aptamer. The secondary antibody may be modified with a detection moiety as described above. In some cases, the presence of the secondary antibody may be detected by atomic force microscopy.

In some examples, the affinity reagents may comprise the same modification, for example a conjugated green fluorescent protein, or may comprise two or more different types of modification. For example, each affinity reagent may be conjugated to one of several different fluorescent moieties, each with a different wavelength of excitation or emission. This may allow multiplexing of the affinity reagents as several different affinity reagents may be combined and/or distinguished. In one example, a first affinity reagent may be conjugated to a green fluorescent protein, a second affinity reagent may be conjugated to a yellow fluorescent protein and a third affinity reagent may be conjugated to a red fluorescent protein, thus the three affinity reagents can be multiplexed and identified by their fluorescence. In a further example a first, fourth and seventh affinity reagent may be conjugated to a green fluorescent protein, a second, fifth and eighth affinity reagent may be conjugated to a yellow fluorescent protein and a third, sixth and ninth affinity reagent may be conjugated to a red fluorescent protein; in this case the first, second and third affinity reagents may be multiplexed together while the second, fourth and seventh, and third, sixth and ninth affinity reagents form two further multiplexing reactions. The number of affinity reagents which can be multiplexed together may depend on the detection moieties used to differentiate them. For example, the multiplexing of affinity reagents labeled with fluorophores may be limited by the number of unique fluorophores available. For further example, the multiplexing of affinity reagents labeled with nucleic acid tags may be determined by the length of the nucleic acid bar code.

The specificity of each affinity reagent can be determined prior to use in an assay. The binding specificity of the affinity reagents can be determined in a control experiment using known proteins. Any appropriate experimental methods may be used to determine the specificity of the affinity reagent. In one example a solid support may be loaded with known protein standards at known locations and used to assess the specificity of a plurality of affinity reagents. In another example, a solid support may contain both experimental samples and a panel of controls and standards such that the specificity of each affinity reagent can be calculated from the binding to the controls and standards and then used to identify the experimental samples. In some cases, affinity reagents with unknown specificity may be included along with affinity reagents of known specificity, data from the known specificity affinity reagents may be used to identify proteins, and the pattern of binding of the unknown specificity affinity reagents to the identified proteins may be used to determine their binding specificity. It is also possible to reconfirm the specificity of any individual affinity reagent by using the known binding data of other affinity reagents to assess which proteins the individual affinity reagent bound. Thus, with multiple uses of an affinity reagent panel the specificities of the affinity reagents may be increasingly refined with each iteration. While affinity reagents that are uniquely specific to particular proteins may be used, methods described herein may not require them. Additionally, methods may be effective on a range of specificities. In some examples, methods described herein may be particularly efficient when affinity reagents are not specific to any particular protein, but are instead specific to amino acid motifs (e.g. the tri-peptide AAA).

In some examples, one or more affinity reagents may be chosen to bind amino acid motifs of a given length, such as 2, 3, 4, 5, 6, 7, 8, 9, 10, or more than 10 amino acids. In some examples, one or more affinity reagents may be chosen to bind amino acid motifs of a range of different lengths from 2 amino acids to 40 amino acids.

In some examples, the affinity reagents may be chosen to have high, moderate, or low binding affinities. In some cases, affinity reagents with low or moderate binding affinities may be preferred. In some cases, the affinity reagents may have dissociation constants of about $10^{-3}$ M, $10^{-4}$ M, $10^{-5}$ M, $10^{-6}$ M, $10^{-7}$ M, $10^{-8}$ M, $10^{-9}$ M, $10^{-10}$ M or lower. In some cases the affinity reagents may have dissociation constants of greater than about $10^{-10}$ M, $10^{-9}$ M, $10^{-8}$ M, $10^{-7}$ M, $10^{-6}$ M, $10^{-5}$ M, $10^{-4}$ M, $10^{-3}$ M, $10^{-2}$ M or higher.

Some of the affinity reagents may be chosen to bind modified amino acid sequences, such as phosphorylated or ubiquinated amino acid sequences. In some examples, one or more affinity reagents may be chosen to be broadly specific for a family of epitopes that may be contained by one or more proteins. In some examples, one or more affinity reagents may bind two or more different proteins. In some examples, one or more affinity reagents may bind weakly to their target or targets. For example, affinity reagents may bind less than 10%, less than 10%, less than 15%, less than 20%, less than 25%, less than 30%, less than 35%, or less than 35% to their target or targets. In some examples, one or more affinity reagents may bind moderately or strongly to their target or targets. For example, affinity reagents may bind more than 35%, more than 40%, more than 45%, more than 60%, more than 65%, more than 70%, more than 75%, more than 80%, more than 85%, more than 90%, more than 91%, more than 92%, more than 93%, more than 94%, more than 95%, more than 96%, more than 97%, more than 98%, or more than 99% to their target or targets.

To compensate for weak binding, an excess of the affinity reagent may be applied to the solid support. The affinity reagent may be applied at about a 1:1, 2:1, 3:1, 4:1, 5:1, 6:1, 7:1, 8:1, 9:1 or 10:1 excess relative to the sample proteins. The affinity reagent may be applied at about a 1:1, 2:1, 3:1, 4:1, 5:1, 6:1, 7:1, 8:1, 9:1 or 10:1 excess relative to the expected incidence of the epitope in the sample proteins.

The affinity reagents may also comprise a magnetic component. The magnetic component may be useful for manipulating some or all bound affinity reagents into the same imaging plane or z stack. Manipulating some or all affinity reagents into the same imaging plane may improve the quality of the imaging data and reduce noise in the system.

Substrates/Solid Supports

In some embodiments, peptides may be applied to a functionalized substrate, such as a solid support, to facilitate the affinity reagent selection or screening steps. FIG. 3B shows an example of a solid support with arrayed peptides conjugated to the solid support for use in an affinity reagent characterization screen to determine the effect of flanking sequence on the binding of an affinity reagent to the epitope AAA. In some cases, the target peptides may be directly applied to a solid support. In some cases, the target peptides may be synthesized or grown on a solid support. In some cases, peptides may be synthesized on a solid support such as an array or beads. For example, a peptide array may be manufactured to contain multiple copies of a single peptide sequence at each location on the array. Custom peptide microarrays may also be bought commercially, for example PEPperPRINT.

The substrate may be any substrate capable of forming a solid support. Substrates, such as solid supports, as used herein can refer to any solid surface to which peptides can be covalently or non-covalently attached. Non-limiting examples of solid supports include particles, beads, slides, surfaces of elements of devices, membranes, flow cells, wells, chambers, macrofluidic chambers, microfluidic chambers, channels, microfluidic channels, or any other surfaces. Solid support surfaces can be flat or curved, or can have other shapes, and can be smooth or textured. Solid support surfaces may contain microwells. In some embodiments, a solid support can be composed of glass, carbohydrates such as dextrans, plastics such as polystyrene or polypropylene, polyacrylamide, latex, silicon, metals or metal oxides such as gold or zirconium oxide, or cellulose, and may be further modified to allow or enhance covalent or non-covalent attachment of the oligonucleotides. For example, a solid support surface may be functionalized by modification with specific functional groups, such as maleic or succinic moieties, or derivatized by modification with a chemically reactive group, such as amino, thiol, or acrylate groups, such as by silanization or the binding of compounds comprising phosphate groups. Suitable silane reagents may include aminopropyltrimethoxysilane, aminopropyltriethoxysilane and 4-aminobutyltriethoxysilane. The solid support may be functionalized with N-Hydroxysuccinimide (NHS) functional groups. Glass surfaces can also be derivatized with other reactive groups, such as acrylate or epoxy, using, e.g., epoxysilane, acrylatesilane or acrylamidesilane. The solid support and process for oligonucleotide attachment are preferably stable for repeated binding, washing, imaging and eluting steps. In some examples, the solid support may be a slide or a flow cell. A The spacing of the functional groups on the solid support may be ordered or random. An ordered array of functional groups may be created by photolithography. Functional groups in an ordered array may be located such that each functional group is at least about 10 nm, about 25 nm, about 50 nm, about 100 nm, 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm, or more than about 1000 nm from any other functional group. Functional groups in a random spacing may be provided at a concentration such that functional groups are on average at least about 10 nm, about 25 nm, about 50 nm, about 100 nm, 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm, or more than about 1000 nm from any other functional group.

A substrate, such as a solid support, may be indirectly functionalized. For example, a solid support may be PEGylated and a functional group may be applied to all or a subset of the PEG molecules.

A substrate may comprise any material, including metals, glass, plastics, ceramics or combinations thereof. A substrate may comprise additional layers or materials for various purposes, such as reflective coatings, anti-reflective coatings, passivating groups, or blocking groups. In some preferred embodiments, the solid support can be a flow cell. The flow cell can be composed of a single layer or multiple layers. For example, a flow cell can comprise a base layer (e.g., of boro silicate glass), a channel layer (e.g., of etched silicon) overlaid upon the base layer, and a cover, or top, layer. When the layers are assembled together, enclosed channels can be formed having inlet/outlets at either end through the cover. The thickness of each layer can vary, but is preferably less than about 1700μm. Layers can be composed of any suitable material known in the art, including but not limited to photosensitive glasses, borosilicate glass, fused silicate, PDMS or silicon. Different layers can be composed of the same material or different materials. The materials that comprise a substrate may be chosen to have low levels of autofluorescence or In some embodiments, flow cells can comprise openings for channels on the bottom of the flow cell. A flow cell can comprise millions of attached target conjugation sites in locations that can be discretely visualized. In some embodiments, various flow cells of use with embodiments of the invention can comprise different numbers of channels (e.g., 1 channel, 2 or more channels, 3 or more channels, 4 or more channels, 6 or more channels, 8 or more channels, 10 or more channels, 12 or more channels, 16 or more channels, or more than 16 channels). Various flow cells can comprise channels of different depths or widths, which may be different between channels within a single flow cell, or different between channels of different flow cells. A single channel can also vary in depth and/or width. For example, a channel can be less than about 50μm deep, about 50μm deep, less than about 100μm deep, about 100μm deep, about 100μm to about 500μm deep, about 500μm deep, or more than about 500μm deep at one or more points within the channel. Channels can have any cross-sectional shape, including but not limited to a circular, a semi-circular, a rectangular, a trapezoidal, a triangular, or an ovoid cross-section.

The peptides may be spotted, dropped, pipetted, flowed, washed or otherwise applied to the solid support. In the case of a solid support that has been functionalized with a moiety such as an NHS ester, no modification of the peptide is required. In the case of a solid support that has been functionalized with alternate moieties (e.g. a sulfhydryl, amine, or linker DNA), a crosslinking reagent (e.g. disuccinimidyl suberate, NHS, sulphonamides) may be used. In the case of a solid support that has been functionalized with linker DNA the peptides of the target may be modified with complementary DNA tags.

Photo-activatable cross linkers may be used to direct cross linking of a sample to a specific area on the solid support. Photo-activatable cross linkers may be used to allow multiplexing of peptide samples by attaching each sample in a known region of the solid support. Photo-activatable cross linkers may allow the specific attachment of peptides which have been successfully tagged, for example by detecting a fluorescent tag before cross linking a peptide. Examples of photo-activatable cross linkers include, but are not limited to, N-5-azido-2-nitrobenzoyloxysuccinimide, sulfosuccinimidyl 6-(4'-azido-2'-nitrophenylamino)hexanoate, succinimidyl 4,4'-azipentanoate, sulfosuccinimidyl 4,4'-azipentanoate, succinimidyl 6-(4,4'-azipentanamido)hexanoate, sulfosuccinimidyl 6-(4,4'-azipentanamido)hexanoate, succinimidyl 2-((4,4'-azipentanamido)ethyl)-1,3'-dithiopropionate, and sulfosuccinimidyl azipentanamido)ethyl)-1,3'-dithiopropionate.

The peptides may be attached to the substrate by one or more residues. In some examples, the peptides may be attached via the N terminal, C terminal, both terminals, or via an internal residue.

In some embodiments, each peptide sequence may be associated with a unique spatial address. For example, once the peptides are attached to the solid support in spatially separated locations, each peptide sequence can be assigned an indexed address, such as by coordinates. In some examples, a grid of pre-assigned unique spatial addresses may be predetermined. In some embodiments the solid support may contain easily identifiable fixed marks such that placement of each peptide can be determined relative to the fixed marks of the solid support. In some examples, the solid support may have grid lines and/or and "origin" or other fiducials permanently marked on the surface. In some examples, the surface of the solid support may be permanently or semi-permanently marked to provide a reference by which to locate cross linked peptides. The shape of the patterning itself, such as the exterior border of the conjugated peptides may also be used as fiducials for determining the unique location of each spot.

EXAMPLES

Example 1: Selection Approach

Step 1: Pre-Enrichment Using SELEX

Objective: To compare a set of pre-enrichment approaches for their ability to (1) greatly reduce the diversity of an input library against a peptide target and, (2) yield a low complexity aptamer pool that exhibits properties consistent with the target aptamer profile.

Key actions: In order to narrow the final pool of aptamers for each peptide target, an input library comprising a diversity of approximately $10^{15}$ random library sequences will be used and pre-enrichment will be performed using typical bead-based SELEX. The library designs to be tested may include structured libraries and naïve libraries.

In order to promote the pre-enrichment of targets with a slow off-rate, SELEX incubations in binding buffer between aptamer pool and peptide-bead pool will be performed overnight to allow for slow off-rate binders to compete with fast off-rate binders for bead occupancy. Additionally, a range of successively longer wash times for the bead-peptide complexes post-incubation will be explored to bias the enrichment for slow off-rate binding. The overnight incubation condition will be compared to a 1 hour incubation, resulting in two SELEX tracks: short incubation and long incubation.

In order to promote the pre-enrichment of targets the unbind quickly in the presence of a specific eluate, bound aptamers will be eluted in 10 mM EDTA (or other eluates to be defined) and the eluate will be used to generate the aptamer pool for the next round of SELEX. Material from the remaining beads will be eluted by heat and preserved to allow for the option of exploring alternative elution conditions.

In order to identify a strategy that best promotes the pre-enrichment of targets that bind regardless of the composition of flanking amino acid residues, for both short and long incubation SELEX tracks, four approaches to enrichment will be compared, resulting in a total of eight SELEX tracks:

Pre-enrichment Approach 1: Pre-enrichment SELEX will be performed against a "low stringency" glycine-flanked ("G-flank", GXG) peptide target.

Pre-enrichment Approach 2: Pre-enrichment SELEX will be performed against G-flank peptide target in the first set of SELEX rounds and then a "high stringency" peptide target flanked by a specific set of amino acid residues ("αXβ") in subsequent SELEX rounds.

Pre-enrichment Approach 3: Pre-enrichment SELEX will be performed against αXβ peptide targets in the first set of SELEX rounds and then GXG peptide target in subsequent SELEX rounds. The transition round from high to low stringency will be determined.

Pre-enrichment Approach 4: Pre-enrichment SELEX will be performed against αXβ target peptides only.

After pre-enrichment, progress will be measured using Particle Display. This data will be used to decide on which pre-enriched aptamer pools to carry forward to Step 2. qPCR, flow cytometry, and other data generated may be used to guide the designation of which aptamer pools to select.

As part of the pre-enrichment process, next generation sequencing (NGS) may be performed on all or a subset of SELEX rounds. Library preparation may include multiplexing. Throughout the pre-enrichment process, post-amplification material will be preserved from each SELEX round to serve as a potential aptamer pool for particle display.

Step 2: Particle Display

Objective: Identify collections of sequences that exhibit the target aptamer profile.

Key action: The necessary number of particle display sorting rounds (normally three to five rounds) will be performed on designated pre-enriched aptamer pools to isolate pools of aptamers that exhibit the target aptamer profile. Experimental design during the execution of particle display will be refined to tune the stringency of sorting accordingly. In order to promote the sorting of aptamers that exhibit the target aptamer profile, each particle display round will consist of two sorting steps, producing two aptamer candidate output pools for each input pool. In this step, only αXβ target peptide will be used.

The first sorting step will be designed to promote the enrichment of aptamers exhibiting Property 1. The aptamer pool will be mixed with target peptide labeled with fluorophore 1 and biotin-labeled negative control peptide. Excess bound target and negative control peptide will be allowed to dissociate from aptamer beads for 15 minutes prior to labeling with fluorescent streptavidin and sorting will be gated on high target peptide signal, low negative control peptide signal, and high aptamer signal. This output pool will be amplified and part of the pool will be preserved for NGS.

The second sorting step will be designed to promote the enrichment of aptamers exhibiting Property 2. The remainder of the output pool from the first sorting step will be prepared in the same fashion as the input pool used for the first sorting step except that negative control peptide will be omitted and the pool will be transferred into elution buffer and incubated for 15 seconds before sorting. This pool with be gated on low peptide signal and high aptamer signal. The output will be amplified and part of the pool will be preserved for NGS and the remainder of the pool will be used for the next round of particle display.

Step 3: Sequencing and Aptamer Characterization

Objective: Identify specific sequences and sequence families and confirm that their binding properties meet the target aptamer profile.

Key action: Particle display output pools to be evaluated by NGS will be identified based on the results above. Libraries will be prepared for sequencing and used to generate NGS outputs.

Candidate sequences ("aptamer hits") will be synthesized and/or conjugated to beads and screened for the target aptamer profile as follows:

To score aptamer hits for Property 1, aptamer beads will be mixed with 1 uM fluorescently labeled target peptide for 3 minutes, washed, and diluted to a concentration suitable for flow cytometry analysis. Dissociation rates will then be determined by sampling the mixture over a time course of 1 hour.

To score aptamer hits for Property 2, aptamer beads will be prepared as above except the diluent will be comprised of the elution buffer and the mixture will be sampled within 15 seconds of the addition of diluent or as soon as is technically feasible.

To score aptamer hits for Property 3, aptamer candidates will be scored for Property 1 and Property 2 using G-flank and X-flank peptide targets separately.

Example 2: Implementation Example

Considered in this example are binding measurements of an affinity reagent to a nucleic acid programmable protein array (NAPPA) containing 720 unique proteins with 3-5 replicates each included on the array. In some embodiments, these replicates may be scattered across the array. Binding is assessed by hybridizing a fluorescently-labelled affinity reagent to the array and measuring observed fluorescence at each spot on the array. In this example, the identity of each protein at each spot is known. Accordingly, fluorescence may be mapped to protein identities.

In this example, the protein binding measurement (fluorescence) is modeled as a linear combination of the count of each of the 8000 possible trimers in the protein sequence and the fractional contribution to observed fluorescence attributable to binding of the affinity reagent to that trimer. That is:

$$F_{pr} = \sum_{t=1}^{t=8000} c_{t,pr} \beta_t$$

Where:
$F_{pr}$=Fluorescence for protein pr
$c_{t,pr}$=Count of trimer t in protein pr
$\beta_t$=Fractional fluoresence from binding of affinity reagent to trimer t Measurements for an affinity reagent against multiple proteins form a linear system of equations:

$$\vec{F} = C\vec{\beta} + \epsilon$$

Where:
$\vec{F}$ is a length N column vector containing the observed fluorescence for each protein
C is an N×8000 matrix of trimer counts with each column being counts for a particular trimer in each measured protein
$\vec{\beta}$ is a length 8000 column vector of fractional fluorescence for each possible trimer
$\epsilon$ is a scalar constant to correct for background binding or a noise floor The model described herein may be extended to include non-standard amino acids or model n-mers of different lengths. In the case of known NAPPA or similar binding measurements, $\vec{F}$ and C are known variables and values for $\vec{\beta}$ and $\epsilon$ may be derived by linear regression or related approaches. In particular, non-negative least squares and non-negative least absolute shrinkage and selection operator (LASSO) regression may be well-suited for this problem. Non-negative least squares bounds the solution $\vec{\beta}$ to be non-negative, and non-negative LASSO regression further imposes a sparsity constraint. LASSO regression may be particularly effective when the system is underdetermined, that is, when the number of unique proteins measured is less than the number of unique trimers (8,000 in this example).

Binding to the aforementioned NAPPA array was simulated for an affinity reagent with the following relative affinities:
LAS: 0.75
GEL: 0.05
YIC: 0.001
STK: 0.001
Binding to all other trimers was assigned affinity 0.00001.

Binding to each protein on the NAPPA array was simulated by calculating the expected binding using the described statistical model and aforementioned binding affinities with Gaussian noise applied having a standard deviation of 5% of the expected binding affinity.

From these simulated data, LASSO was used (with the LASSO sparsity parameter α set to 1e-3) to learn the binding affinities of the reagent from the protein binding measurements. The learned affinities were:
LAS 0.750034
GEL 0.040796
ASW 0.012120
SGD 0.005001
QPH 0.003975
LGC 0.003788
KGR 0.002475
VPS 0.002416
EIK 0.002305
SES 0.002149
RIS 0.001235
SSE 0.001067
STS 0.000953
APP 0.000889
HSD 0.000785
KSQ 0.000735
VQK 0.000637
PPT 0.000538

GCS 0.000417
RPR 0.000106
QPQ 0.000051
ACS 0.000026

With all other trimers having an affinity of zero.

This example indicates that the approach is able to build a reasonable estimate of affinity reagent binding albeit with a tolerable amount of noise.

Example 3: Selection of KW Affinity Reagent

Figure 6:
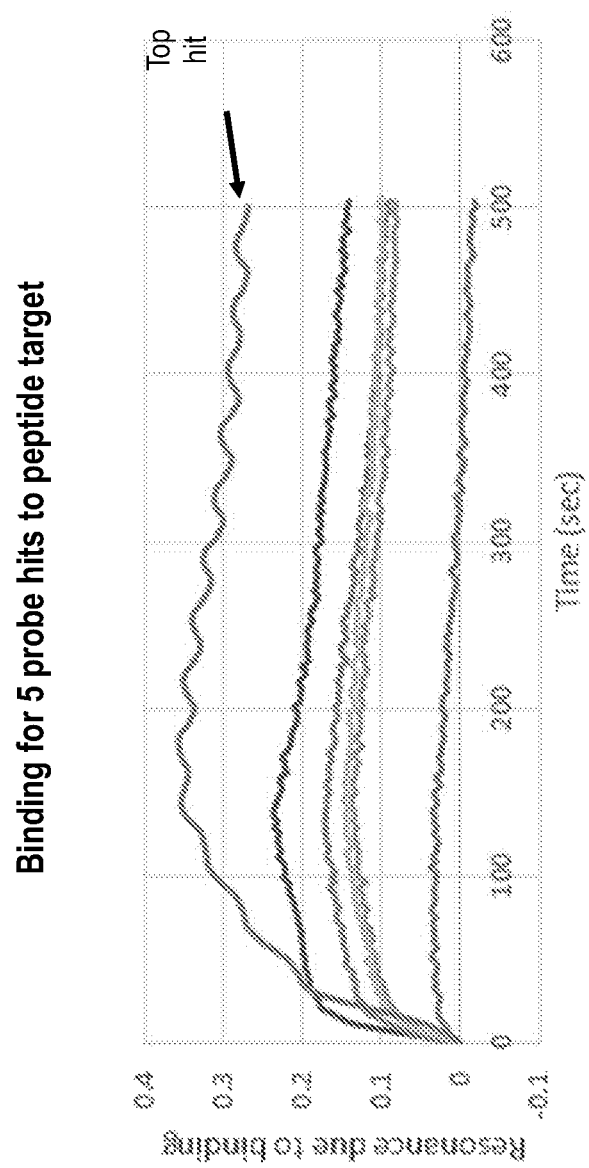
FIG. 6 illustrates target binding of several aptamers identified in an aptamer selection screen, in accordance with some embodiments.
Figure 7:
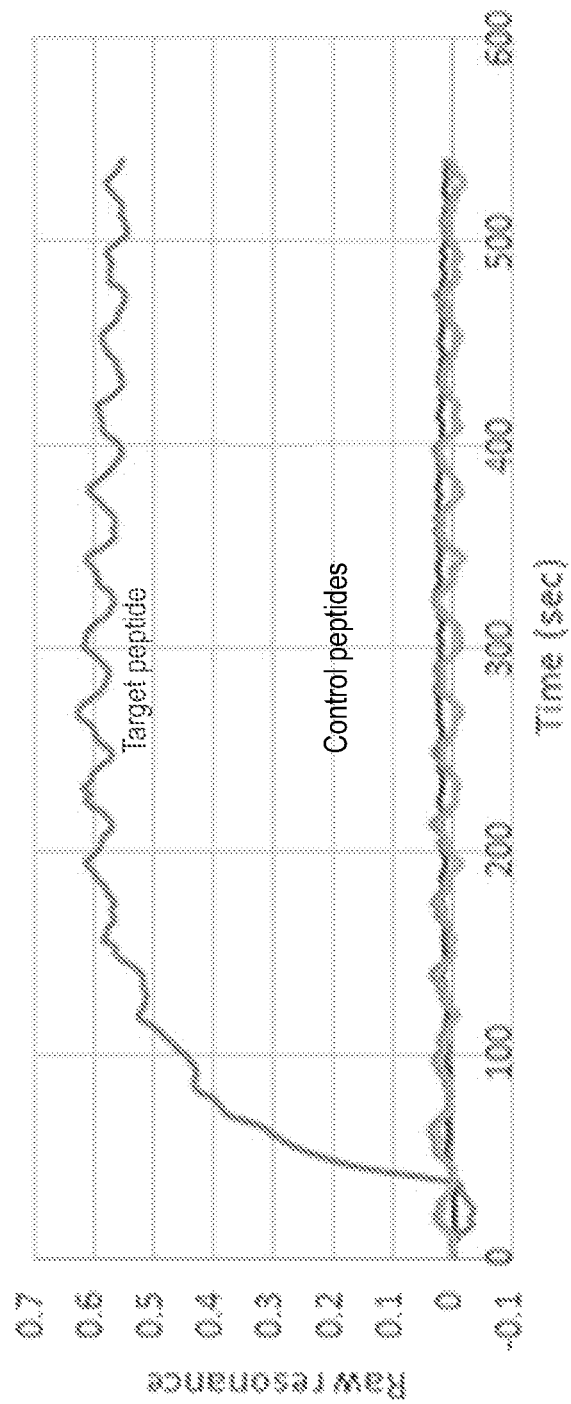
FIG. 7 illustrates preliminary characterization of an identified aptamer, in accordance with some embodiments.

An affinity reagent selection screen was conducted to select aptamers which bound to any of four different target epitopes—KW, LFQ, IRN, and EGE. Array-based surface plasmon resonance imaging selection was used to select aptamers which bound the targets from an aptamer library. Preliminary validation was conducted on aptamers which bound to the target KW. FIG. 6 shows binding of the 5 top hits to the KW target as measured by surface plasmon resonance. FIG. 7 shows binding of the best antiKW aptamer compared to negative control peptides.

Figure 8:
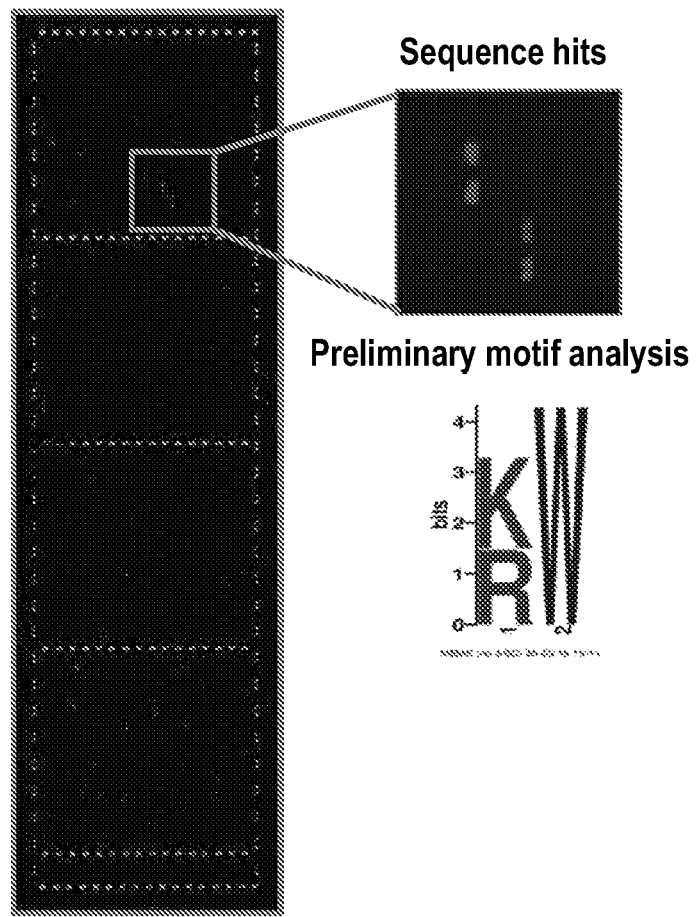
FIG. 8 illustrates preliminary characterization of an identified aptamer, in accordance with some embodiments.

To determine the epitope specificity of the top anti KW aptamer from FIG. 6 the aptamer was fluorescently labeled and applied to a peptide array. Based on the binding of the labeled aptamer to the peptide array the epitopes recognized by the aptamer were determined to be KW and KR with relatively similar affinity for both. The binding data and preliminary motif analysis are shown in FIG. 8.

Example 4: High-Throughput Sequencing Fluorescent Ligand Interaction Profiling

Figure 10:
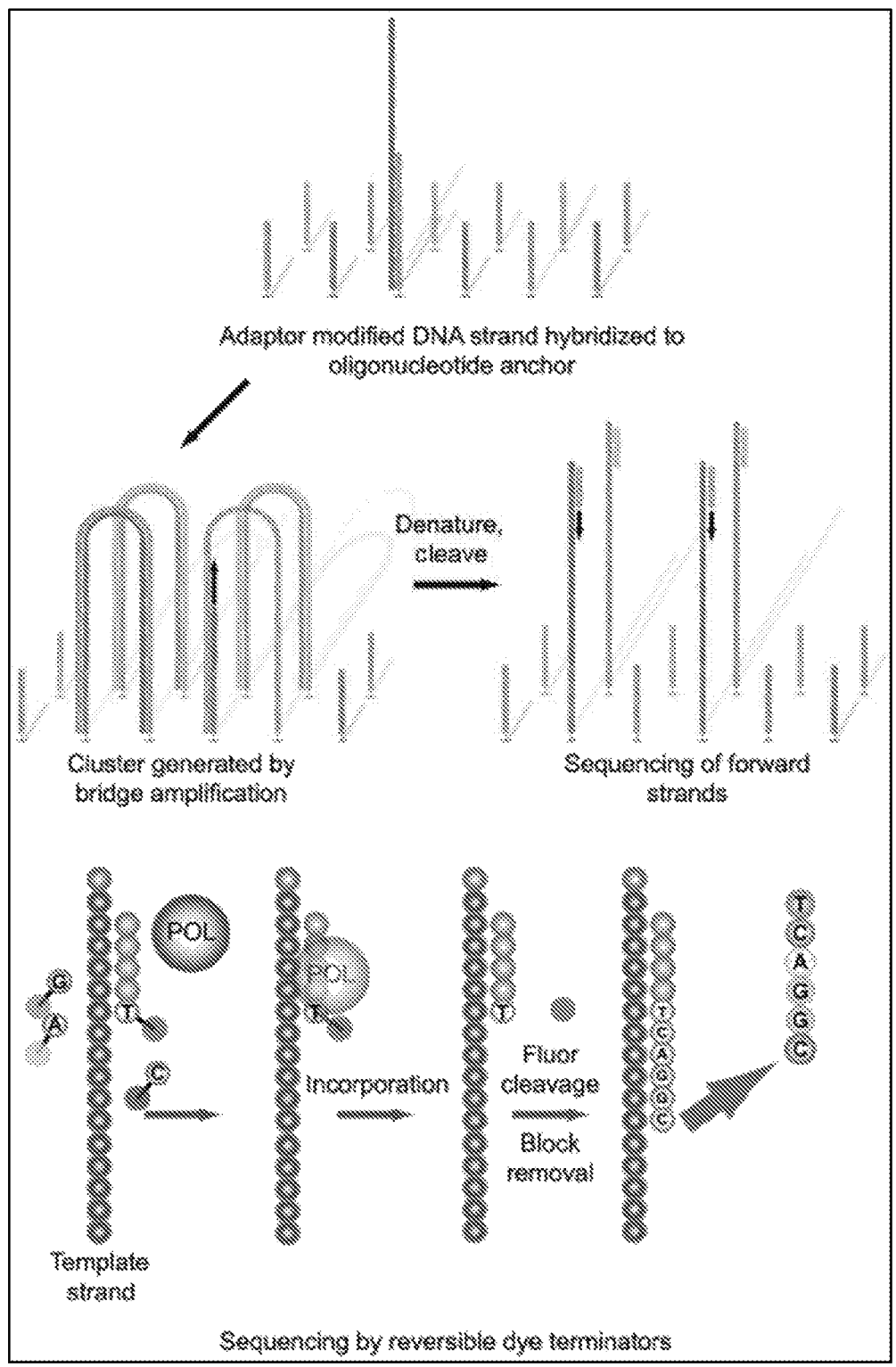
FIG. 10 illustrates an example of cluster amplification, in accordance with some embodiments.
Figure 11:
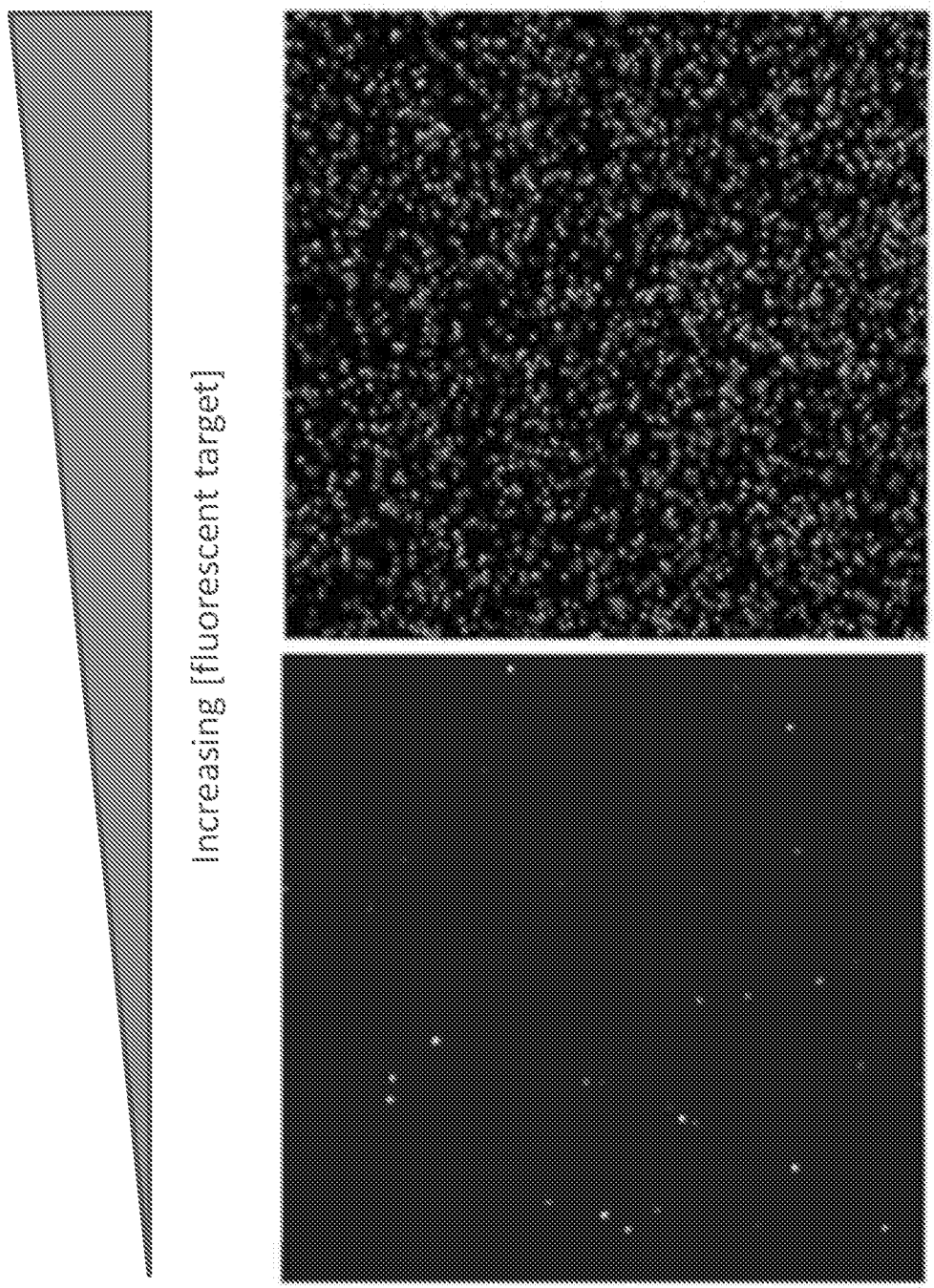
FIG. 11 illustrates binding of a fluorescently labeled peptide target to aptamer clusters on a flow cell, in accordance with some embodiments.
Figure 12:
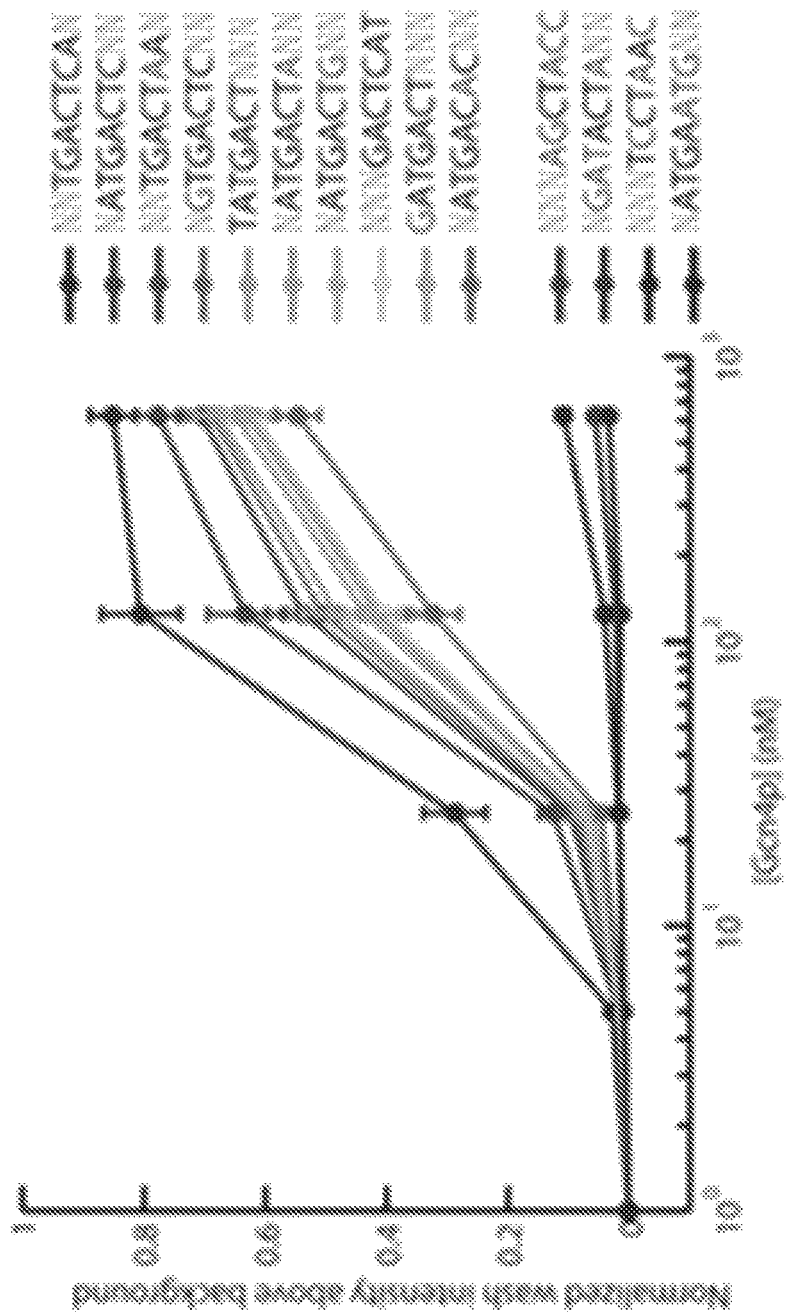
FIG. 12 illustrates binding affinities of several aptamers for a peptide target, in accordance with some embodiments.

A high-throughput sequencing fluorescent ligand interaction profiling assay was conducted by obtaining an aptamer library, and incorporating adapters sequences on both ends of the aptamers of the library. The library of aptamers with adapters was applied to flow cell comprising immobilized oligo primers and cluster amplification was conducted as depicted in FIG. 10. After cluster amplification the clusters (each representing a single aptamer from the aptamer library) were sequenced using reversible dye terminators. The clusters were then denatured to remove the sequencing reagents, washed, and were allowed to fold into their native aptamer conformations. A fluorescently labeled peptide target was applied to the clusters at four different concentrations, and was imaged to show the clusters which bound the fluorescently labeled peptide target. FIG. 11 shows representative images of the flow cell with bound fluorescently labeled peptide target and two different concentrations. The fluorescence data was combined with the sequencing data to provide affinity measurements for each aptamer of the aptamer library represented on the flow cell. FIG. 12 shows sequences and binding affinities of several different aptamers for the fluorescently labeled peptide target (LFQ).

Example 5: Peptide Synthesis and Validation

Materials:

All reagents and solvents were of peptide synthesis grade or highest purity available. Amino acid derivatives were obtained from Aapptech, (Louisville, KY USA) and all solvents for peptide synthesis, SPE and RP±HPLC were obtained from Acros Organics, USA.

Peptide Synthesis:

Peptides were synthesized on MultiPep RSi synthesizer (Intavis, Germany) employing standard Fmoc/tBu chemistry. Amino acid derivatives were activated by N,N,N',N'-Tetramethyl-O-(1H-benzotriazol-1-yl)uronium hexafluorophosphate (HBTU) (0.5M). The standard synthesis protocol employed in the 96-vessel microreaction block to synthesize peptide. Rink Amide Resin (Intavis, Germany) was loaded at 0.53 mmol/g of amine content to 2 micromol per vessel. Following addition sequence was used to synthesize peptides:

| | Resin Preparation | |
|---|---|---|
| 1 | Memo | synthesis scale: 2 μmol |
| 1 | RinseNeedle | 1500/2000 μl (DMF) |
| 2 | Pipet | 1500 μl/1500 μl CapMixture (Acetic Anhydride) -> Drain |
| 3 | RinseNeedle | 1500/2000 ul (DMF) |
| 4 | Pipet | 1500 μl/1500 μl N-methylpiperidine solution -> Drain |
| 5 | RinseNeedle | 1000/2000 μl (DMF) |
| 6 | PrimeManifold | 10000 μl, DMF |
| 7 | WashResin | 1200 μl, DMF, 4× |
| 8 | Extract | 60 s |
| Cycle | | 1. -> N. (count = N) (N—number of couplings) |
| 9 | Deprotection | 50 μl, N-methylpiperidine |
| 10 | Deprotection | 50 μl, N-methylpiperidine |
| 11 | RinseNeedle | 1000/2000 ul |
| 12 | WashResin | 1800 μl, DMF, 2× |
| 13 | WashResin | 1200 μl, DMF, 8× |
| 14 | Extract | 30 s |
| 15 | Coupling | 20 μl HBTU + 5 μl NMM + 2 μl NMP + 21 μl Amino-acid derivative |
| 16 | Coupling | 20 μl HBTU + 5 μl NMM + 2 μl NMP + 21 μl Amino-acid derivative |
| 17 | Capping | 50 μl, CapMixture (Acetic Anhydride) |
| 18 | RinseNeedle | 1000/2000 ul (DMF) |
| 19 | WashResin | 1200 μl, DMF, 6× |
| 20 | Extract | 60 s |
| Final Action | | |
| 21 | Deprotection | 80 μl, N-methylpiperidine |
| 22 | Deprotection | 80 μl, N-methylpiperidine |
| 23 | Deprotection | 80 μl, N-methylpiperidine |
| 24 | RinseNeedle | 500/2500 ul (DMF) |
| 25 | WashResin | 1800 μl, DMF, 2× |
| 26 | WashResin | 1200 μl, DMF, 8× |
| 27 | PrimeManifold | 10000 μl, Ethanol |
| 28 | WashResin | 1200 μl, Ethanol, 2× |
| 29 | Extract | 300 s |
| 30 | RinseNeedle | 1000/3000 ul (DMF) |

All amino-acid derivatives were used as 0.5M solutions in DMF, except of Fmoc-Lysine(Biotin) (0.3M).

N-methylpiperidine was used as 2M solution in DMF, Acetic anhydride was used as 5% solution in DMF (0.529M). Coupling continued for 30 min for each cycle and repeated 2 times for each building block. Amino-acid was used in 10× excess over amine to ensure complete coupling. Peptides were cleaved with a solution of 5% water, 2.5% Triisopropylsilane in trifluoroacetic acid (TFA) at room temperature for 2 h, precipitated with tert-butyl methylether at −20 C and washed three times with cold tert-butyl methylether (200 ul). The dried peptides were dissolved in 1 mL of 0.1% aqueous TFA (500 microliters) and stored at −20 C.

Solid-Phase Extraction

The crude peptides were purified on a Sep-Pak C18 Multi 96-well plate (WAT054955) containing 40 mg of C18 sorbents in each well using the Multi 96 vacuum manifold (Waters, USA). The eluates were collected in 2 mL collection racks (WAT058956). In a typical protocol, the cartridge or plate was washed with 1 ml of MeOH, and conditioned with 0.1% aqueous TFA before loading the peptide sample.

Peptides were loaded by passing the solution slowly through the stationary phase without vacuum to accomplish near quantitative peptide binding. The solid phase was washed with 0.1% aqueous TFA to remove salts and other polar impurities, before the bound peptides were eluted with 1 mL of 70% aqueous acetonitrile. Solvent was evaporated using Centrivap overnight and pellet was re-dissolved in 500 microliters of DI water. Concentration was measured using Tecan Spark plate reader using water as blank and collecting absorption spectra in the range of 200 to 1000 nm. Absorption and extinction coefficient at 214 nm was used to calculate concentration of peptide. UV transparent 96-well plates (ThermoFisher 8404) were used to measure the concentration of peptides.

Figure 9:
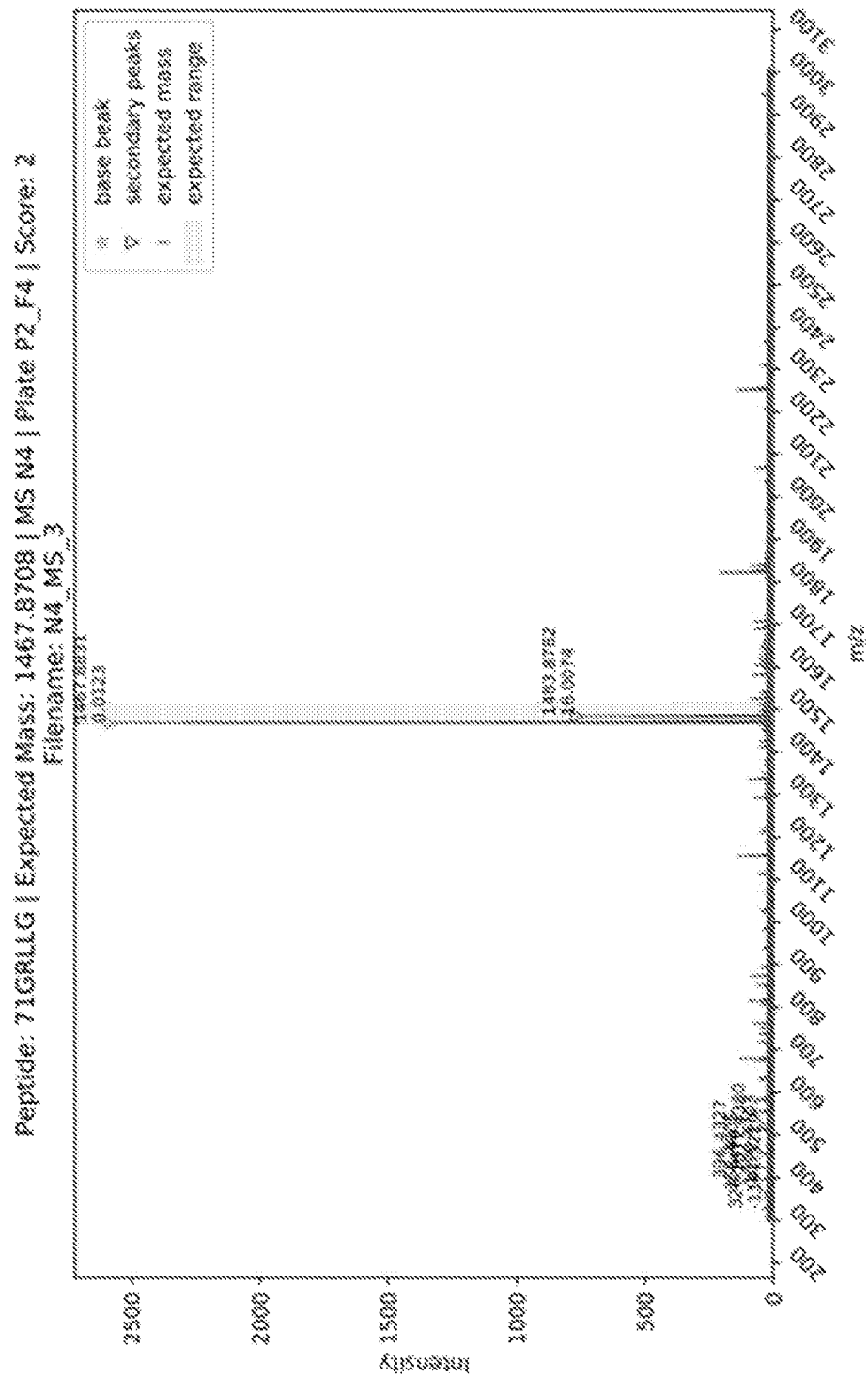
FIG. 9 illustrates Mass Spectrometry verification of a synthesized peptide, in accordance with some embodiments.

Mass-Spectrometry:

Matrix solution was purchased from Agilent Technologies (Cat #G2037A). Samples were prepared by co-spotting 1 microliter of peptide stock solution and 1 microliter of matrix on the MALDI sample plate and letting the sample dry under ambient conditions. Mass spectra were recorded on a MALDI-TOF mass-spectrometer AB SCIEX 5800 TOF/TOF. A representative Mass spectra is shown in FIG. 9.

Example 6: Affinity Reagent SELEX Selection with Magnetic Bead Peptide Libraries Peptide Conjugation on Alkyne Magnetic Beads Conjugation solutions for alkyne magnetic beads were prepared. A first solution of 0.01% Tween20 (5 mL water+ 0.5 μL Tween20) was prepared. A second solution of 100 mM $CuSO_4 \cdot 5H_2O$ (MW: 249.69 g/mol) was prepared from 25 mg of $CuSO_4 \cdot 5H_2O$ dissolved in 1 mL of water. 500 mM sodium ascorbate (MW: 198.11 g/mol) was prepared by dissolving 100 mg of sodium ascorbate in 1 mL of water.

Stock alkyne magnetic beads were washed. Each sample used 5 μL of beads as supplied. Beads were resuspended in a stock vial by vortex for >30 sec, or tilting and rotation for 5 min. Beads were removed from the stock vial and pulled down using a magnetic tube rack and removing the supernatant. 1 mL of 0.01% Tween20 was added to the beads, and the beads were resuspended then pulled down using a magnetic tube rack, followed by removal of the supernatant. Rinsing in the Tween 20 was repeated 4 more times. The washed beads were resuspended in 0.01% Tween20.

Peptide were conjugated to the alkyne magnetic beads as follows. Each aliquot of magnetic beads (200 μL beads) were combined with 100 nmol of prepared peptide, 20 μL of 100 mM $CuSO_4 \cdot 5H_2O$ (20 fold of the number of alkyne groups), 20 μL of 500 mM sodium ascorbate (100 fold of the number of alkyne groups), and enough 0.01% Tween20 to bring the reaction volume to 1000 μL. Combined peptide-bead mixtures were allowed to shake in a Thermomixer for 16 hours. After mixing, conjugated beads were pulled down. Supernatant was removed and saved to measure peptide concentration on a protein analyzer. Beads were washed twice with 0.01% tween20 and then resuspended in 0.01% Tween20.

SELEX Selection of Affinity Reagents

Libraries were pre-enriched against the peptide target for three rounds prior to SELEX. In pre-enrichment round (PE R)1, the affinity reagent library was eluted with heat in water. Prior to PE R2 and R3 another 125 pmol naïve library will be added to the heat elution product.

Part 1: Preparation of Buffers for SELEX:

Buffers for SELEX selection were prepared. 1 L of 20× stock of NVT [200 mM HEPES, 2.4 M NaCl, 100 mM $MgCl_2$, 100 mM KCl, 2% Tween20 pH 7.4] was prepared by dissolving 47.66 g HEPES (MW 238.30 g/mol), 140.256 g NaCl (MW 58.44 g/mol), 9.5211 g $MgCl_2$ (MW 95.211 g/mol), and 7.455 g KCl (MW 74.55 g/mol) in 750 mL of water. The pH was adjusted to 7.4 using HCl/NaOH. 20 mL of Tween20 was added to the solution, then the final volume was brought to 1 L. Binding buffer was prepared with 1×NVT with 300 uM dextran sulfate and 0.1 mg/ml sheared salmon sperm DNA. The wash buffer for SELEX was 1× NVT.

Part 2: Preparation of Library for SELEX:

Intermediate library stock was prepared in 1×NVT. The library was heated to 95° C. for 5 mins and then cooled for 10 mins Part 3: Peptide Bead Washing and Library Binding:

5 multiwell wash plates with 2004 μL 1×NVT were created. 1 multiwell bead plate was loaded with 40 μL of beads per well from the bead peptide stock microcentrifuge tubes (54 beads from original stock plate) and then combined with t0 160 μL 1×NVT per well. Combs were added to this plate. 1 multiwell library plate with 100 pmol heated naïve library in 200 μL 1× binding buffer per well was generated. 1 standard plate with 50 μL water per well was created.

Beads were collected from the bead plate 3 times for 20 seconds per collection. Beads were washed in the wash plate 1 by release the beads for 10 sec, mixing for 30 sec, and collecting the beads 5× for 30 sec each collection. This washing method was repeated in wash plate 2. Beads were moved to the library plate for library binding by releasing the beads for 10 sec, binding for 6 rounds of fast mixing for 9 min 30 sec plus slow mixing for 30 sec, then collecting beads for 5 rounds of 30 sec. Beads were then washed 3 times (wash plate 3, 4, and 5) by releasing the beads for 10 sec, washing 2× by medium mixing for 4 min 30 sec plus slow mixing for 30 sec, then collecting beads for 2 rounds of 30 sec. Beads were eluted in water by releasing the beads for 14 sec, mixing at medium speed for 30 sec and slow mixing for 30 sec, then collecting the beads for 2 rounds of 21 sec. Beads were transferred back to the bead plate. The heat elution plate was collected and its contents transferred to a PCR plate for storage prior to the next round.

SELEX (6 Rounds)

SELEX was carried out against long and short peptides using naïve and pre-enriched affinity reagent libraries. The elution for the first 2 rounds was split into two groups: EDTA and peptide competition elution. Round 3 onwards all samples were eluted with EDTA. All rounds include a second heat elution.

Part 1: Preparation of Library for SELEX:

Intermediate library stock was prepared in 1×NVT. The library was heated to 95° C. for 5 mins and then cooled for 10 mins.

Part 2: Peptide Bead Washing and Library Binding:

Bead washing was carried out on a MagMax. 5 multiwell wash plates were generated with 200 μL 1×NVT per well. 1 multiwell bead plate was generated with 16 μL beads from the bead peptide stock microcentrifuge tubes (5 μL beads from original stock plate) and filled with t0 160 μL 1×NVT. Combs were added to this plate. 1 multiwell library plate was generated with 100 pmol in 50 μL heated naïve affinity reagent library or 50 μL of pre-enriched affinity reagent library in 134 μL 1× binding buffer. 16 μL of beads were added to the appropriate wells. 1 standard plate was generated with 50 μL EDTA in the appropriate wells. The remaining wells with were filled with water. 1 standard plate was generated with 50 μL peptide (500 pmol) in 1×NVT in the appropriate wells. The remaining wells were filled with 1×NVT. 1 standard plate was generated with 504 water.

Beads were collected from the bead plate 3× for 20 sec. Beads were washed in the wash plate 1 by releasing the beads for 10 sec, medium mixing for 30 sec, then collecting beads for 5× for 30 sec. The washing was repeated in wash plate 2. Beads were moved to the library plate for library binding by binding 6× (medium mixing for 9 min 30 sec plus slow mixing for 30 sec), the collect the beads 5× for 30 sec. Beads were washed three times (wash plate 3, 4, and 5) by release beads for 10 sec, washing 2× (medium mixing for 4 min 30 sec plus bottom mixing for 30 sec), then collect the beads for 2× for 30 sec. For elution in EDTA, the beads were released for 14 sec, followed by mixing at medium for 30 sec and slow mixing for 30 sec and collecting beads 2× for 21 sec. For eluting in peptide, the beads were released for 14 sec, followed by medium mixing for 3× for 4 min 30 sec and slow mixing for 30 sec, then collecting the beads for 2× for 21 sec. For elution in water, beads were released for 14 sec, followed by medium mixing for 30 sec and slow mixing for 30 sec, then collecting beads 2× for 21 sec. Beads were transferred back to the library binding plate. Liquids were collected from all elution plates and the contents transferred to a PCR plate for storage. The EDTA and peptide elution products were combined into a single plate for PCR amplification.

Part 3: Amplification of SELEX Output

Contents were transferred from a Peptide/EDTA plate to a qPCR plate. Two different mastermixes (One for EDTA elution & one for peptide elution) were prepared. The mastermix for EDTA elution was prepared in a total volume of 100 µL by combining 2× Kapa HiFi 100×1/2=50 µL, fwd primer 100×1/500=0.2 µL, rev primer 100×1/500=0.2 µL, SyBr green 100×1/100=1 µL, MgCl2 100×4.5/500=0.9 µL, EDTA elution=45 µL (For round 1), and 2.7µ water. The mastermix for peptide elution was generated by combining 2× Kapa HiFi 100×1/2=50 µL, fwd primer 100×1/500=0.2 µL, rev primer 100×1/500=0.2 µL, SyBr green 100×1/100=1 µL, EDTA 100×2.5/100=2.5 µL, peptide elution=45 µL (For round 1), and Water 1.1 µL of water. A TissueLyser was used 3 times to mix the plate. The plate was centrifuged at 2000×g for 1 min. A qPCR program was run with a thermal cycle of 98 C for 3 min, the 10 cycles of 98 C for 15 s, 65 C for 30 s, and 72 C for 30 s.

One mastermix for both elutions was created and add 100 µL, added to each sample. The total PCR volume was 200 µL. The mastermix was created by combining 2× Kapa HiFi 100×1/2=50 µL, fwd primer 100×1/500=0.2 µL, rev primer 100×1/500=0.2 µL, SyBr green 100×1/100=1 µl, and 48.6 µL, of water. The number of PCR cycles each sample required to reach 1000000-1250000 FLU was recorded. Depending on where the positive control sample peak plateaus, 24 samples were selected including NTC to run on a bioanalyzer to check amplicon size as well as concentration to ensure enough material had been generated for the subsequent round. If insufficient amplicons were detected, the sample was reamplified with PCR for an additional round to remove bubble formation as well as generate more material.

Part 4: Library Re-Generation

A 2× binding and wash buffer (B&W buffer) was generated by combining 10 mM Tris-HCl, 1 mM EDTA, and 2 M NaCl and bringing the solution to a pH of 7.5. The amount of beads needed was calculated as 75 µl of beads needed for a 300 µl PCR reaction. The amount of NaOH needed was calculated as 80 µl of 20 mM NaOH needed per 75 µl of beads. Beads were washed manually in 1× B& W buffer. Create 2 multiwell wash plates were created with 200 µL 1×B&W per well. 1 multiwell bead plate was generated with 75 µL, beads and add to 125 µL 1×B&W. Add combs to this plate. 1 multiwell library plate was created with 300 µL PCR reaction and 300 µL 2× B&W buffer. 1 standard plate was created with 80 µL NaOH in the appropriate wells. The remaining wells were filled with water. 1 PCR collection plate was generated with 20 µL 40 mM HCL and 5 µL 20×NVT. Combs were removed from the bead plate. Beads were mixed with the affinity reagent library in the library plate for library binding as follows by binding: 4× (medium mixing for 4 min 55 sec plus slow mixing for 5 sec) and collecting the beads 5× for 30 sec. Beads were washed two times (wash plate 1 and 2), by releasing the beads for 10 sec, washing the beads for 10 sec, and collecting the beads 5× for 30 sec. Peptides were denatured in NaOH by releasing them for 10 sec, mixing at medium speed for 10 min and slow mixing for 5 sec, then collecting the beads 5× for 30 sec. Combs were replaced in the bead plate.

All samples were quantified using an Oligreen assay. Oligreen standard was diluted to 2 ng/µL in 1×NVT. A 2-fold dilution of standard was performed in a black 96-well plate (the final volume was 100 µL). 2 µL of ssDNA was added to the plate. (the final volume was 100 µL). The 200× Oligreen reagent was diluted to 1×. 100 µL of 1× Oligreen reagent was added to each well on the plate. Readings were taken on a TecanF200 at 485 (20) nm/535 (25) nm before proceeding to the next round of selection.

Example 7: Cobalt SELEX Affinity Reagent Selection

Preparation of Buffers for Cobalt Agarose Beads

Buffers were prepared for agarose bead-based SELEX. 1 L of 20× stock of NVT was prepared [200 mM HEPES, 2.4 M NaCl, 100 mM MgCl2, 100 mM KCl, 2% Tween20 pH 7.4] by dissolving 47.66 g HEPES (MW 238.30 g/mol), 140.256 g NaCl (MW 58.44 g/mol), 9.5211 g MgCl2 (MW 95.211 g/mol), and 7.455 g KCl (MW 74.55 g/mol) in 750 mL of water and adjusting the pH to 7.4 using HCl/NaOH. 20 mL of Tween20 was added and the final volume was brought to 1 L. Binding buffer was prepared by mixing 1×NVT with 300 µM dextran sulfate and 0.1 mg/ml sheared salmon sperm DNA.

Preparation of Library

Intermediate library stock was prepared in 1×NVT. The library was heated to 95° C. for 5 mins and then cooled for 10 mins.

Pre-Enrichment (3 Rounds)

Libraries were pre-enriched against the peptide target for three rounds prior to SELEX round 1. In pre-enrichment round (PE R)1 library were eluted with heat in water. Prior to PE R2 and R3 another 125 pmol naïve library was added to the heat elution.

Initial Washing of Stock Cobalt Agarose Beads

The number of beads needed was calculated as 104 of beads per sample at a bead concentration of 10 mg/ml. The beads were resuspended in the vial by vortexing for >30 sec, or tilting and rotating for 5 min. Beads were removed from the stock vial and added to 1.5 mL microcentrifuge tube. 10 µL of beads was added to the wells of the 96-well filter plate. The 1.5 mL microcentrifuge tube was vortexed between additions to ensure agarose beads were suspended properly. 200 µL 1×NVT was added to each well. The plate was spun for 2 min at 1000×g. This was repeated 2× and the collection plate was emptied.

Peptide Immobilization

200 μL of 1 μM peptide was added to the wells. Plates were shaken for 1 hour. Plates were then centrifuged for 2 min at 1000×g and the collection plate was emptied. 200 μL of 1× NVT was added to each well. The plate was centrifuged for 2 min at 1000×g. The immobilization procedure was repeated 2 more times and the collection plate was emptied.

Positive Selection Against Beads 125 pmol of affinity reagent library was prepared in NVT binding buffer. 200 μL of library in NVT binding buffer was added into each well. The plate was shaken for 1 hour. The plate was centrifuged for 2 min at 1000×g and the collection plate was emptied. Add 200 μL 1× NVT was added to each well. The plate was centrifuged for 2 min at 1000×g, then shaken for 10 minutes. The plate was centrifuged for 2 min at 1000×g and the collection plate was emptied. This procedure was repeated 2 more times. The collection plate was replaced with a clean collection plate. 50 μL of water at 95° C. was added to each well. The plate was shaken for 3 minutes at 70° C. The plate was centrifuged for 2 min at 1000×g.

SELEX (6 Rounds)

SELEX was carried out against long and short peptides using naïve and pre-enriched libraries. The elution for the first 2 rounds was split into two groups: salt free and peptide competition elution. Round 3 onwards all samples were eluted with heat.

Part 1: Initial Washing of Beads for SELEX

The number of beads needed was calculated as 10 μL of beads per sample at a bead concentration of 10 mg/ml. The beads were resuspended in the vial by vortexing for >30 sec, or tilting and rotating for 5 min. Beads were removed from the stock vial and added to 1.5 mL microcentrifuge tube. 10 μL of beads was added to the wells of the 96-well filter plate. The 1.5 mL microcentrifuge tube was vortexed between additions to ensure agarose beads were suspended properly. 200 μL 1×NVT was added to each well. The plate was spun for 2 min at 1000×g. This was repeated 2× and the collection plate was emptied.

Part 2: Peptide Immobilization

200 μL of 1 μM peptide was added to the wells. Plates were shaken for 1 hour. Plates were then centrifuged for 2 min at 1000×g and the collection plate was emptied. 200 μL of 1× NVT was added to each well. The plate was centrifuged for 2 min at 1000×g. The immobilization procedure was repeated 2 more times and the collection plate was emptied.

Part 3: Positive Selection Against Beads

190 μL of NVT binding buffer was added into each well of the plate. 10 μL of library was added into each well and the plate was shaken for 1 hour. The plate was centrifuged for 2 min at 1000×g and the collection plate was emptied. 200 μL of 1×NVT was added to each well and the plate was shaken for 10 minutes. This was repeated 2 more times. 50 μl of 5 μM peptide was added to the peptide elution wells. The plate was shaken for 14 minutes. 50 μL of elution buffer was added to the wells and the plate was shaken for 1 minute. The collection plate was replaced with a clean collection plate and centrifuged for 2 min at 1000×g. The collection plate was replaced with a clean collection plate and 50 μL of water at 95° C. was added to each well. The plate was shaken for 3 minutes at 70° C. The plate was centrifuged for 2 min at 1000×g.

Part 4: Amplification of SELEX Output

Contents were transferred from the Peptide/Salt Free plate to a qPCR plate. Two different mastermixes were prepared (one for EDTA elution & one for peptide elution). The mastermix for elution was prepared by combining Kapa HiFi Mastermix (1× final), F-primer/R-bio primer (1 uM final), SYBR Green (1× final), EDTA (4 mM final), 40 ul of SELEX elution, and water to the final volume. A TissueLyser was used 3 times to mix each sample. The plate was centrifuged at 2000×g for 1 min. Each sample was amplified for 10 cycles. 100 μl of the mastermix was added to each sample. The number of PCR cycles each sample requires to reach 1000000-1250000 FLU was recorded. Depending upon where the positive control sample peak plateaued, 12 samples including NTC were chosen to run on a bioanalyzer to check amplicon size as well as concentration to ensure enough material has been generated for the subsequent round of SELEX.

Part 5: Library Re-Generation

2× binding and wash buffer (B&W buffer) was prepared by combining 10 mM Tris-HCl, 1 mM EDTA, and 2 M NaCl, and adjusting the solution pH to 7.5. The amount of magnetic beads needed was calculated as 75 μl of beads needed for a 300 μl PCR reaction. The amount of NaOH needed was calculated as 80 μl of 20 mM NaOH needed per 75 μl of beads.

The magnetic beads (50 μL beads×number of 100 μL PCR reactions) were washed in 1 mL of 1× B&W buffer. The beads were pulled down using a magnetic tube rack and the buffer was removed. The beads were washed in the same volume of beads. The buffer was removed, and washing was repeated. An equal volume of 2× B&W buffer was added to the beads Samples were run on a MagMAX protocol. Combs sitting in 200 μl B&W were picked up from Combs at a 0 μl volume in the deep well plate. Combs were used to mix the beads and library for 20 min at RT. 100 μL of PCR reaction was combined with 100 μL of beads in 2× B&W buffer for a total volume of 200 μl in the deep well plate. Each well was medium mixed for 10 seconds, then medium mixed for 4 min 50 seconds, then slow mixed for 10 seconds. The procedures was repeated 2 times.

The Dynabeads with bound library were collected and transferred to Wash 1. Each well had a 200 μl volume in the deep well plate and was medium mixed for 10 seconds. Dynabeads with bound library were collected and transferred to Wash 2. Each well had a 200 μl volume in the deep well plate and was medium mixed for 10 seconds. Dynabeads with bound library were collected and transferred to the NaOH plate for elution in 20 mM NaOH. Each well had an 80 μl volume in the deep well plate and was medium mixed for 10 min. Dynabeads free of library were collected and transferred to Combs plate for release. NaOH elution contents were transferred to a PCR plate and 5 μl 20× NV buffer and 20 μl 40 mM HCl was added. pH was checked using pH paper (pH 7.2-7.4). A few samples were selected to check their size on SYBR Gold 2% EX gel. All samples were quantified using an Oligreen assay. Oligreen standard was diluted to 2 ng/μL in 1×NVT. A 2-fold dilution of standard was performed in a black 96-well plate (the final volume was 100 μL). 2 μL of ssDNA was added to the plate. (the final volume was 100 μL). The 200× Oligreen reagent was diluted to 1×. 100 μL of 1× Oligreen reagent was added to each well on the plate. Readings were taken on a TecanF200 at 485 (20) nm/535 (25) nm before proceeding to the next round of selection.

Example 8: Free Solution SELEX Protocol

Pre-Enrichment (3 Rounds)

Libraries were pre-enriched against the peptide target for three rounds prior to SELEX round 1. In pre-enrichment round (PE R)1, the library was eluted with heat in water. Prior to PE R2 and R3 another 125 pmol naïve library was added to the heat elution.

Part 1: Preparation of Buffers for SELEX

Buffers were prepared for agarose bead-based SELEX. 1 L of 20× stock of NVT was prepared [200 mM HEPES, 2.4 M NaCl, 100 mM MgCl2, 100 mM KCl, 2% Tween20 pH 7.4] by dissolving 47.66 g HEPES (MW 238.30 g/mol), 140.256 g NaCl (MW 58.44 g/mol), 9.5211 g MgCl2 (MW 95.211 g/mol), and 7.455 g KCl (MW 74.55 g/mol) in 750 mL of water and adjusting the pH to 7.4 using HCl/NaOH. 20 mL of Tween20 was added and the final volume was brought to 1 L. Binding buffer was prepared by mixing 1×NVT with 300 µM dextran sulfate and 0.1 mg/ml sheared salmon sperm DNA.

Part 2: Preparation of Library

Intermediate library stock was prepared in 1×NVT. The library was heated to 95° C. for 5 mins and then cooled for 10 mins.

Part 3: Library Binding to Peptide Target in Solution 100 pmol of peptide was prepared in 250 µL binding buffer in a MagMAX deepwell plate. 125 pmol of barcoded library was added according to the plate map and plates were shaken for 1 hour at room temperature. During incubation, 10 µL agarose streptavidin beads were taken per well (cut the tip of the pipette tip). Samples were spun in a microcentrifuge tube at 500×g for 1 min. The supernatant was removed and the volume recorded. Samples were washed twice with 1 ml of 1×NVT. Beads were resuspended in the same volume of 1×NVT as the original supernatant so that the total volume was 10× the number of wells. 10 µL of washed beads was added to each well of an empty 96 well microspin column and the membrane and beads were washed with 40 µL binding buffer. The plate was centrifuged at 1000×g for 2 mins. The peptide library mix was combined with the beads and incubated for 10 mins with shaking. The plate was centrifuged at 1000×g for 2 mins and the wells were washed with 250 µL 1×NVT for 10 mins at room temperature. The plate was centrifuged at 1000×g for 2 mins and the wash was repeated twice more. During washes the tube thermomixer was set to 95c and the plate thermomixer to 70 c. 4 ml of water was heated in the tube thermomixer, then 50 µL of heated water was added to each well. Wells were incubated with mixing for 3 min on the plate thermomixer at 70 c. The filter plate was fit with a new collect plate and centrifuged to collect flow through. The contents were transferred to a PCR plate for storage SELEX (6 Rounds)

SELEX was carried out against long and short peptides using naïve and pre-enriched libraries. The elution for the first 2 rounds was split into two groups: EDTA and peptide competition elution. Round 3 onwards all samples were eluted with EDTA. All rounds included a second heat elution.

Part 1: Preparation of Library for SELEX

The library was heated to 95° C. for 5 mins and then cooled for 10 mins. Part 2: Library binding to peptide target in solution 100 pmol of peptide was prepared in 250 µL binding buffer in a MagMAX deepwell plate. 125 pmol of barcoded library was added according to the plate map and plates were shaken for 1 hour at room temperature. During incubation, 10 µL agarose streptavidin beads were taken per well (cut the tip of the pipette tip). Samples were spun in a microcentrifuge tube at 500×g for 1 min. The supernatant was removed and the volume recorded. Samples were washed twice with 1 ml of 1×NVT. Beads were resuspended in the same volume of 1×NVT as the original supernatant so that the total volume was 10× the number of wells. 10 µL of washed beads was added to each well of an empty 96 well microspin column and the membrane and beads were washed with 400 µL binding buffer. The plate was centrifuged at 1000×g for 2 mins. The peptide library mix was combined with the beads and incubated for 10 mins with shaking. The plate was centrifuged at 1000×g for 2 mins and the wells were washed with 250 µL 1×NVT for 10 mins at room temperature. The plate was centrifuged at 1000×g for 2 mins and the wash was repeated twice more. During washes the tube thermomixer was set to 95 c and the plate thermomixer to 70 c. 4 ml of water was heated in the tube thermomixer, then 50 µL of heated water was added to each well. Wells were incubated with mixing for 3 min on the plate thermomixer at 70 c. The filter plate was fit with a new collect plate and centrifuged to collect flow through. The contents were transferred to a PCR plate for storage Part 3: Amplification of SELEX Output Contents were transferred from a Peptide/EDTA plate to a qPCR plate. Two different mastermixes (One for EDTA elution & one for peptide elution) were prepared. The mastermix for EDTA elution was prepared in a total volume of 100 µL by combining 2× Kapa HiFi 100×1/2=50 µL, fwd primer 100×1/500=0.2 µL, rev primer 100×1/500=0.2 µL, SyBr green 100×1/100=1 MgCl2 100×4.5/500=0.9 µL, EDTA elution=45 µL (For round 1), and 2.7µ water. The mastermix for peptide elution was generated by combining 2× Kapa HiFi 100×1/2=50 µL, fwd primer 100×1/500=0.2 µL, rev primer 100×1/500=0.2 µL, SyBr green 100×1/100=1 µL, EDTA 100×2.5/100=2.5 µL, peptide elution=45 µL (For round 1), and Water 1.1 µL of water. A TissueLyser was used 3 times to mix the plate. The plate was centrifuged at 2000×g for 1 min. A qPCR program was run with a thermal cycle of 98 C for 3 min, the 10 cycles of 98 C for 15 s, 65 C for 30 s, and 72 C for 30 s. Each sample was amplified for 10 cycles.

One mastermix for both elutions was created and add 100 µL added to each sample. The total PCR volume was 200 µL. The mastermix was created by combining 2× Kapa HiFi 100×1/2=50 fwd primer 100×1/500=0.2 µL, rev primer 100×1/500=0.2 µL, SyBr green 100×1/100=1 µL, and 48.6 µL of water. The number of PCR cycles each sample required to reach 1000000-1250000 FLU was recorded. Depending on where the positive control sample peak plateaus, 24 samples were selected including NTC to run on a bioanalyzer to check amplicon size as well as concentration to ensure enough material had been generated for the subsequent round. If insufficient amplicons were detected, the sample was reamplified with PCR for an additional round to remove bubble formation as well as generate more material.

Part 4: Library Re-Generation

A 2× binding and wash buffer (B&W buffer) was generated by combining 10 mM Tris-HCl, 1 mM EDTA, and 2 M NaCl and bringing the solution to a pH of 7.5. The amount of beads needed was calculated as 75 µl of beads needed for a 300 µl PCR reaction. The amount of NaOH needed was calculated as 80 µl of 20 mM NaOH needed per 75 µl of beads. Beads were washed manually in 1× B& W buffer. 2 multiwell wash plates were created with 200 µL 1×B&W per well. 1 multiwell bead plate was generated with 75 µL beads and add to 125 µL 1×B&W. Add combs to this plate. 1 multiwell library plate was created with 300 µL PCR reaction and 300 µL 2× B&W buffer. 1 standard plate was created with 80 µL NaOH in the appropriate wells. The remaining wells were filled with water. 1 PCR collection plate was generated with 20 µL 40 mM HCL and 5 µL 20×NVT. Combs were removed from the bead plate. Beads were mixed with the affinity reagent library in the library plate for library binding as follows by binding: 4× (medium mixing for 4 min 55 sec plus slow mixing for 5 sec) and collecting the beads 5× for 30 sec. Beads were washed two times (wash plate 1 and 2), by releasing the beads for 10 sec, washing the beads for 10 sec, and collecting the beads 5× for 30 sec. Peptides were denatured in NaOH by releasing them for 10 sec, mixing at medium speed for 10 min and slow mixing for 5 sec, then collecting the beads 5× for 30 sec. Combs were replaced in the bead plate.

All samples were quantified using an Oligreen assay. Oligreen standard was diluted to 2 ng/µL in 1×NVT. A 2-fold dilution of standard was performed in a black 96-well plate (the final volume was 100 µL). 2 µL of ssDNA was added to the plate. (the final volume was 100 µL). The 200× Oligreen reagent was diluted to 1×. 100 µL of 1× Oligreen reagent was added to each well on the plate. Readings were taken on a TecanF200 at 485 (20) nm/535 (25) nm before proceeding to the next round of selection.

Example 9: Streptavidin Agarose SELEX Protocol

Pre-Enrichment (3 Rounds)

Libraries were pre-enriched against the peptide target for three rounds prior to SELEX round 1. In pre-enrichment round (PE R)1 library were eluted with heat in water. Prior to PE R2 and R3 another 125 pmol naïve library was added to the heat elution.

Part 1: Preparation of Buffers for SELEX

Buffers were prepared for agarose bead-based SELEX. 1 L of 20× stock of NVT was prepared [200 mM HEPES, 2.4 M NaCl, 100 mM MgCl2, 100 mM KCl, 2% Tween20 pH 7.4] by dissolving 47.66 g HEPES (MW 238.30 g/mol), 140.256 g NaCl (MW 58.44 g/mol), 9.5211 g MgCl2 (MW 95.211 g/mol), and 7.455 g KCl (MW 74.55 g/mol) in 750 mL of water and adjusting the pH to 7.4 using HCl/NaOH. 20 mL of Tween20 was added and the final volume was brought to 1 L. Binding buffer was prepared by mixing 1×NVT with 300 µM dextran sulfate and 0.1 mg/ml sheared salmon sperm DNA. A wash buffer was prepared as 1× NVT.

Part 2: Preparation of Library for SELEX

Intermediate library stock was prepared in 1×NVT. The library was heated to 95° C. for 5 mins and then cooled for 10 mins.

Part 3: Pre-Enrichment Round

Initial Washing of Stock Streptavidin Agarose Beads

The number of streptavidin-agarose beads needed was calculated as 104 beads were used per sample at bead concentration of 10 mg/ml. The beads were resuspended in the vial by vortexing for >30 sec, or tilting and rotating for 5 min). Beads were removed from the stock vial and added to 1.5 mL microcentrifuge tube. 10 µL of beads was added to the wells of the 96-well filter plate. The 1.5 mL microcentrifuge tube was vortexed between additions to ensure agarose beads were suspended properly. 200 µL 1×NVT was added to each well. The plate was spun for 2 min at 1000×g. This was repeated 2× and the collection plate was emptied.

Peptide Immobilization

200 µL of 1 µM peptide was added to the wells. Plates were shaken for 1 hour. Plates were then centrifuged for 2 min at 1000×g and the collection plate was emptied. 200 µL of 1×NVT was added to each well. The plate was centrifuged for 2 min at 1000×g. The immobilization procedure was repeated 2 more times and the collection plate was emptied. 200 µL of 1 µM biotin-PEG4 was added to the wells. The plate was shaken for 10 minutes. The plate was spun for 2 min at 1000×g and the collection plate was emptied. 200 µL of 1×NVT was added to each well and the plate was spun for 2 min at 1000×g. The washing was repeated 2 more times, then the collection plate was emptied.

Positive Selection Against Beads 125 pmol of affinity reagent library was prepared in NVT binding buffer. 200 µL of library in NVT binding buffer was added into each well. The plate was shaken for 10 minutes. The plate was centrifuged for 2 min at 1000×g and the collection plate was emptied. Add 200 µL 1×NVT was added to each well. The plate was centrifuged for 2 min at 1000×g, then shaken for 10 minutes. The plate was centrifuged for 2 min at 1000×g and the collection plate was emptied. This procedure was repeated 2 more times. The collection plate was replaced with a clean collection plate. 50 µL of water at 95° C. was added to each well. The plate was shaken for 3 minutes at 70° C. The plate was centrifuged for 2 min at 1000×g SELEX 6 Rounds SELEX was carried out against long and short peptides using naïve and pre-enriched libraries. The elution for the first 2 rounds was split into two groups: EDTA and peptide competition elution. Round 3 onwards all samples were eluted with EDTA. All rounds included a second heat elution.

Part 1: Initial Washing of Beads for SELEX

The number of streptavidin-agarose beads needed was calculated as 10 µL beads were used per sample at bead concentration of 10 mg/ml. The beads were resuspended in the vial by vortexing for >30 sec, or tilting and rotating for 5 min). Beads were removed from the stock vial and added to 1.5 mL microcentrifuge tube. 10 µL of beads was added to the wells of the 96-well filter plate. The 1.5 mL microcentrifuge tube was vortexed between additions to ensure agarose beads were suspended properly. 200 µL 1×NVT was added to each well. The plate was spun for 2 min at 1000×g. This was repeated 2× and the collection plate was emptied.

Part 2: Peptide Immobilization

200 µL of 1 µM peptide was added to the wells. Plates were shaken for 1 hour. Plates were then centrifuged for 2 min at 1000×g and the collection plate was emptied. 200 µL of 1×NVT was added to each well. The plate was centrifuged for 2 min at 1000×g. The immobilization procedure was repeated 2 more times and the collection plate was emptied. 200 µL of 1 µM biotin-PEG4 was added to the wells. The plate was shaken for 10 minutes. The plate was spun for 2 min at 1000×g and the collection plate was emptied. 200 µL of 1×NVT was added to each well and the plate was spun for 2 min at 1000×g. The washing was repeated 2 more times, then the collection plate was emptied.

Part 3: Positive Selection Against Beads 125 pmol of affinity reagent library was prepared in NVT binding buffer. 200 µL of library in NVT binding buffer was added into each well. The plate was shaken for 1 hour. The plate was centrifuged for 2 min at 1000×g and the collection plate was emptied. 200 µL 1× NVT was added to each well. The plate was centrifuged for 2 min at 1000×g, then shaken for 10 minutes. The plate was centrifuged for 2 min at 1000×g and the collection plate was emptied. This procedure was repeated 2 more times. 50 μL 0.5 μM peptide was added to the peptide elution wells and the plate was shaken for 14 minutes. 50 μL 10 mM EDTA was added to the EDTA elution wells and the plate was shaken for 1 minute. The collection plate was replaced with a clean collection plate. 50 μL of water at 95° C. was added to each well. The plate was shaken for 3 minutes at 70° C. The plate was centrifuged for 2 min at 1000×g Part 4: Amplification of SELEX Output Contents were transferred from the Peptide/Salt Free plate to a qPCR plate. Two different mastermixes were prepared (one for EDTA elution & one for peptide elution). The mastermix for elution was prepared by combining Kapa HiFi Mastermix (1× final), F-primer/R-bio primer (1 uM final), SYBR Green (1× final), EDTA (4 mM final), 40 ul of SELEX elution, and water to the final volume. A TissueLyser was used 3 times to mix each sample. The plate was centrifuged at 2000×g for 1 min. Each sample was amplified for 10 cycles. 100 μL of the mastermix was added to each sample. The number of PCR cycles each sample requires to reach 1000000-1250000 FLU was recorded. Depending upon where the positive control sample peak plateaued, 12 samples including NTC were chosen to run on a bioanalyzer to check amplicon size as well as concentration to ensure enough material has been generated for the subsequent round of SELEX.

Part 5: Library Re-Generation

Contents were transferred from the Peptide/Salt Free plate to a qPCR plate. Two different mastermixes were prepared (one for EDTA elution & one for peptide elution). The mastermix for elution was prepared by combining Kapa HiFi Mastermix (1× final), F-primer/R-bio primer (1 uM final), SYBR Green (1× final), EDTA (4 mM final), 40 ul of SELEX elution, and water to the final volume. A TissueLyser was used 3 times to mix each sample. The plate was centrifuged at 2000×g for 1 min. Each sample was amplified for 10 cycles. 100 μL of the mastermix was added to each sample. The number of PCR cycles each sample requires to reach 1000000-1250000 FLU was recorded. Depending upon where the positive control sample peak plateaued, 12 samples including NTC were chosen to run on a bioanalyzer to check amplicon size as well as concentration to ensure enough material has been generated for the subsequent round of SELEX.

2× binding and wash buffer (B&W buffer) was prepared by combining 10 mM Tris-HCl, 1 mM EDTA, and 2 M NaCl, and adjusting the solution pH to 7.5. The amount of magnetic beads needed was calculated as 75 μl of beads needed for a 300 μl PCR reaction. The amount of NaOH needed was calculated as 80 μl of 20 mM NaOH needed per 75 μl of beads.

The magnetic beads (50 μL beads×number of 100 μL PCR reactions) were washed in 1 mL of 1× B&W buffer. The beads were pulled down using a magnetic tube rack and the buffer was removed. The beads were washed in the same volume of beads. The buffer was removed, and washing was repeated. An equal volume of 2× B&W buffer was added to the beads Samples were run on a MagMAX protocol. Combs sitting in 200 μl B&W were picked up from Combs at a 0 μl volume in the deep well plate. Combs were used to mix the beads and library for 20 min at RT. 100 μL of PCR reaction was combined with 100 μL of beads in 2× B&W buffer for a total volume of 200 μl in the deep well plate. Each well was medium mixed for 10 seconds, then medium mixed for 4 min 50 seconds, then slow mixed for 10 seconds. The procedures was repeated 2 times.

The Dynabeads with bound library were collected and transferred to Wash 1. Each well had a 200 μl volume in the deep well plate and was medium mixed for 10 seconds. Dynabeads with bound library were collected and transferred to Wash 2. Each well had a 200 μl volume in the deep well plate and was medium mixed for 10 seconds. Dynabeads with bound library were collected and transferred to the NaOH plate for elution in 20 mM NaOH. Each well had an 80 μl volume in the deep well plate and was medium mixed for 10 min. Dynabeads free of library were collected and transferred to Combs plate for release. NaOH elution contents were transferred to a PCR plate and 5 μl 20× NV buffer and 20 μl 40 mM HCl was added. pH was checked using pH paper (pH 7.2-7.4). A few samples were selected to check their size on SYBR Gold 2% EX gel. All samples were quantified using an Oligreen assay. Oligreen standard was diluted to 2 ng/μL in 1×NVT. A 2-fold dilution of standard was performed in a black 96-well plate (the final volume was 100 μL). 2 μL of ssDNA was added to the plate. (the final volume was 100 μL). The 200× Oligreen reagent was diluted to 1×. 100 μL of 1× Oligreen reagent was added to each well on the plate. Readings were taken on a TecanF200 at 485 (20) nm/535 (25) nm before proceeding to the next round of selection.

Example 10: Pool ELONA Assay

At least 15 μl at 100 μM of affinity reagent pools were created, as well as the individual biotinylated oligos. The affinity reagent pools were diluted to 50 μM using 2×NVT buffer (10 mM HEPES, 120 mM NaCl, 5 mM MgCl2, 5 mM KCl, pH 7.4 with 0.01% Tween20). The library was heated to 95° C. for 5 mins and then cooled for 10 mins.

ELONA Protocol

ELONA plates (Pierce™ Streptavidin Coated High Capacity Plates, Clear, 384-Well) were washed twice with 100 μl 1× NV buffer+0.1% Tween 20. Plates were incubated with 1 μM biotinylated peptide in 25 μL Peptide Binding Buffer (1× NV buffer with 0.1 mg/ml sssDNA (sheared salmon sperm DNA)) and shaken at ~500 RPM for 30 minutes. A total of 100 pmol of peptide was added per well of a streptavidin plate. For the wells that received biotin instead of peptide, 1.6 μM of biotin was added. Plates were washed 6 times with 100 μl 1× NV buffer+0.1% Tween 20. Each well was blocked with 100 μl SuperG Blocking Buffer+100 μM D-Biotin and shaken at ~500 RPM at room temperature for 30 min. During the block incubation, refolded aptamer was diluted and titrated. After blocking, plates were washed 6 times with 100 μl 1× NV buffer+0.1% Tween 20. The folded aptamers were added in 254 of Aptamer Binding Buffer (1× NV buffer with 0.1 mg/ml sssDNA and 300 μM dextran sulfate) with 100 uM D-Biotin to the wells, and shaken at ~500 RPM for 1 hour Detection Solution (0.5 ug/ml (1:1000 dilution of stock) streptavidin HRP conjugate in Aptamer Binding Buffer) was prepared 5 min before the end of the incubation period. The plate was washed 6 times with 100 μl 1× NV+0.1% Tween 20. 25 μl of Detection Solution was added to the sample wells and shaken at ~500 RPM for 30 min. The plate was washed 6 times with 100 μl of 1× NV+0.1% Tween 20. 25 μl of room temperature TMB substrate was added into each well and incubated for 1 min 30 sec. Development was stopped by adding 25 μl of 1 N HCl into each well. The color changed to yellow with maximum absorbance at 450 nm. Absorbance at 450 nm for each well was measured on a Tecan Spark.

Example 11: Free Solution SELEX Affinity Reagent Enrichment

Biotinylated peptide and aptamer library binding was carried out in solution for an hour as described in Example 8. Following binding, peptide along with the bound aptamers was immobilized on to streptavidin agarose beads. Following three 10 minutes washes, the bound aptamers were eluted in EDTA, PCR amplified and regenerated into single stranded libraries. This process was repeated for 6 rounds following with enrichment was assessed by next generation sequencing. Affinity reagent libraries were tested against a peptide library with peptides comprising the epitope LRDLRDLRDLRD (SEQ ID NO: 14) or TQATQATQATQA (SEQ ID NO: 15).

Figure 13A:
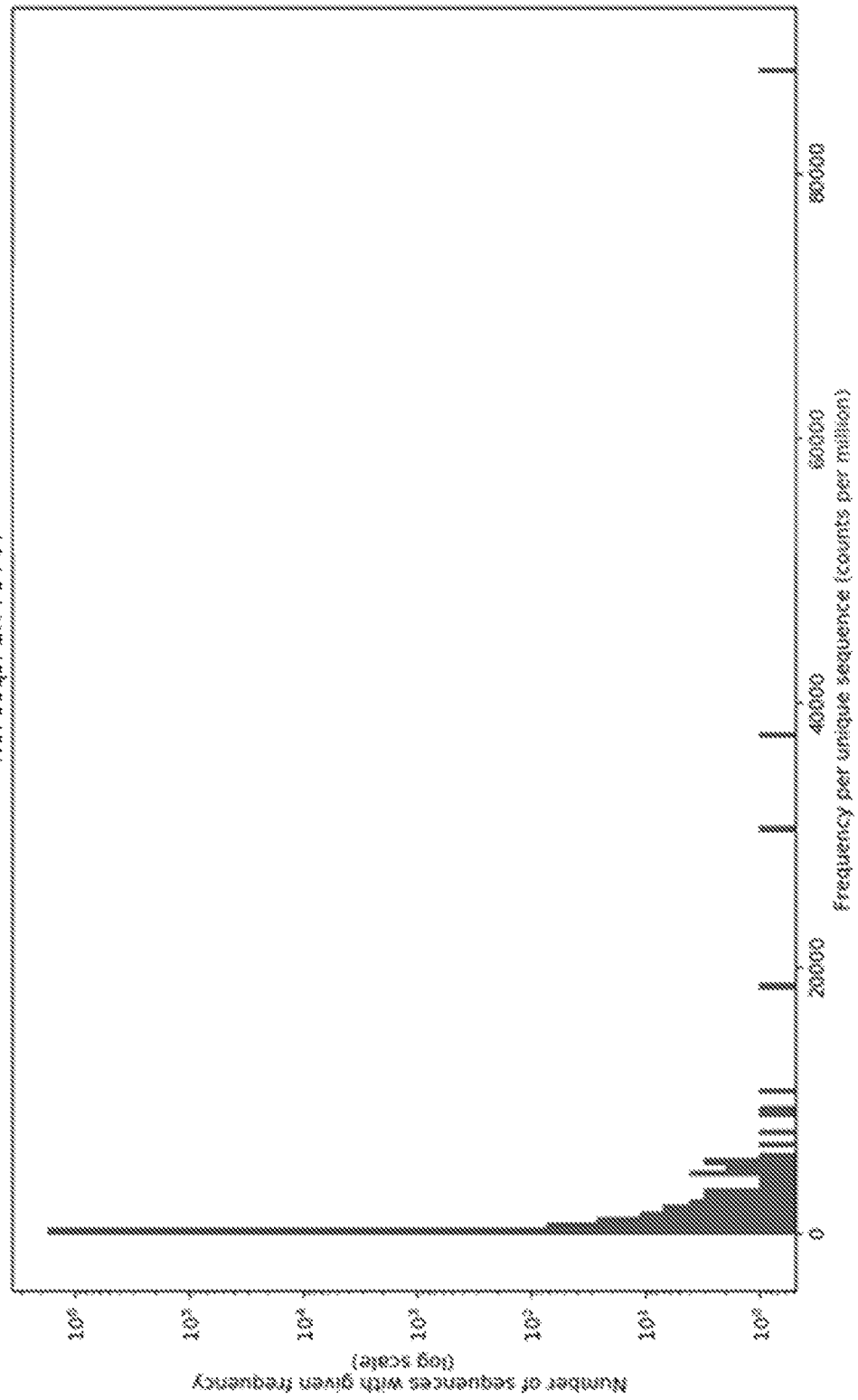
FIG. 13A shows free solution SELEX enrichment data for affinity reagents tested against peptides comprising repeats of the amino acid sequence LRD.
Figure 13B:
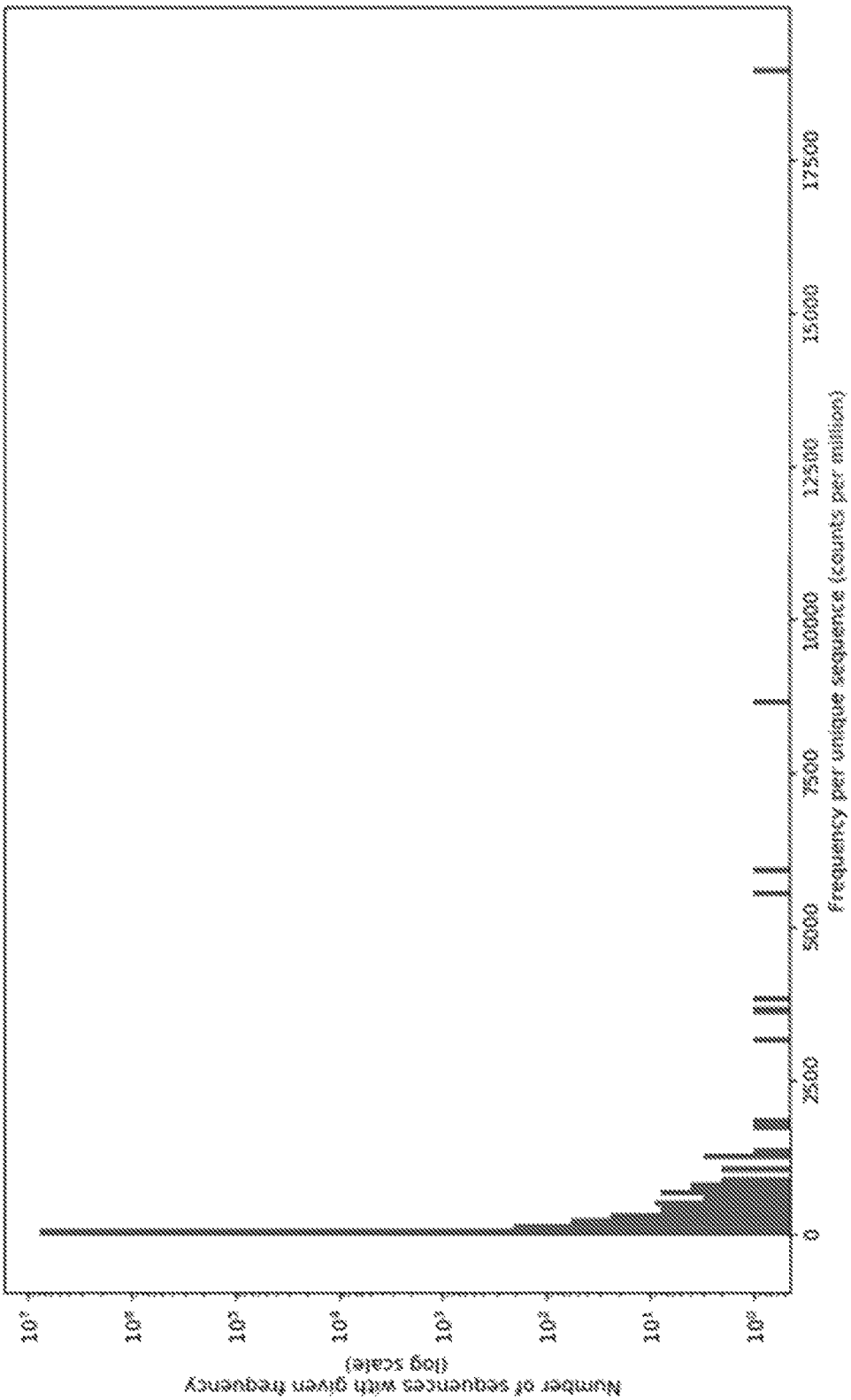
FIG. 13B shows free solution SELEX enrichment data for affinity reagents tested against peptides comprising repeats of the amino acid sequence TQA.

FIG. 13A shows affinity reagent enrichment data for affinity reagents tested against sequence LRDLRDLRDLRD (SEQ ID NO: 14). Detectable enrichment of sequences that bind the epitope is observed. FIG. 13B shows affinity reagent enrichment data for affinity reagents tested against sequence TQATQATQATQA (SEQ ID NO: 15). Detectable enrichment of sequences that bind the epitope is observed, although less enrichment is observed after 6 rounds of SELEX than that observed against epitope LRDLRDLRDLRD (SEQ ID NO: 14).

Example 12: SELEX Affinity Reagent Enrichment Using Magnetic Beads

Azide modified peptide were conjugated onto magnetic alkyne beads as described in Example 6. Following conjugation, peptide bound beads were incubated with aptamer library for one hour and post three 10 minutes washes, the bound aptamers were eluted in EDTA, PCR amplified and regenerated into single stranded libraries. This process was repeated for 6 rounds following with enrichment was assessed by next generation sequencing. Affinity reagent libraries were tested against a peptide library with peptides comprising the epitope YSLYSLYSLYSL (SEQ ID NO: 16) or EVT.

Figure 14A:
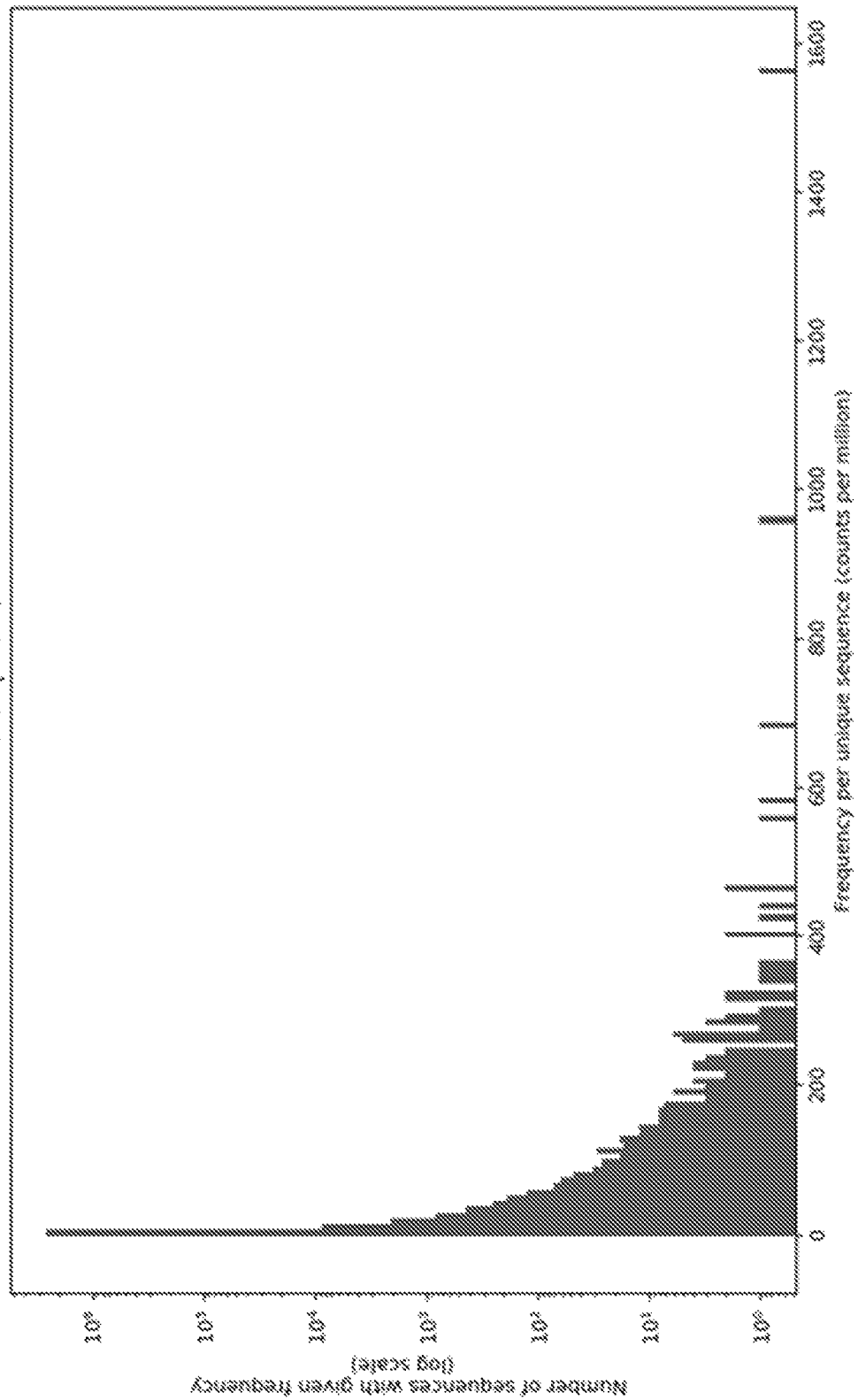
FIG. 14A shows magnetic bead SELEX enrichment data for affinity reagents tested against peptides comprising repeats of the amino acid sequence YSL.
Figure 14B:
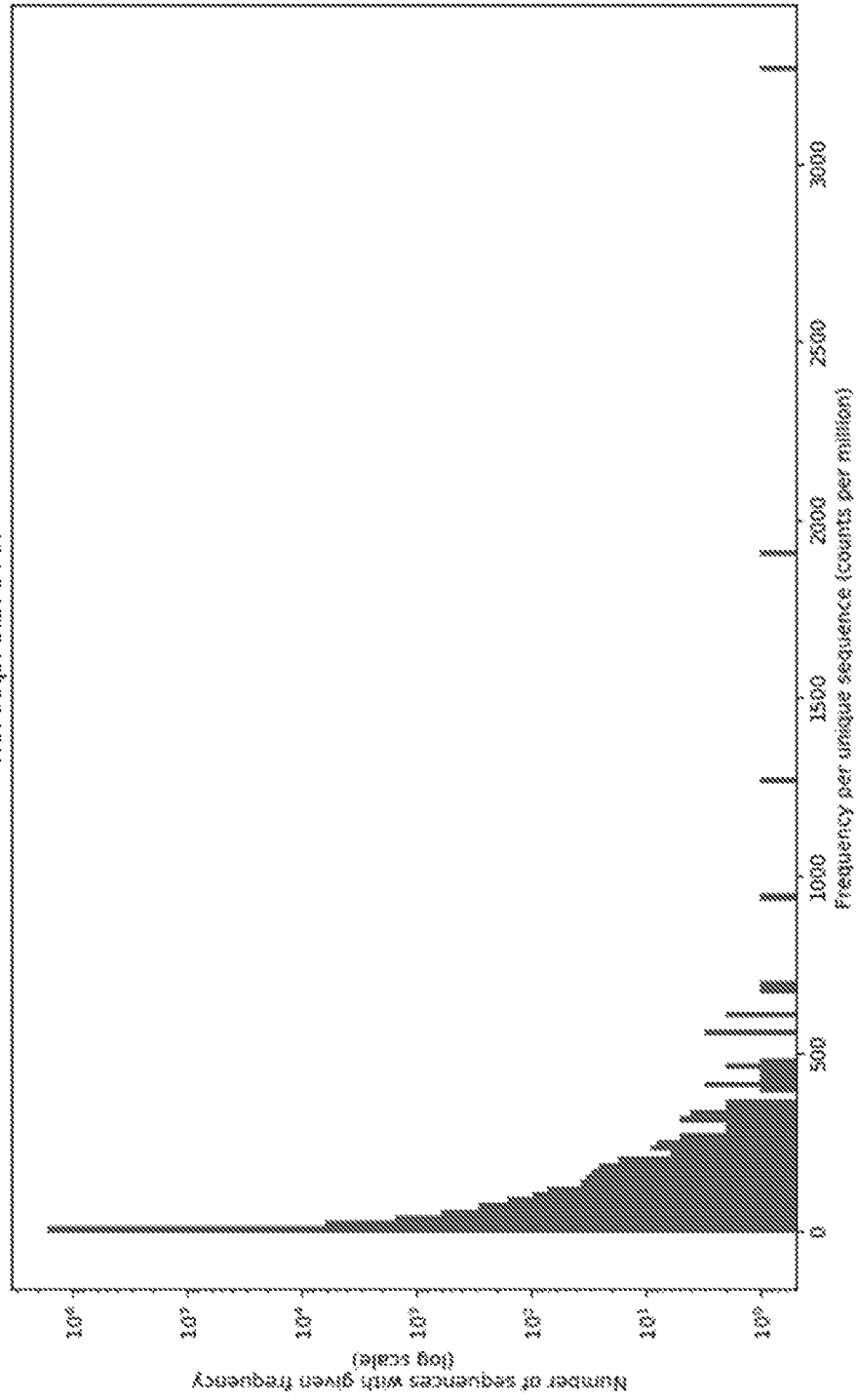
FIG. 14B shows magnetic bead SELEX enrichment data for affinity reagents tested against peptides comprising the amino acid sequence EVT.

FIG. 14A shows affinity reagent enrichment data for affinity reagents tested against sequence YSLYSLYSLYSL (SEQ ID NO: 16). Detectable enrichment of sequences that bind the epitope is observed. FIG. 14B shows affinity reagent enrichment data for affinity reagents tested against sequence EVT. Detectable enrichment of sequences that bind the epitope is observed, although less enrichment is observed after 6 rounds of SELEX than that observed against epitope YSLYSLYSLYSL (SEQ ID NO: 16).

Example 13: Probabilistic Affinity Binding Model

Figure 15A:
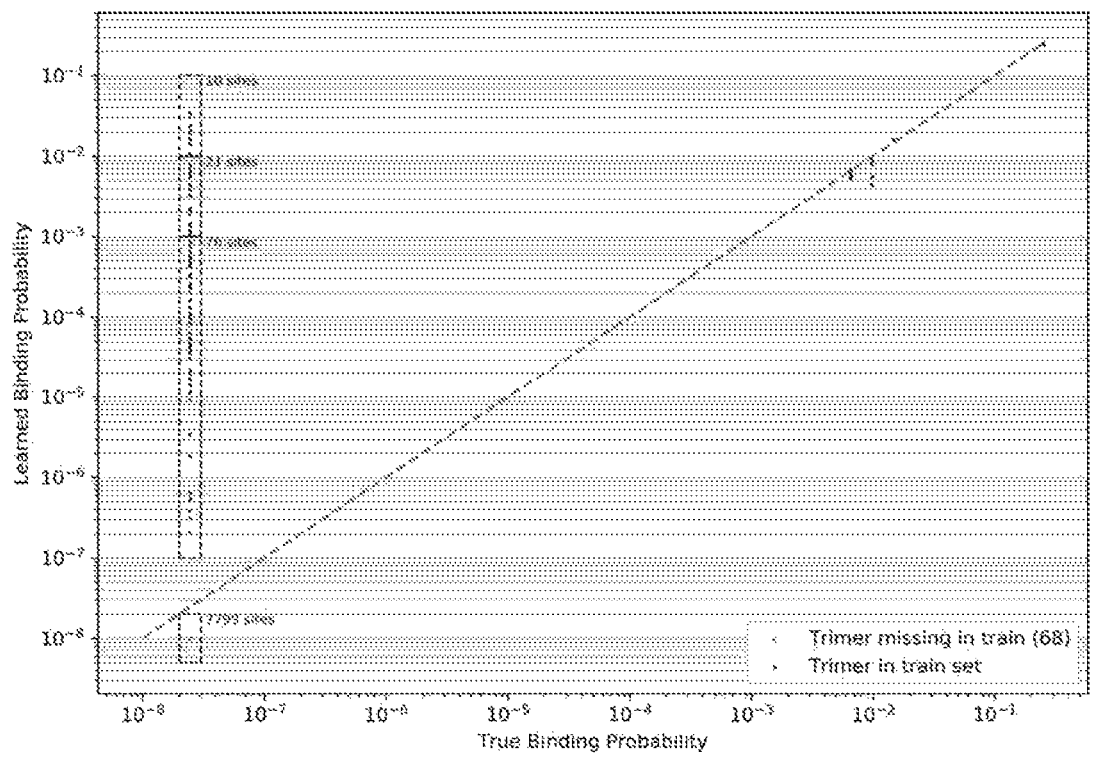
FIG. 15A shows a logarithmic plot of predicted trimer binding probabilities versus true binding probabilities for a first affinity reagent screened against 500 peptides.
Figure 15B:
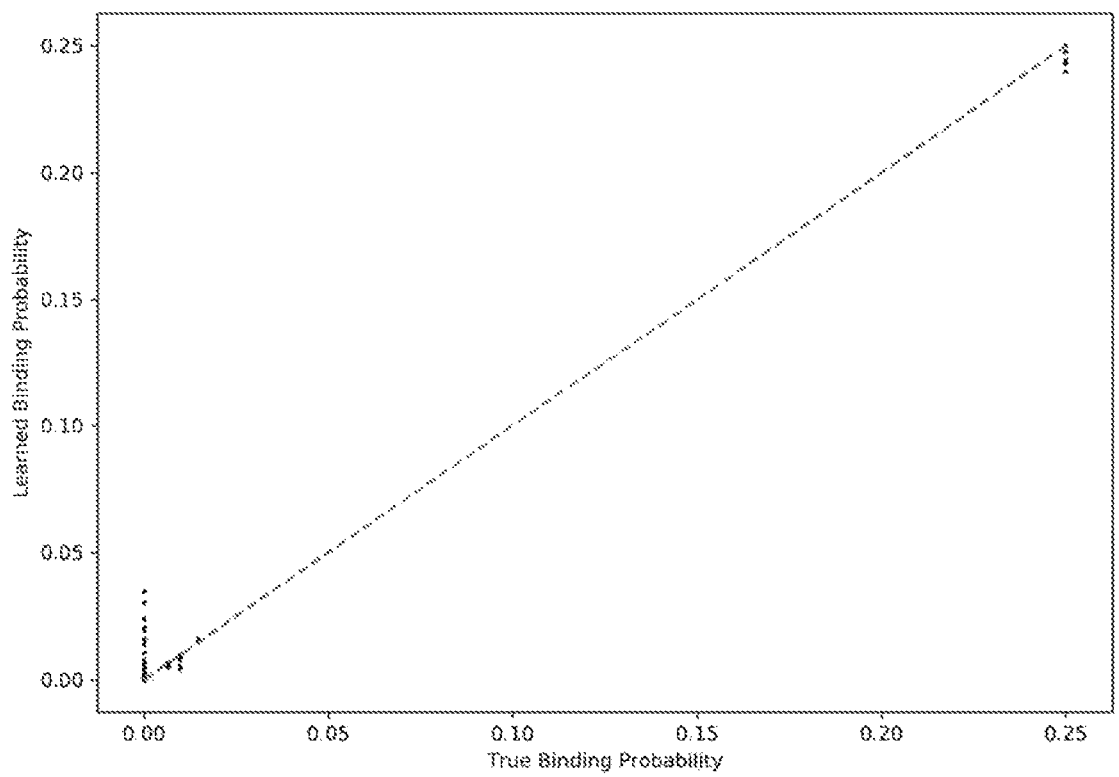
FIG. 15B shows a plot of the data from FIG. 15A on a non-logarithmic scale.
Figure 16A:
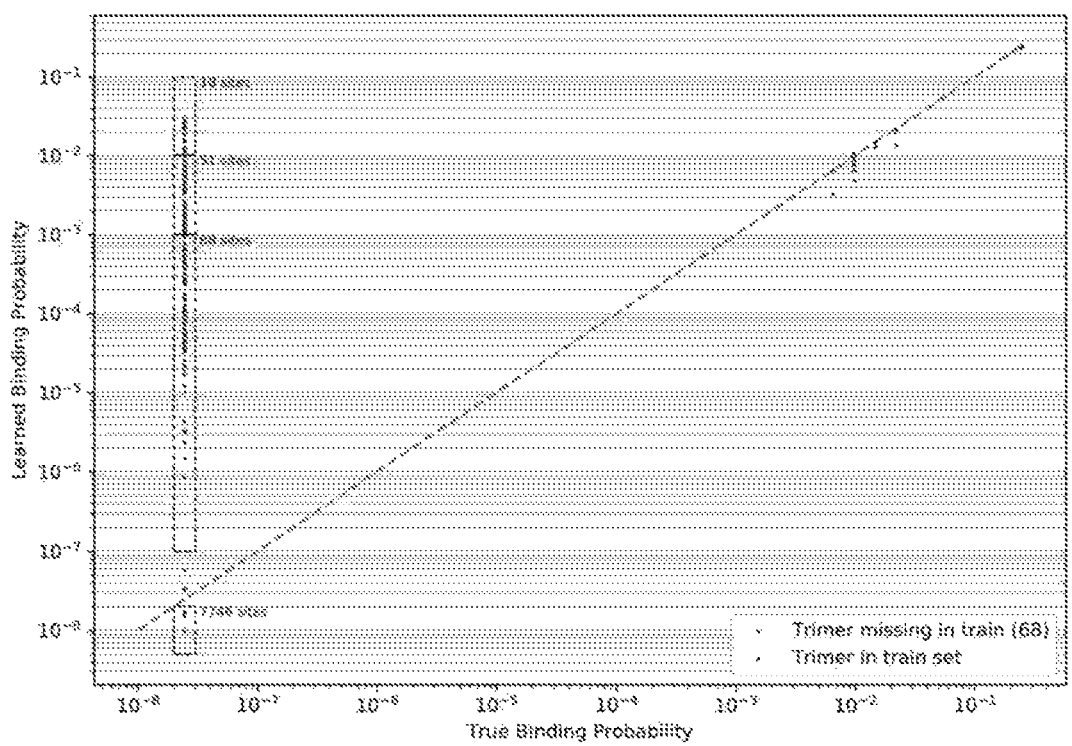
FIG. 16A shows a logarithmic plot of predicted trimer binding probabilities versus true binding probabilities for a second affinity reagent screened against 500 peptides.
Figure 16B:
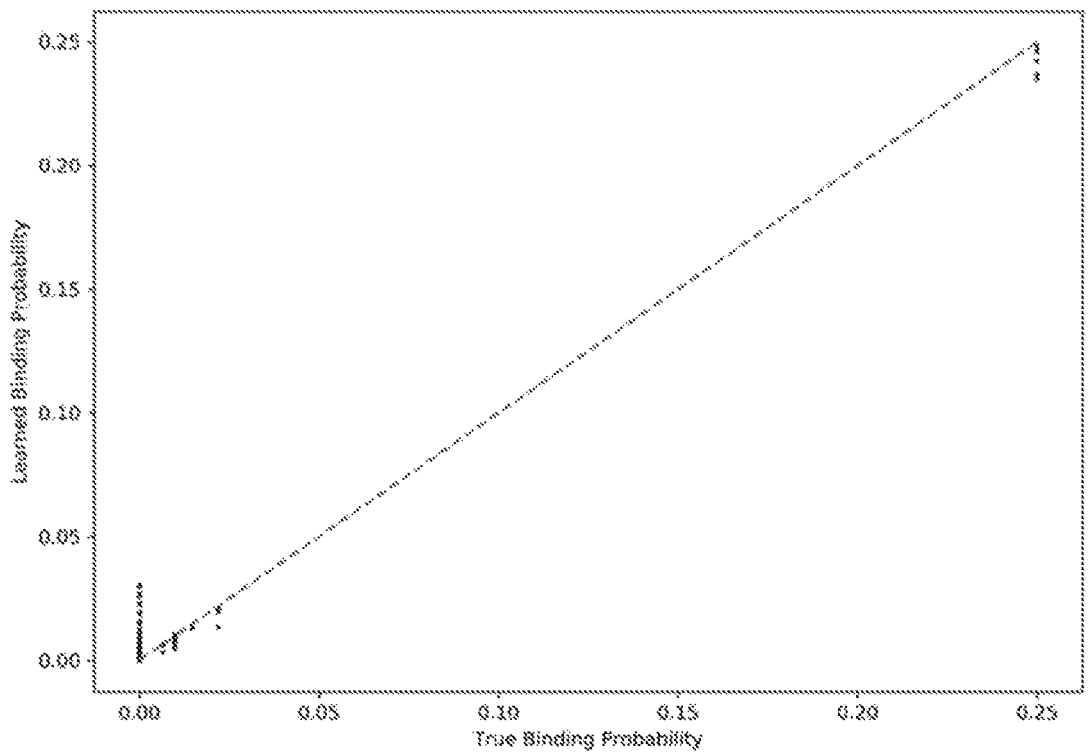
FIG. 16B shows a plot of the data from FIG. 16A on a non-logarithmic scale.
Figure 17A:
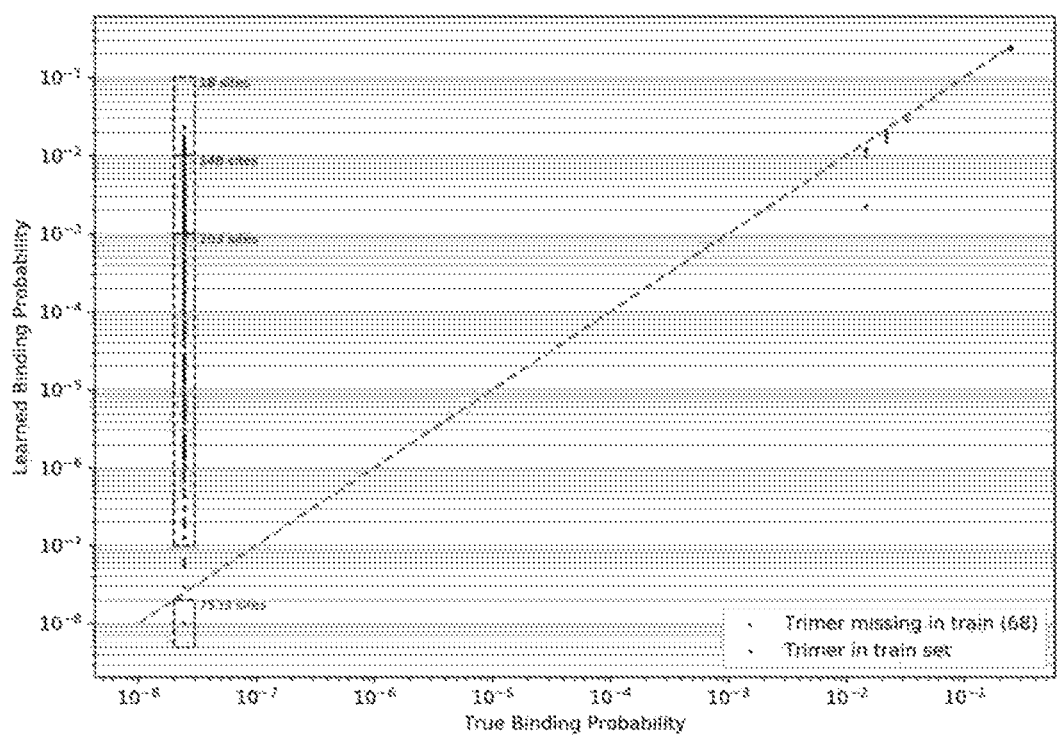
FIG. 17A shows a logarithmic plot of predicted trimer binding probabilities versus true binding probabilities for a third affinity reagent screened against 500 peptides.
Figure 17B:
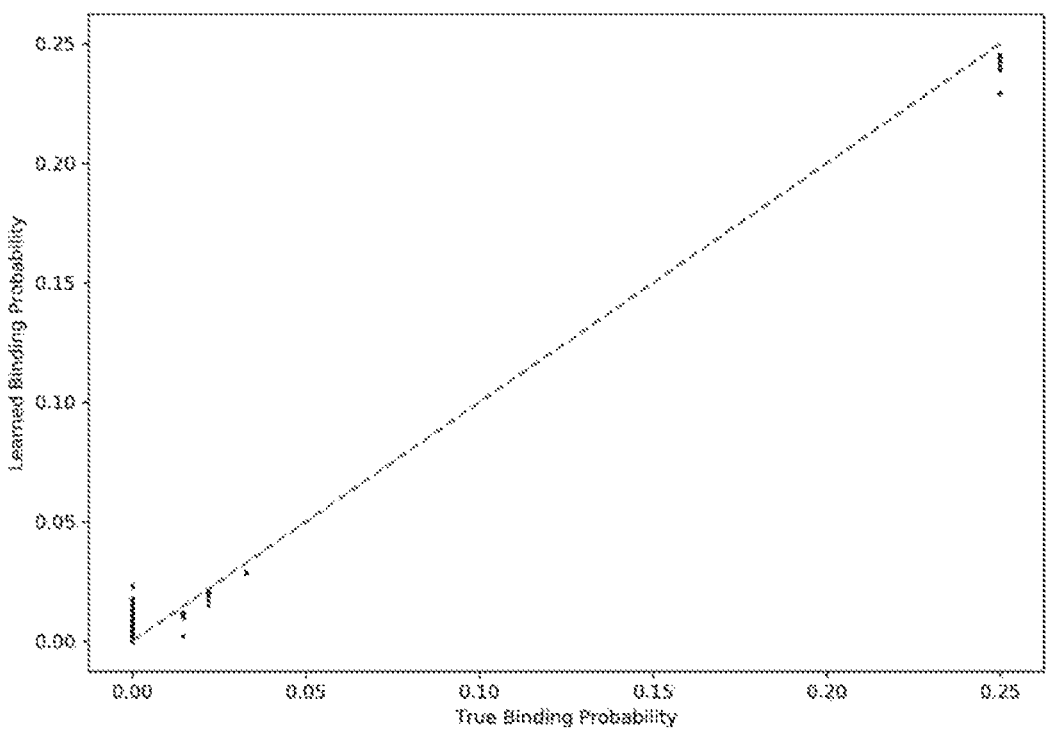
FIG. 17B shows a plot of the data from FIG. 17A on a non-logarithmic scale.

The probabilistic affinity binding model was used to learn the trimer binding probabilities of three affinity reagents from a binding dataset comprising binding of each affinity reagent to 500 unique, randomly-selected yeast proteins. Binding measurements (bind or no-bind) were accumulated for 10,000 copies of each of the 500 proteins for each affinity reagent. Each of the affinity reagents binds 5 trimers with probability 0.25 as well as other trimers with lower probability. For each of the three affinity reagents, the trimer binding probabilities predicted using this approach (y-axis) are plotted in comparison to the true binding probabilities of the affinity reagent (x-axis). A dashed line is plotted to indicate the line of perfect concordance between the predicted vs true probabilities. FIGS. 15A, 16A, and 17A show the log-transformed probabilities, with the count of trimers in four busy regions of the plot indicated for clarity. Further, the 68 trimers not present in the set of 500 proteins are plotted using a different shade although they may be obscured by other points in the plot. FIGS. 15B, 16B, and 17B show the same data without log-transformation of probabilities.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Notwithstanding the appended claims, the disclosure set forth herein is also defined by the following clauses:

1. A method of identifying an affinity reagent for an epitope, comprising:
   obtaining a first peptide library comprising a first plurality of peptides, each peptide comprising a sequence of a formula $\alpha X \beta$, wherein X is the desired epitope, and wherein $\alpha$ and $\beta$ are flanking domains comprising known amino acid sequences;
   exposing the first peptide library to a plurality of affinity reagents, thereby binding at least one affinity reagent of the plurality of affinity reagents to the first peptide library;
   determining the sequence or sequences of the at least one affinity reagents bound to the first plurality of peptides, thereby forming a reduced affinity reagent pool;
   obtaining a second peptide library comprising a second plurality of peptides, each peptide comprising a sequence of a formula $\gamma X \delta$, wherein X is the desired epitope, and wherein $\gamma$ and $\delta$ are flanking domains comprising a known amino acid sequence;
   exposing the second peptide library to the reduced affinity reagent pool, thereby binding at least one affinity reagent of the reduced affinity reagent pool to the second peptide library; and
   determining the sequence or sequences of at least one affinity reagent of the reduced affinity reagent pool bound to the second peptide library, thereby identifying an affinity reagent for the epitope X.

2. The method of clause 1, wherein $\alpha$ and $\beta$ comprise the same amino acid sequence.

3. The method of clause 2, wherein $\alpha$ and $\beta$ comprise a single amino acid.

4. The method of clause 3, wherein $\alpha$ and $\beta$ are the same single amino acid.

5. The method of clause 4, wherein $\alpha$ and $\beta$ are alanine or glycine.

6. The method of clause 1, wherein α and β comprise differing amino acid sequences.
7. The method of clause 1, wherein γ and δ comprise the same amino acid sequence.
8. The method of clause 7, wherein γ and δ comprise a single amino acid.
9. The method of clause 8, wherein γ and δ are the same single amino acid.
10. The method of clause 9, wherein γ and δ are arginine, aspartic acid, glutamine, proline or tryptophan.
11. The method of clause 1, wherein γ and δ comprise differing amino acid sequences.
12. The method of clause 1, wherein α or β comprises a differing amino acid sequence from γ and δ.
13. The method of clause 12, wherein α and β comprise differing amino acid sequences from γ and δ.
14. The method of clause 13, wherein α and β comprise the same first amino acid sequence and γ and δ comprise the same second amino acid sequence.
15. The method of clause 1, wherein X comprises an amino acid sequence of length m.
16. The method of clause 15, wherein m is in a range from 2 to 7 amino acids.
17. The method of clause 16, wherein m is 3 amino acids.
18. The method of clause 1, wherein X comprises an amino acid sequence that is proximal in the primary structure of the plurality of peptides.
19. The method of clause 1, wherein X comprises an amino acid sequence that is proximal in the secondary, tertiary, or quaternary structure of the plurality of peptides.
20. The method of clause 1, wherein at least 0.001% of the plurality of affinity reagents are bound to the first peptide library.
21. The method of clause 20, wherein at least 1% of the plurality of affinity reagents are bound to the first peptide library.
22. The method of clause 1, wherein no more than 0.001% of the reduced affinity reagent pool binds to the second peptide library.
23. The method of clause 1, wherein no more than 0.000001% of the reduced affinity reagent pool binds to the second peptide library.
24. The method of clause 1, wherein an affinity reagent of the plurality of affinity reagents comprise an oligonucleotide.
25. The method of clause 24, wherein the oligonucleotide comprises a barcode.
26. The method of clause 24, wherein the oligonucleotide comprises an adaptor for a sequencing reaction.
27. The method of clause 24, wherein the oligonucleotide comprises a detectable label or tag.
28. The method of clause 27, wherein the detectable label or tag comprises a fluorophore, bioluminescent label, radiolabel, or enzymatic tag.
29. The method of clause 1, wherein the determining the sequence or sequences of the affinity reagents bound to the first plurality of peptides comprises:
    separating the affinity reagents from the first peptide library; and
    after the separating, sequencing the affinity reagents, thereby determining the sequence or sequences of the affinity reagents.
30. The method of clause 1, wherein the determining the sequence or sequences of at least one affinity reagent of the reduced affinity reagent pool bound to the second peptide library comprises:
    separating the at least one affinity reagent from the second peptide library; and
    after the separating, sequencing the at least one affinity reagent, thereby determining the sequence or sequences of the at least one affinity reagent.
31. The method of clause 29 or 30, wherein the sequencing comprises performing a next-generation sequencing reaction.
32. The method of clause 29 or 30, wherein the separating comprises eluting the at least one affinity reagent from the peptide.
33. The method of clause 32, wherein the eluting the at least one affinity reagent comprises using an elution buffer.
34. The method of clause 32, where in the elution buffer comprises a chaotrope.
35. The method of clause 32, wherein the eluting the at least one affinity reagent comprises contacting the at least one affinity reagent with water, wherein the water is at a temperature of at least 50° C.
36. The method of clause 1, wherein α and β comprise amino acid sequences with a neutral electrical charge.
37. The method of clause 1, wherein α or β comprise amino acid sequences with a non-neutral electrical charge.
38. The method of clause 1, wherein α or β comprise amino acid sequences that do not sterically block at least a portion of epitope X.
39. The method of clause 1, wherein α and β comprise amino acid sequences that sterically block at least a portion of epitope X.
40. The method of clause 1, wherein α and β comprise amino acid sequences with homogeneous chemical diversity.
41. The method of clause 40, wherein the amino acid sequences with homogeneous chemical diversity comprise amino acid sequences comprising two or more amino acid side groups with equivalent electrical charge, hydrophobicity, hydrophilicity, steric size, polarity, molecular structure, or a combination thereof
42. The method of clause 1, wherein α and β comprise amino acid sequences with heterogeneous chemical diversity.
43. The method of clause 42, wherein the amino acid sequences with heterogeneous chemical diversity comprise amino acid sequences comprising two or more amino acid side groups with differing electrical charge, hydrophobicity, hydrophilicity, steric size, polarity, molecular structure, or a combination thereof
44. The method of clause 1, wherein γ and δ comprise amino acid sequences with a neutral electrical charge.
45. The method of clause 1, wherein γ and δ comprise amino acid sequences with a non-neutral electrical charge.
46. The method of clause 1, wherein γ and δ comprise amino acid sequences that do not sterically block at least a portion of epitope X.
47. The method of clause 1, wherein γ and δ comprise amino acid sequences that sterically block at least a portion of epitope X.
48. The method of clause 1, wherein γ and δ comprise amino acid sequences with homogeneous chemical diversity.
49. The method of clause 48, wherein the amino acid sequences with homogeneous chemical diversity comprise amino acid sequences comprising two or more amino acid side groups with equivalent electrical charge, hydrophobicity, hydrophilicity, steric size, polarity, molecular structure, or a combination thereof 50. The method of clause 1, wherein γ and δ comprise amino acid sequences with heterogeneous chemical diversity.

51. The method of clause 48, wherein the amino acid sequences with heterogeneous chemical diversity comprise amino acid sequences comprising two or more amino acid side groups with differing electrical charge, hydrophobicity, hydrophilicity, steric size, polarity, molecular structure, or a combination thereof 52. The method of clause 1, wherein the affinity reagent pool further comprises a liquid medium.

53. The method of clause 52, wherein the liquid medium is an aqueous solution.

54. The method of clause 53, wherein the aqueous solution is a buffered solution.

55. The method of clause 1, further comprising washing the at least one affinity reagent of the plurality of affinity reagents bound to the first peptide library.

56. The method of clause 1, further comprising washing the at least one affinity reagent of the reduced affinity reagent pool bound to the second peptide library.

57. The method of clause 55 or 56, wherein the washing comprises using a wash buffer.

58. The method of clause 57, wherein the wash buffer comprises a detergent, surfactant, or chaotrope.

59. The method of clause 1, wherein the peptides within the first or second peptide library are in a native state.

60. The method of clause 1, wherein the peptides within the peptide first or second library are in a non-native state.

61. The method of clause 1, wherein the non-native state is a denatured state or a partially-folded state.

62. The method of clause 60 or 61, further comprising repeating all steps with the plurality of peptides in a native state.

63. The method of clause 62, wherein the at least affinity reagent for epitope X in the native state differs from the at least one affinity reagent for epitope X in the non-native state.

64. The method of clause 62, wherein the at least affinity reagent for epitope X in the native state is the same as the at least one affinity reagent for epitope X in the non-native state.

65. The method of clause 1, wherein the epitope X binds with more than one affinity reagent.

66. The method of clause 1, wherein the at least one affinity reagent binds with more than one epitope.

67. The method of clause 66, wherein the more than one epitope comprise degenerate amino acid sequences.

68. The method of clause 67, wherein the degenerate amino acid sequences differ by one amino acid.

69. The method of clause 67, wherein the degenerate amino acid sequences differ by more than one amino acid.

70. The method of clause 67, 68, or 69, wherein the differing amino acids comprise similar chemical properties, wherein the chemical properties are selected from the group consisting of electrical charge, hydrophobicity, hydrophilicity, steric size, polarity, molecular structure, or a combination thereof 71. The method of clause 67, 68, or 69, wherein the differing amino acids comprise dissimilar chemical properties, wherein the chemical properties are selected from the group consisting of electrical charge, hydrophobicity, hydrophilicity, steric size, polarity, molecular structure, or a combination thereof 72. The method of clause 1, wherein the plurality of peptides of the first peptide library or the plurality of peptides of the second peptide library are bound to a substrate.

73. The method of clause 1, wherein the plurality of peptides of the first peptide library or the plurality of peptides of the second peptide library are not bound to a substrate.

74. The method of clause 72, wherein the substrate comprises a flow cell.

75. The method of clause 1, comprising repeating one or more times the steps of exposing the first peptide library to the plurality of affinity reagents and determining the sequence or sequences of the at least one affinity reagents.

76. The method of clause 1, comprising repeating one or more times the steps of exposing the second peptide library to the reduced affinity reagent pool and determining the sequence or sequences of the at least one affinity reagents.

77. The method of clause 1, wherein an affinity reagent of the plurality of affinity reagents comprises an oligonucleotide, peptimer, mini protein binder, antibody, antibody fragment, or a combination thereof 78. A method of identifying an affinity reagent for an epitope, comprising:
    obtaining a peptide library comprising a plurality of peptides, wherein a peptide of the plurality of peptides comprises more than one epitope X in its sequence;
    exposing the peptide library to an affinity reagent pool comprising a plurality of affinity reagents, thereby binding at least one affinity reagent to the peptide comprising more than one epitope X in its sequence; and
    determining the sequence or sequences of the at least one affinity reagent bound to the peptide comprising more than one epitope X in its sequence, thereby identifying an affinity reagent for epitope X.

79. The method of clause 78, wherein the more than one epitope X are contiguous.

80. The method of clause 78, wherein the more than one epitope X are non-contiguous.

81. The method of clause 80, wherein the more than one epitope X comprise an intervening amino acid sequence.

82. The method of clause 81, wherein the peptide of the plurality of peptides comprises at least three instances of epitope X that are separated by an amino acid sequence comprising the same intervening sequence.

83. The method of clause 81, wherein the peptide of the plurality of peptides comprises at least three instances of epitope X that are separated by amino acid sequences comprising different intervening sequences.

84. The method of clause 78, wherein the peptide of the plurality of peptides further comprises an epitope Y.

85. The method of clause 84, wherein the epitope Y is contiguous to epitope X.

86. The method of clause 85, wherein the epitope Y is contiguous to each epitope X.

87. The method of clause 84, wherein the epitope Y is non-contiguous to each epitope X.

88. The method of clause 87, wherein each epitope Y is regularly spaced in the amino acid sequence of the peptide relative to epitope X.

89. The method of clause 87, wherein at least two of epitope Y are randomly spaced in the amino acid sequence of the peptide relative to epitope X.
90. The method of clause 78, wherein X comprises an amino acid sequence of length m.
91. The method of clause 90, wherein m is in a range from 2 to 7 amino acids.
92. The method of clause 91, wherein m is 3 amino acids.
93. The method of clause 79, wherein the more than one contiguous epitope X further comprises flanking domains $\alpha$ and $\beta$.
94. The method of clause 93, wherein $\alpha$ and $\beta$ comprise the same amino acid sequence.
95. The method of clause 94, wherein $\alpha$ and $\beta$ comprise a single amino acid.
96. The method of clause 95, wherein $\alpha$ and $\beta$ are the same single amino acid.
97. The method of clause 96, wherein $\alpha$ and $\beta$ are alanine or glycine.
98. The method of clause 93, wherein $\alpha$ and $\beta$ comprise differing amino acid sequences.
99. The method of clause 78, wherein an affinity reagent of the plurality of affinity reagents comprises an oligonucleotide.
100. The method of clause 99, wherein the oligonucleotide comprises a barcode.
101. The method of clause 99, wherein the oligonucleotide comprises an adaptor for a sequencing reaction.
102. The method of clause 99, wherein the oligonucleotide comprises a detectable label or tag.
103. The method of clause 102, wherein the detectable label or tag comprises a fluorophore, bioluminescent label, radiolabel, or enzymatic tag.
104. The method of clause 78, wherein the determining the sequence or sequences of the at least one affinity reagent bound to the peptide library comprises:
    separating at least one affinity reagent from the peptide library; and
    sequencing the at least one affinity reagent, thereby determining the sequence or sequences of the at least one affinity reagent.
105. The method of clause 104, wherein the sequencing comprises performing a next-generation sequencing reaction.
106. The method of clause 104, wherein the separating comprises eluting the at least one affinity reagent from the peptide.
107. The method of clause 106, wherein the eluting the at least one affinity reagent comprises using an elution buffer.
108. The method of clause 106, where in the elution buffer comprises a chaotrope.
109. The method of clause 106, wherein the eluting the at least one affinity reagent comprises contacting the at least one affinity reagent with water, wherein the water is at a temperature of at least 50° C.
110. The method of clause 93, wherein $\alpha$ and $\beta$ comprise amino acid sequences with homogeneous chemical diversity.
111. The method of clause 110, wherein the amino acid sequences with homogeneous chemical diversity comprise amino acid sequences comprising two or more amino acid side groups with equivalent electrical charge, hydrophobicity, hydrophilicity, steric size, polarity, molecular structure, or a combination thereof
112. The method of clause 93, wherein $\alpha$ and $\beta$ comprise amino acid sequences with heterogeneous chemical diversity.
113. The method of clause 112, wherein the amino acid sequences with heterogeneous chemical diversity comprise amino acid sequences comprising two or more amino acid side groups with differing electrical charge, hydrophobicity, hydrophilicity, steric size, polarity, molecular structure, or a combination thereof
114. The method of clause 78, wherein the affinity reagent pool further comprises a liquid medium.
115. The method of clause 114, wherein the liquid medium is an aqueous solution.
116. The method of clause 115, wherein the aqueous solution is a buffered solution.
117. The method of clause 78, further comprising washing the at least one affinity reagent of the plurality of affinity reagents bound to the first peptide library.
118. The method of clause 78, further comprising washing the at least one affinity reagent of the affinity reagent pool bound to the peptide.
119. The method of clause 117 or 118, wherein the washing comprises using a wash buffer.
120. The method of clause 119, wherein the wash buffer comprises a detergent, surfactant, or chaotrope.
121. The method of clause 78, wherein the peptides within the peptide library are in a native state.
122. The method of clause 78, wherein the peptides within the peptide library are in a non-native state.
123. The method of clause 78, wherein the non-native state is a denatured state or a partially-folded state.
124. The method of clause 122 or 123, further comprising repeating all steps with the plurality of peptides in a native state.
125. The method of clause 124, wherein the at least affinity reagent for epitope X in the native state differs from the at least one affinity reagent for epitope X in the non-native state.
126. The method of clause 124, wherein the at least affinity reagent for epitope X in the native state is the same as the at least one affinity reagent for epitope X in the non-native state.
127. The method of clause 78, wherein the epitope X binds with more than one affinity reagent.
128. The method of clause 78, wherein the at least one affinity reagent binds with more than one epitope.
129. The method of clause 128, wherein the more than one epitope comprise degenerate amino acid sequences.
130. The method of clause 129, wherein the degenerate amino acid sequences differ by one amino acid.
131. The method of clause 129, wherein the degenerate amino acid sequences differ by more than one amino acid.
132. The method of clause 129, 130, or 131, wherein the differing amino acids comprise similar chemical properties, wherein the chemical properties are selected from the group consisting of electrical charge, hydrophobicity, hydrophilicity, steric size, polarity, molecular structure, or a combination thereof
133. The method of clause 129, 130, or 131, wherein the differing amino acids comprise dissimilar chemical properties, wherein the chemical properties are selected from the group consisting of electrical charge, hydrophobicity, hydrophilicity, steric size, polarity, molecular structure, or a combination thereof 134. The method of clause 78, wherein the plurality of peptides of the peptide library are bound to a substrate.
135. The method of clause 78, wherein the plurality of peptides of the peptide library are not bound to a substrate.
136. The method of clause 134, wherein the substrate comprises a flow cell.
137. A method of identifying an affinity reagent for an epitope, comprising:
contacting a plurality of peptides within a peptide library in a first medium with a plurality of affinity reagents within an affinity reagent pool in a second medium to form peptide-affinity reagent complexes, wherein each peptide-affinity reagent complex comprises a peptide and at least one bound affinity reagent, and wherein each peptide comprises an epitope X;
collecting the peptide-affinity reagent complexes;
separating unbound affinity reagents; and
determining the sequence or sequences of the affinity reagents of the peptide-affinity reagent complexes, thereby identifying at least one affinity reagent for epitope X.
138. The method of clause 137, wherein the first medium or the second medium comprises an aqueous solution.
139. The method of clause 138, wherein the aqueous solution comprises a buffered solution.
140. The method of clause 138, wherein the first medium and the second medium comprises a buffered aqueous solution.
141. The method of clause 137, wherein the peptides within the peptide library are in a native state.
142. The method of clause 137, wherein the peptides within the peptide library are in a non-native state.
143. The method of clause 137, wherein the non-native state is a denatured state or a partially-folded state.
144. The method of clause 142 or 143, further comprising repeating all steps with the plurality of peptides in a native state.
145. The method of clause 144, wherein the at least one affinity reagent for epitope X in the native state differs from the at least one affinity reagent for epitope X in the non-native state.
146. The method of clause 145, wherein the at least one affinity reagent for epitope X in the native state is the same as the at least one affinity reagent for epitope X in the non-native state.
147. The method of clause 137, wherein the epitope X binds with more than one affinity reagent.
148. The method of clause 137, wherein the at least one affinity reagent binds with more than one epitope.
149. The method of clause 148, wherein the more than one epitope comprise degenerate amino acid sequences.
150. The method of clause 149, wherein the degenerate amino acid sequences differ by one amino acid.
151. The method of clause 149, wherein the degenerate amino acid sequences differ by more than one amino acid.
152. The method of clause 149, 150, or 151, wherein the differing amino acids comprise similar chemical properties, wherein the chemical properties are selected from the group consisting of electrical charge, hydrophobicity, hydrophilicity, steric size, polarity, molecular structure, or a combination thereof
153. The method of clause 149, 150, or 151, wherein the differing amino acids comprise dissimilar chemical properties, wherein the chemical properties are selected from the group consisting of electrical charge, hydrophobicity, hydrophilicity, steric size, polarity, molecular structure, or a combination thereof
154. The method of clause 137, wherein the collecting the peptide-affinity reagent complexes comprises binding the peptide-affinity reagent complexes to a substrate.
155. The method of clause 137, wherein the collecting the peptide affinity reagent complexes comprises separating the peptide affinity reagent complexes from the first or second medium.
156. The method of clause 137, wherein X comprises an amino acid sequence of length m.
157. The method of clause 156, wherein m is in a range from 2 to 7 amino acids.
158. The method of clause 157, wherein m is 3 amino acids.
159. The method of clause 137, wherein X comprises an amino acid sequence that is proximal in the primary structure of the plurality of peptides.
160. The method of clause 137, wherein X comprises an amino acid sequence that is proximal in the secondary, tertiary, or quaternary structure of the plurality of peptides.
161. The method of clause 137, wherein an affinity reagent of the plurality of affinity reagents comprise an oligonucleotide.
162. The method of clause 161, wherein the oligonucleotide comprises a barcode.
163. The method of clause 161, wherein the oligonucleotide comprises an adaptor for a sequencing reaction.
164. The method of clause 161, wherein the oligonucleotide comprises a detectable label or tag.
165. The method of clause 161, wherein the detectable label or tag comprises a fluorophore, bioluminescent label, radiolabel, or enzymatic tag.
166. The method of clause 137, wherein the determining the sequence or sequences of the at least one affinity reagent bound to the plurality of peptides comprises:
separating the at least one affinity reagent from the plurality of peptides; and
sequencing the at least one affinity reagent, thereby determining the sequence or sequences of the at least one affinity reagent.
167. The method of clause 166, wherein the sequencing comprises performing a next-generation sequencing reaction.
168. The method of clause 166, wherein the separating comprises eluting the at least one affinity reagent from the peptide.
169. The method of clause 168, wherein the eluting the at least one affinity reagent comprises using an elution buffer.
170. The method of clause 169, where in the elution buffer comprises a chaotrope.
171. The method of clause 168, wherein the eluting the at least one affinity reagent comprises contacting the at least one affinity reagent with water, wherein the water is at a temperature of at least 50° C.
172. The method of clause 137, further comprising washing the at least one affinity reagent of the plurality of affinity reagents bound to the plurality of peptides.
173. The method of clause 172, wherein the washing comprises using a wash buffer.
174. The method of clause 173, wherein the wash buffer comprises a detergent, surfactant, or chaotrope.

175. An affinity reagent comprising a structure of $S_1S_2S_3$, wherein $S_1$ and $S_3$ are adaptor domains capable of binding a complementary adaptor, and wherein $S_2$ is an epitope binding domain, wherein the epitope binding domain binds to the one or more peptide epitopes with a equilibrium binding constant $K_d$ of less than $10^{-6}$ M.
176. The affinity reagent of clause 175, wherein the affinity reagent comprises an oligonucleotide.
177. The affinity reagent of clause 175, wherein the adaptor domains are next generation sequencing adaptors.
178. The affinity reagent of clause 175, wherein $S_1$ or $S_3$ comprises a barcode.
179. The affinity reagent of clause 175, wherein $S_1$ or $S_3$ comprises a streptavidin tag.
180. The method of clause 176, wherein the oligonucleotide comprises a detectable label or tag.
181. The affinity reagent of clause 180, wherein the detectable label or tag comprises a fluorophore, bioluminescent label, radiolabel, or enzymatic tag.
182. The affinity reagent of clause 176, wherein $S_2$ comprises no more than about 90 nucleotides.
183. The affinity reagent of clause 182, wherein $S_2$ comprises no more than about 80 nucleotides.
184. The affinity reagent of clause 183, wherein $S_2$ comprises no more than about 70 nucleotides.
185. The affinity reagent of clause 184, wherein $S_2$ comprises no more than about 60 nucleotides.
186. The affinity reagent of clause 185, wherein $S_2$ comprises no more than about 50 nucleotides.
187. The affinity reagent of clause 186, wherein $S_2$ comprises no more than about 40 nucleotides.
188. The affinity reagent of clause 187, wherein $S_2$ comprises no more than about 30 nucleotides.
189. The affinity reagent of clause 175, wherein the affinity reagent binds to more than one epitope with a equilibrium binding constant $K_d$ of less than $10^{-6}$ M.
190. The affinity reagent of clause 189, wherein the more than one epitope comprise degenerate amino acid sequences.
191. The affinity reagent of clause 190, wherein the degenerate amino acid sequences differ by one amino acid.
192. The affinity reagent of clause 190, wherein the degenerate amino acid sequences differ by more than one amino acid.
193. The affinity reagent of clause 190, 191 or 192, wherein the differing amino acids comprise similar chemical properties, wherein the chemical properties are selected from the group consisting of electrical charge, hydrophobicity, hydrophilicity, steric size, polarity, molecular structure, or a combination thereof
194. The affinity reagent of clause 190, 191, or 192, wherein the differing amino acids comprise dissimilar chemical properties, wherein the chemical properties are selected from the group consisting of electrical charge, hydrophobicity, hydrophilicity, steric size, polarity, molecular structure, or a combination thereof
195. The affinity reagent of clause 189, wherein the affinity reagent binds to one or more epitopes with an equilibrium binding constant $K_d$ of less than $10^{-7}$ M.
196. The affinity reagent of clause 195, wherein the affinity reagent binds to one or more epitopes with an equilibrium binding constant $K_d$ of less than $10^{-8}$ M.
197. The affinity reagent of clause 196, wherein the affinity reagent binds to one or more epitopes with an equilibrium binding constant $K_d$ of less than $10^{-9}$ M.
198. The affinity reagent of clause 197, wherein the affinity reagent binds to one or more epitopes with an equilibrium binding constant $K_d$ of less than $10^{-10}$ M.
199. The affinity reagent of clause 198, wherein the affinity reagent binds to one or more epitopes with an equilibrium binding constant $K_d$ of less than $10^{-11}$ M.
200. The affinity reagent of clause 199, wherein the affinity reagent binds to one or more epitopes with an equilibrium binding constant $K_d$ of less than $10^{-12}$ M.
201. The affinity reagent of clause 175, wherein the affinity reagent binds to one or more epitopes for a time period of at least 1 minute.
202. The affinity reagent of clause 175, wherein the affinity reagent binds to one or more epitopes for a time period of at least 15 minutes.
203. The affinity reagent of clause 202, wherein the affinity reagent binds to one or more epitopes for a time period of at least 1 hour.
204. The affinity reagent of clause 175, wherein the affinity reagent binds to one or more peptide epitopes when the peptide is in a native state.
205. The affinity reagent of clause 175, wherein the affinity reagent binds to one or more peptide epitopes when the peptide is in a non-native state.
206. The affinity reagent of clause 205, wherein the non-native state comprises a denatured state or a partially-folded state.
207. The affinity reagent of clause 175, wherein the affinity reagent further comprises a liquid medium.
208. The affinity reagent of clause 207, wherein the liquid medium comprises an aqueous medium.
209. An affinity reagent pool, comprising:
    A plurality of affinity reagents;
    wherein two or more affinity reagents of the plurality of affinity comprise a structure $S_1S_2S_3$, wherein $S_1$ and $S_3$ comprise common adaptor domains and $S_2$ comprises an epitope binding domain; and
    wherein a first affinity reagent of the two or more affinity reagents comprises a first domain $S_2$ with a characterized specificity for peptide epitope $X_1$, and wherein a second affinity reagent of the two or more affinity reagents comprises a second domain $S_2$ with a characterized specificity for a peptide epitope $X_2$, wherein the first domain $S_2$ differs from the second domain $S_2$.
210. The affinity reagent pool of clause 209, wherein $X_1$ comprises a different amino acid sequence than $X_2$.
211. The affinity reagent pool of clause 209, wherein $X_1$ comprises the same amino acid sequences as $X_2$.
212. The affinity reagent pool of clause 209, further comprising a third affinity reagent comprising a third domain $S_2$ with a characterized specificity for peptide epitope $X_3$, wherein the third domain $S_2$ differs from the first domain $S_2$ and the second domain $S_2$.
213. The affinity reagent pool of clause 212, wherein $X_3$ comprises a different amino acid sequence than $X_1$ or $X_2$.
214. The affinity reagent pool of clause 213, wherein $X_3$ comprises a different amino acid sequence than $X_1$ and $X_2$.
215. The affinity reagent pool of clause 214, wherein $X_3$ comprises the same amino acid sequence as $X_1$ and $X_2$.
216. The affinity reagent pool of clause 2015, wherein $X_3$ comprises the same amino acid sequence as $X_1$ and $X_2$.
217. The affinity reagent pool of clause 209, wherein the two or more affinity reagents comprise oligonucleotides.

218. The affinity reagent pool of clause 209, wherein the common adaptor domains are next generation sequencing adaptors.
219. The affinity reagent pool of clause 209, wherein $S_1$ or $S_3$ comprises a barcode.
220. The affinity reagent pool of clause 209, wherein $S_1$ or $S_3$ comprises a streptavidin tag.
221. The affinity reagent pool of clause 217, wherein the oligonucleotides comprise a detectable label or tag.
222. The affinity reagent pool of clause 221, wherein the detectable label or tag comprises a fluorophore, bioluminescent label, radiolabel, or enzymatic tag.
223. The affinity reagent pool of clause 217, wherein $S_2$ comprises no more than about 90 nucleotides.
224. The affinity reagent pool of clause 223, wherein $S_2$ comprises no more than about 80 nucleotides.
225. The affinity reagent pool of clause 224, wherein $S_2$ comprises no more than about 70 nucleotides.
226. The affinity reagent pool of clause 225, wherein $S_2$ comprises no more than about 60 nucleotides.
227. The affinity reagent pool of clause 226, wherein $S_2$ comprises no more than about 50 nucleotides.
228. The affinity reagent pool of clause 227, wherein $S_2$ comprises no more than about 40 nucleotides.
229. The affinity reagent pool of clause 228, wherein $S_2$ comprises no more than about 30 nucleotides.
230. The affinity reagent pool of clause 209, wherein the first affinity reagent and the second affinity reagent bind to the peptide epitopes with an equilibrium binding constant $K_d$ of less than $10^{-6}$ M.
231. The affinity reagent pool of clause 230, wherein $X_1$ and $X_2$ comprise degenerate amino acid sequences.
232. The affinity reagent pool of clause 231, wherein the degenerate amino acid sequences differ by one amino acid.
233. The affinity reagent pool of clause 231, wherein the degenerate amino acid sequences differ by more than one amino acid.
234. The affinity reagent pool of clause 231, 232, or 233, wherein the differing amino acids comprise similar chemical properties, wherein the chemical properties are selected from the group consisting of electrical charge, hydrophobicity, hydrophilicity, steric size, polarity, molecular structure, or a combination thereof
235. The affinity reagent pool of clause 231, 232, or 233, wherein the differing amino acids comprise dissimilar chemical properties, wherein the chemical properties are selected from the group consisting of electrical charge, hydrophobicity, hydrophilicity, steric size, polarity, molecular structure, or a combination thereof
236. The affinity reagent pool of clause 230, the first affinity reagent and the second affinity reagent bind to the peptide epitopes with an equilibrium binding constant $K_d$ of less than $10^{-7}$M.
237. The affinity reagent pool of clause 236, the first affinity reagent and the second affinity reagent bind to the peptide epitopes with an equilibrium binding constant $K_d$ of less than $10^{-8}$ M.
238. The affinity reagent pool of clause 237, wherein the first affinity reagent and the second affinity reagent bind to the peptide epitopes with an equilibrium binding constant $K_d$ of less than $10^{-9}$ M.
239. The affinity reagent pool of clause 238, wherein the first affinity reagent and the second affinity reagent bind to the peptide epitopes with an equilibrium binding constant $K_d$ of less than $10^{-10}$ M.
240. The affinity reagent pool of clause 239, wherein the first affinity reagent and the second affinity reagent bind to the peptide epitopes with an equilibrium binding constant $K_d$ of less than $10^{-11}$M.
241. The affinity reagent pool of clause 240, wherein the first affinity reagent and the second affinity reagent bind to the peptide epitopes with an equilibrium binding constant $K_d$ of less than $10^{-12}$ M.
242. The affinity reagent pool of clause 209, wherein the first affinity reagent and the second affinity reagent bind to the peptide epitopes for a time period of at least 1 minute.
243. The affinity reagent pool of clause 209, wherein the first affinity reagent and the second affinity reagent bind to the peptide epitopes for a time period of at least 15 minutes.
244. The affinity reagent pool of clause 209, the first affinity reagent and the second affinity reagent bind to the peptide epitopes for a time period of at least 1 hour.
245. The affinity reagent pool of clause 209, wherein the first affinity reagent and the second affinity reagent bind to the peptide epitopes when the peptide is in a native state.
246. The affinity reagent pool of clause 209, wherein the first affinity reagent and the second affinity reagent bind to the peptide epitopes when the peptide is in a non-native state.
247. The affinity reagent pool of clause 246, wherein the non-native state comprises a denatured state or a partially-folded state.
248. The affinity reagent pool of clause 209, wherein the affinity reagent pool further comprises a liquid medium.
249. The affinity reagent pool of clause 248, wherein the liquid medium comprises an aqueous medium.

What is claimed is:

1. A method of identifying an affinity reagent for an epitope, comprising: obtaining a first peptide library comprising a first plurality of at least 400 unique peptides, each peptide comprising a sequence of a formula αXβ, wherein X is the desired epitope, wherein the desired epitope X is a sequence of 2 to 20 amino acids, wherein the desired epitope X is identical among the first plurality of peptides, wherein α and β are flanking domains comprising known amino acid sequences; wherein the flanking domains α and β are any sequence of 1 to 10 amino acids, and wherein the flanking domains α and β vary among the first plurality of peptides;
exposing the first peptide library to a plurality of affinity reagents, thereby binding at least one affinity reagent of the plurality of affinity reagents to the first peptide library, wherein an affinity reagent of the plurality of affinity reagents comprises oligonucleotides, peptimers, mini protein binders, antibodies, antibody fragments, or a combination thereof;
determining the sequence or sequences of the at least one affinity reagents bound to the first plurality of peptides, thereby forming a reduced affinity reagent pool;
obtaining a second peptide library comprising a second plurality of at least 400 unique peptides, each peptide comprising a sequence of a formula γXδ, wherein X is the desired epitope, wherein the desired epitope X is a sequence of 2 to 20 amino acids, wherein the desired epitope X is identical among the second plurality of peptides, wherein γ and δ are flanking domains comprising known amino acid sequences; wherein the flanking domains γ and δ are any sequence of 1 to 10 amino acids, and wherein the flanking domains γ and δ vary among the second plurality of peptides;
exposing the second peptide library to the reduced affinity reagent pool, thereby binding at least one affinity reagent of the reduced affinity reagent pool to the second peptide library; and
determining the sequence or sequences of at least one affinity reagent of the reduced affinity reagent pool bound to the second peptide library, thereby identifying an affinity reagent for the desired epitope X.

2. The method of claim 1, wherein α and β comprise the same amino acid sequence.

3. The method of claim 1, wherein α and β comprise differing amino acid sequences.

4. The method of claim 1, wherein α and β comprise differing amino acid sequences from γ and δ.

5. The method of claim 1, wherein α and β comprise amino acid sequences with homogeneous chemical diversity.

6. The method of claim 5, wherein the amino acid sequences with homogeneous chemical diversity comprise amino acid sequences comprising two or more amino acid side groups with equivalent electrical charge, hydrophobicity, hydrophilicity, steric size, polarity, molecular structure, or a combination thereof.

7. The method of claim 1, wherein α and β comprise amino acid sequences with heterogeneous chemical diversity.

8. The method of claim 7, wherein the amino acid sequences with heterogeneous chemical diversity comprise amino acid sequences comprising two or more amino acid side groups with differing electrical charge, hydrophobicity, hydrophilicity, steric size, polarity, molecular structure, or a combination thereof.

9. The method of claim 1, wherein γ and δ comprise amino acid sequences with homogeneous chemical diversity.

10. The method of claim 9, wherein the amino acid sequences with homogeneous chemical diversity comprise amino acid sequences comprising two or more amino acid side groups with equivalent electrical charge, hydrophobicity, hydrophilicity, steric size, polarity, molecular structure, or a combination thereof.

11. The method of claim 1, wherein γ and δ comprise amino acid sequences with heterogeneous chemical diversity.

12. The method of claim 11, wherein the amino acid sequences with heterogeneous chemical diversity comprise amino acid sequences comprising two or more amino acid side groups with differing electrical charge, hydrophobicity, hydrophilicity, steric size, polarity, molecular structure, or a combination thereof.

13. The method of claim 1, further comprising washing the at least one affinity reagent of the plurality of affinity reagents bound to the first peptide library.

14. The method of claim 1, further comprising washing the at least one affinity reagent of the reduced affinity reagent pool bound to the second peptide library.

15. The method of claim 1, wherein the peptides within the first or second peptide library are in a native state.

16. The method of claim 1, wherein the peptides within the peptide first or second library are in a non-native state.

17. The method of claim 1, wherein the non-native state is a denatured state or a partially-folded state.

18. The method of claim 1, comprising repeating one or more times the steps of exposing the first peptide library to the plurality of affinity reagents and determining the sequence or sequences of the at least one affinity reagents.

19. The method of claim 1, comprising repeating one or more times the steps of exposing the second peptide library to the reduced affinity reagent pool and determining the sequence or sequences of the at least one affinity reagents.

20. The method of claim 1, wherein an affinity reagent of the plurality of affinity reagents comprises an oligonucleotide.

21. The method of claim 1, wherein X is a sequence of 3 amino acids.

22. The method of claim 1, wherein X is a sequence of 4 amino acids.

23. The method of claim 1, wherein X is a sequence of 5 amino acids.

24. The method of claim 1, wherein X is a sequence of 6 amino acids.

25. The method of claim 1, wherein the affinity reagent comprises an antibody or antibody fragment.

26. The method of claim 1, wherein the affinity reagent comprises an aptamer.

\* \* \* \* \*

SEQUENCE LISTING

<160> NUMBER OF SEQ ID NOS: 24

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Gln Lys Leu Ile Ser Glu Glu Asp Leu
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Ala Ala Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ala Ala Ala Cys
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Ala Ala Ala Ala
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Ala Ala Ala Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Ala Ala Ala Asp
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Tyr Trp Lys Tyr Trp
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Tyr Trp Lys Tyr Trp Lys Tyr Trp
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 9

Xaa Ala Ala Ala Ala Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 10

Xaa Xaa Ala Ala Ala Ala Xaa Xaa
1               5

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caagcagaag acggcatacg agat                                          24

<210> SEQ ID NO 12

```
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtgtagatct cggtggtcgc cgtatcatt                                       29

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ala Lys Asp
1

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Arg Asp Leu Arg Asp Leu Arg Asp Leu Arg Asp
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Gln Ala Thr Gln Ala Thr Gln Ala Thr Gln Ala
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Ser Leu Tyr Ser Leu Tyr Ser Leu Tyr Ser Leu
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Ala Ala Ala Leu
```

```
<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Ala Ala Ala Ser
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Ala Ala Ala Thr
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Ala Ala Asp
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Ala Ala Ala Ala
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Ala Ala Ala Cys
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                peptide

<400> SEQUENCE: 23

Tyr Ala Ala Ala Asp
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Ala Ala Ala Tyr
1               5
```

UNITED STATES PATENT AND TRADEMARK OFFICE
CERTIFICATE OF CORRECTION

| | | |
|---|---|---|
| PATENT NO. | : 11,993,865 B2 | Page 1 of 1 |
| APPLICATION NO. | : 17/424435 | |
| DATED | : May 28, 2024 | |
| INVENTOR(S) | : Joshua S. Klein et al. | |

It is certified that error appears in the above-identified patent and that said Letters Patent is hereby corrected as shown below:

On the Title Page

Item (54) and in the Specification Column 1, Line 1, change "SELECTION OF AFFINITY REAGENTS" to "SELECTION AND DESIGN OF AFFINITY REAGENTS".

Signed and Sealed this
Fourth Day of February, 2025

Coke Morgan Stewart
*Acting Director of the United States Patent and Trademark Office*